US011142566B2

(12) United States Patent
Luban

(10) Patent No.: US 11,142,566 B2
(45) Date of Patent: Oct. 12, 2021

(54) GENERATION OF HUMAN ANTI-HIV-1 ENV MONOCLONAL ANTIBODIES WITH NEUTRALIZING ACTIVITY FROM HUMANIZED MICE INFECTED WITH HIV-1

(71) Applicant: UNIVERSITY OF MASSACHUSETTS, Boston, MA (US)

(72) Inventor: Jeremy Luban, Newton, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 141 days.

(21) Appl. No.: 16/073,472

(22) PCT Filed: Mar. 8, 2017

(86) PCT No.: PCT/US2017/021426

§ 371 (c)(1),
(2) Date: Jul. 27, 2018

(87) PCT Pub. No.: WO2017/156170

PCT Pub. Date: Sep. 14, 2017

(65) Prior Publication Data

US 2019/0062409 A1 Feb. 28, 2019

Related U.S. Application Data

(60) Provisional application No. 62/305,891, filed on Mar. 9, 2016.

(51) Int. Cl.

| | |
|---|---|
| ***C07K 16/10*** | (2006.01) |
| ***C12N 15/86*** | (2006.01) |
| ***A61K 39/02*** | (2006.01) |
| ***A61K 39/12*** | (2006.01) |
| ***C07K 16/12*** | (2006.01) |
| ***A61K 31/7088*** | (2006.01) |
| ***A61K 39/21*** | (2006.01) |

(52) U.S. Cl.

CPC ...... *C07K 16/1063* (2013.01); *A61K 31/7088* (2013.01); *A61K 39/0225* (2013.01); *A61K 39/12* (2013.01); *A61K 39/21* (2013.01); *C07K 16/1045* (2013.01); *C07K 16/1207* (2013.01); *C12N 15/86* (2013.01); *C07K 2317/14* (2013.01); *C07K 2317/76* (2013.01); *C12N 2740/10044* (2013.01); *C12N 2740/16021* (2013.01); *C12N 2740/16023* (2013.01); *C12N 2740/16034* (2013.01); *C12N 2740/16043* (2013.01); *C12N 2740/16044* (2013.01); *C12N 2740/16122* (2013.01); *C12N 2740/16134* (2013.01); *C12N 2740/16322* (2013.01)

(58) Field of Classification Search

CPC ...... C07K 16/1063; C12N 2740/16122; C12N 2740/16134

See application file for complete search history.

(56) References Cited

U.S. PATENT DOCUMENTS

2011/0263460 A1 10/2011 Quinones-Mateu et al.
2014/0329312 A1 11/2014 North et al.

OTHER PUBLICATIONS

Brainard, D. M., et al., Jul. 2009, Inductionf of robust cellular and humoarl virus-specific adaptive immune responses in human immunodeficiency virus-infected humanized BLT mice, J. Virol. 83(14):7305-7321.*

Kramer, R. A., et al., 2005, The human antibody repertoire specific for rabies virus glycoprotein as selected from immune libraries, Eur. J. Immunol. 35:2131-2345.*

Reiser, J., et al., Nov. 2000, Development of multigene and regulated lentivirus vectors, J. Virol. 74(22):10589-10599.*

Fikrig, E., et al., Oct. 1990, Protection of mice against the Lyme disease agent by immunizing with recombinant OspA, Science 250:553-557.*

Sato, K., et al., 2010, Dynamics of memory and naive CD8+ T lymphocytes in humanized NOD/SCID/IL-2Rgammanull mice infected with CCR5-tropic HIV-1, Vaccine 28S:B32-B37.*

Akkina, R., et al., 2014, Humanized mice for studying human immune responses and generating human monoclonal antibodies, Microbiol. Spectrum 2(2):AID-0003-2012, pp. 1-12.*

Shultz, L. D., et al., Nov. 2012, Humanized mice fro immune system investigation: progress, promise, and challenges, Nat. Rev. Immunol. 12:786-798.*

Marsden, M. D., and J. A. Zack, 2017, Humanized mouse models for human immunodeficiency virus infection, Annu. Rev. Virol. 4:393-412.*

Crooks, E. T., et al., May 2015, Vaccine-elicited tier 2 HIV-1 neutralizing antibodies bind to quaternary epitopes involving glycan-deficient patches proximal to the CD4 binding site, PLoS Pathog. 11(5):e1004932, pp. 1-34.*

GenBank AY426125.1 "HIV-1 isolate JRCSF from USA envelope glycoprotein (env) gene, complete cds." Jun. 28, 2007 <URL: https://www.ncbi.nlm.nih.gov/nuccore/AYA426125>.

International Search Report and Written Opinion in related PCT Application No. PCT/US2017/021426, dated Jul. 7, 2017 (12 pages).

International Preliminary Report on Patentability in related PCT Application No. PCT/US2017/021426, dated Sep. 11, 2018 (8 pages).

* cited by examiner

*Primary Examiner* — Jeffrey S Parkin

(74) *Attorney, Agent, or Firm* — Lathrop GPM LLP; James H. Velema; Judith L. Stone-Hulslander

(57) ABSTRACT

The present invention provides highly efficient methods, and compositions related thereto, for generating high titer human antibodies or antibody fragments thereof in a mammalian subject. The methods comprise administering a virus or virus-like particle to a mammal comprising heterologous immune cells and isolating a population of immunoglobulin-producing cells from the mammal, thereby producing the antibodies or antibody fragments thereof.

10 Claims, 20 Drawing Sheets
(18 of 20 Drawing Sheet(s) Filed in Color)

Specification includes a Sequence Listing.

GENERATION OF HUMAN ANTI-HIV-1 ENV MONOCLONAL ANTIBODIES WITH NEUTRALIZING ACTIVITY FROM HUMANIZED MICE INFECTED WITH HIV-1

RELATED APPLICATIONS

This application is a 35 U.S.C. § 371 filing of International Patent Application No. PCT/US2017/021426, filed Mar. 8, 2017, which claims the benefit of priority to U.S. Provisional Patent Application No. 62/305,891, filed Mar. 9, 2016. The entire contents of these applications are incorporated herein by reference for all purposes.

STATEMENT REGARDING FEDERALLY FUNDED RESEARCH

This invention was made with government support under grant no. DA034990 awarded by the National Institutes of Health. The government has certain rights in this invention.

INTRODUCTION

Antibodies are an important class of therapeutic agents. However, when used in vivo, certain antibodies, such antibodies of non-human origin, may cause undesired immunogenicity. One approach for reducing the immunogenicity of rodent antibodies involves the production of chimeric antibodies, in which mouse variable regions (Fv) are fused with human constant regions. However, mice injected with hybrids of human variable regions and mouse constant regions develop a strong anti-antibody response directed against the human variable region, suggesting that the retention of the entire rodent Fv region in such chimeric antibodies may still result in unwanted immunogenicity in patients.

Grafting of rodent complementarity determining region (CDR) loops of variable domains onto human frameworks (i.e., humanization) has been used to further minimize rodent sequences. However, CDR loop exchanges still do not uniformly result in an antibody with the same binding properties as the antibody of origin. While the use of CDR grafting and framework residue preservation in a number of humanized antibody constructs has been reported, it is difficult to predict if a particular sequence will result in the antibody with the desired binding, and sometimes biological, properties.

Accordingly, there is a pressing need for an efficient means of generating fully human antibodies for use in the treatment of human disorders, such as inflammatory, autoimmune, proliferative, and infectious disorders. Such antibodies will preferably exhibit low immunogenicity in human subjects, allowing for repeated administration without adverse immune responses. The present invention provides a solution that addresses the problems of conventionally engineered antibodies, and in particular, provides a high titer pool of fully human, neutralizing antibodies against HIV-1 or against any heterologous protein of interest.

SUMMARY

The present invention provides highly efficient methods, and compositions related thereto, for generating high titer human antibodies or antibody fragments thereof in a mammalian subject. In an embodiment, the methods comprise the steps of: a) administering a virus or virus-like particle comprising the nucleotide sequence set forth in SEQ ID NO:15 to a mammal comprising heterologous immune cells; and b) isolating a population of mammalian immunoglobulin-producing cells from the mammal, thereby producing the antibodies or antibody fragments thereof.

In another embodiment, the methods further comprise the steps of: c) reverse transcribing VH and VL mRNA of the cell population into a pooled population of VH and VL cDNA sequences; d) cloning the pooled population of DNA fragments into expression vectors; and e) expressing the cloned DNA fragments, thereby producing the antibodies or fragments thereof.

In another embodiment, the methods further comprise the steps of: c) fusing the immunoglobulin-producing cells with myeloma cells to form parental hybridoma cells; and d) culturing the hybridoma cells, thereby producing the antibodies or antibody fragments thereof.

In yet another embodiment, the methods further comprise the steps of: c) fusing the immunoglobulin-producing cells with myeloma cells to form a population of parental hybridoma cells; d) culturing the population of hybridoma cells; e) reverse transcribing VH and VL mRNA of the cell population into a pooled population of VH and VL cDNA sequences; f) cloning the pooled population of DNA fragments into expression vectors and amplifying the cloned expression vectors; h) selecting a subpopulation of expression vectors which encodes antibodies or antibody fragments directed against a virus or virus-like particle encoded protein; i) and amplifying the subpopulation selected, thereby producing the antibodies or antibody fragments thereof.

In an embodiment of the invention, the heterologous immune cells are human immune cells. In an embodiment, the mammal is a non-human mammal. In an embodiment, the mammal is a rodent. In an embodiment, the rodent is a mouse. In an embodiment, mouse is a transgenic mouse. In a certain embodiment, the transgenic mouse lacks mature lymphocytes and natural killer (NK) cells. In a particular embodiment, the transgenic mouse is a NOD-scid IL2R$\gamma^{null}$ mouse strain.

In an embodiment of the invention, the transgenic mouse comprises engrafted human tissue, the tissue comprising one or more tissues selected from the group consisting of human fetal thymus tissue, human fetal liver tissue, and human $CD34^{+}$ fetal liver cells. In a certain embodiment, the human fetal thymus tissue and/or human fetal liver tissue is engrafted under the mouse kidney capsule. In a particular embodiment, the human $CD34^{+}$ fetal liver cells are engrafted systemically.

In an embodiment, the invention provides human antibodies or antibody fragments thereof. In another embodiment, the human antibodies are anti-HIV-1 antibodies. In yet another embodiment, the human antibodies are anti-HIV-1 neutralizing antibodies.

In an embodiment of the invention, the virus or virus-like particle further comprises a nucleotide sequence encoding a heterologous protein. In another embodiment, the heterologous protein is the outer surface protein A (OspA) of the spirochete *Borrelia burgdorferi*. In yet another embodiment, the human antibodies are anti-OspA antibodies.

In an embodiment, the invention provides an isolated nucleic acid comprising a nucleotide sequence at least about 60%, 65%, 70%, 75%, 80%, 85%, 90%, 95%, 96%, 97%, 98%, 99% identity to SEQ ID NO:1, wherein the isolated nucleic acid comprises at least one nucleotide sequence selected from the group consisting of SEQ ID NOS:2, 3, and 4. In another embodiment, the isolated nucleic acid comprises a nucleotide sequence selected from the group consisting of SEQ ID NOS:5, 6, 7, 8, 9, 10, and 11.

In an embodiment, the invention provides a vector comprising an isolated nucleic acid any of the nucleic acid sequences recited herein, wherein the vector optionally comprises a deletion of a viral envelope gene.

In an embodiment of the invention, the vector encodes a provirus comprising a gene encoding a protein that alters at least one viral function, wherein the at least one viral function is selected from the group consisting of target cell binding, target cell fusion, provirus integration, provirus reverse transcription activity, provirus translation activity, and virion assembly. In an embodiment, the target cell is a DC and the at least one viral function is provirus integration. In an embodiment, the provirus integrates into the DC genome at a frequency of at least about 1.34%. In an embodiment, the target cell is a DC, and wherein the at least one viral function is provirus reverse transcription activity. In an embodiment, the provirus reverse transcription activity is between $1\times10^3$ and $8\times10^3$ HIV-1 genome copies per cell, as measured by polymerase chain reaction. In an embodiment, the provirus reverse transcription activity is between $10^5$ and $10^6$ HIV-1 genome copies per ml, as measured by polymerase chain reaction.

In an embodiment of the invention, the provirus encodes a protein that alters at least one target cell function. In a particular embodiment, the target cell is selected from the group consisting of a dendritic cell (DC), a helper T (Th) cell, and a cytotoxic T (TC) cell. In a certain embodiment, the target cell is a DC and the at least one target cell function is DC activation.

In an embodiment, the invention provides an isolated host cell comprising any of the vectors recited herein. In an embodiment, the host cell is a prokaryotic or a eukaryotic cell. In an embodiment, the eukaryotic cell is a mammalian cell. In an embodiment, the mammalian cell is a HEK cell.

In an embodiment, the invention provides a method of producing a recombinant virus or virus-like particle, the method comprising culturing an isolated host cell in culture medium such that a recombinant virus or virus-like particle is produced. In an embodiment, the virus or virus-like particle is a replication incompetent virus or virus-like particle.

In an embodiment, the invention provides a method of altering an immune response in a mammal, the method comprising administering a recombinant virus or virus-like particle to a DC such that an immune response is altered. In an embodiment, the recombinant virus or virus-like particle is administered to the DC in vivo. In an embodiment, the recombinant virus or virus-like particle is administered to the DC ex vivo. In an embodiment, the immune response is selected from the group consisting of DC activation, Th activation, TC activation, B cell maturation, B cell activation, and antibody production.

In an embodiment, the invention provides a composition comprising a virally transduced DC, wherein the DC is transduced with a recombinant virus or virus-like particle. In an embodiment, the composition is a pharmaceutical composition. In an embodiment, the pharmaceutical composition is a vaccine. In an embodiment, the invention provides a method of treating a disease or disorder in a mammal, the method comprising administering a composition recited herein to the mammal, thereby treating the disease or disorder In an embodiment, the invention provides a method of treating a disease or disorder in a mammal, the method comprising administering a virus or virus-like particle comprising the nucleotide sequence set forth in SEQ ID NO: 15 to the mammal, thereby treating the disease or disorder.

In an embodiment, the invention provides a hybridoma produced according to any method recited herein. In another embodiment, the invention provides a monoclonal antibody isolated from a hybridoma. In an embodiment, the monoclonal antibody is a human antibody. In another embodiment, the invention provides a library of antibodies or antibody fragments thereof produced according to any method recited herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION

Figure 1A:
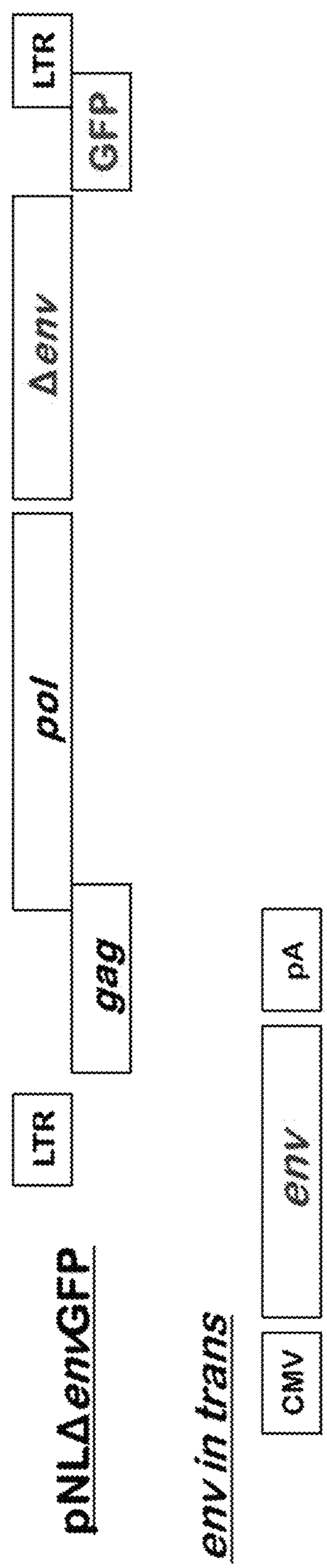
FIG. 1A depicts a schematic of the two-plasmid lentiviral system for generating pseudotyped lentivirus.

Antibodies are an important class of therapeutic agents. However, when used in vivo, certain antibodies may cause undesired immunogenicity. As most monoclonal antibodies are derived from rodents, repeated use in humans results in the generation of an immune response against the therapeutic antibody, e.g., human against mouse antibodies or HAMA. Such an immune response results in a loss of therapeutic efficacy at a minimum and a potentially fatal anaphylactic response at a maximum. One approach for reducing the immunogenicity of rodent antibodies involves the production of chimeric antibodies, in which mouse variable regions (Fv) are fused with human constant regions (see Liu et al., Proc. Natl. Acad. Sci., 1987; 84:3439-3443). However, mice injected with hybrids of human variable regions and mouse constant regions develop a strong anti-antibody response directed against the human variable region, suggesting that the retention of the entire rodent Fv region in such chimeric antibodies may still result in unwanted immunogenicity in patients.

Additionally, grafting of rodent complementarity determining region (CDR) loops of variable domains onto human frameworks (i.e., humanization) has been used to further minimize rodent sequences (see Jones et al., Nature, 1986; 321:522-535; Verhoeyen et al., Science, 1988; 239:1534-1536). However, CDR loop exchanges still do not uniformly result in an antibody with the same binding properties as the antibody of origin. Changes in framework residues (FR), residues involved in CDR loop support, in humanized antibodies also are often required to preserve antigen binding affinity (see Kabat et al., J. Immunol., 1991; 147:1709-1719). While the use of CDR grafting and framework residue preservation in a number of humanized antibody constructs has been reported, it is difficult to predict if a particular sequence will result in the antibody with the desired binding, and sometimes biological, properties (see Queen et al., Proc. Natl. Acad. Sci., 1989; 86:10029-10033); Gorman et al., Proc. Natl. Acad. Sci., 1991; 88:4181-4185; and Hodgson, J., Biotechnology, 1991; 9:421-425).

Accordingly, there is a pressing need for an efficient means of generating fully human antibodies for use in the treatment of human disorders, such as inflammatory, autoimmune, proliferative, and infectious disorders. Such antibodies will preferably exhibit low immunogenicity in human subjects, allowing for repeated administration without adverse immune responses. The present invention provides a solution that addresses the problems of conventionally engineered antibodies, and in particular, provides a high titer pool of fully human, neutralizing antibodies against HIV-1, as well as other heterologous proteins.

1. HIV-1

The acronym "HIV" or terms "AIDS virus" or "human Immunodeficiency virus" are used herein to refer to these HIV viruses, and HIV-related and -associated viruses, generically. As used herein, the terms "virus-like particle" or "VLP" refer to a nonreplicating, viral shell, preferably derived entirely or partially from virus proteins. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, biophysical characterization, and the like (see Baker et al., Biophys. J., 1991; 60:1445-1456; Hagensee et al., J. Virol., 1994: 68:4503-4505). For example, VLPs can be isolated by density gradient centrifugation and/or identified by characteristic density banding (e.g., Examples). Alternatively, cryoelectron microscopy can be performed on vitrified aqueous samples of the VLP preparation in question, and images recorded under appropriate exposure conditions.

By conventional criteria, anti-HIV-1 immunity is detected in most people who are HIV-1-infected. Yet, they can be secondarily infected with HIV-1, and unless treated with anti-retrovirals, they progress to AIDS. Effective antiviral immunity requires that, in addition to presenting viral peptides, and elaborating accessory molecules that stimulate proliferation, dendritic cells must provide a third signal (e.g., IL-12) to naïve T cells. There are many ways that a dendritic cell can be matured to present antigen, though the outcome of T cell priming may be antigen-specific immunization or antigen-specific tolerance. Generation of the third signal requires that pattern recognition receptors be activated directly within the antigen presenting dendritic cell. HIV-1 encounter with dendritic cells results in efficient antigen presentation. However, because the dendritic cell has multiple blocks to HIV-1 replication, pattern recognition receptors are not activated, and dendritic cell maturation is insufficient to generate the third signal. Hence, the immune response to HIV-1 is not protective and may even be tolerogenic.

Productive infection of dendritic cells by HIV-1 is blocked at two major steps in the replication cycle. The first block occurs at non-productive entry pathways that utilize DC-SIGN or other lectins over the productive CD4/CCRS entry pathway. This block to productive entry can be overcome by pseudo-typing HIV-1 virions with the vesicular stomatitis virus glycoprotein. VSV G-pseudotyping drives fusion of HIV-1 virions from endosomes into the cytoplasm where productive infection (reverse transcription) can occur.

The second block occurs during reverse transcription. SAMHD1, a myeloid-specific, triphosphohydrolase, maintains low dNTP levels in the dendritic cell cytoplasm, thereby preventing reverse transcription. This block can be overcome by expressing the viral gene Vpx. Vpx promotes SAMHD1 degradation, thereby increasing the levels of dNTPs needed for reverse transcription. Accordingly, Vpx can be provided in cis or in trans to increase HIV-1 transduction efficiency.

The result of VSV G-pseudotyping and Vpx incorporation into HIV-1 virions is that high-efficiency HIV-1 transduction of dendritic cells can be achieved. The present invention provides for methods of administering an HIV-1 virus comprising a pseudotyped envelope to a transgenic mammal comprising heterologous (i.e., human) immune cells, thereby resulting in the generation of a robust and protective anti-HIV-1 immune response. The anti-HIV-1 immune response is characterized by the generation of high-titer human anti-HIV-1 neutralization antibodies.

2. Antibodies

The present invention provides highly efficient methods, and compositions related thereto, for generating high titer human antibodies or antibody fragments thereof in a mammalian subject. The methods comprise administering a virus or virus-like particle to a mammal comprising heterologous immune cells and isolating a population of immunoglobulin-producing cells from the mammal, thereby producing the antibodies or antibody fragments thereof. Of particular significance, the methods provided for by the present invention allow for heterologous proteins to be presented by the recombinant virus. Accordingly, the generation of human antibodies against any antigenic peptide is envisaged and described herein. In particular, it is contemplated that the present invention can be utilized to generate human antibodies against: emerging viruses of any type, for example, Ebola or Chikungunya virus; influenza antigens; antibiotic-resistant bacteria, for example, MRSA and drug-resistant Tuberculosis; tumor-specific antigens; and Rd D antigen, to treat hemolytic disease of the newborn.

The term "antibody" broadly refers to any immunoglobulin (Ig) molecule comprised of four polypeptide chains, two heavy (H) chains and two light (L) chains, or any functional fragment, mutant, variant, or derivative thereof that retains the essential epitope binding features of an Ig molecule. Such mutant, variant, or derivative antibody formats are known in the art, non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antibody fragment" refers to a portion of an antibody that retains some ability to selectively bind the epitopic determinant. Examples of an antibody fragment include:

(i) Fab, the fragment which contains a monovalent antigen-binding fragment of an antibody molecule can be produced by digestion of whole antibody with the enzyme papain to yield an intact light chain and a portion of one heavy chain;

(ii) Fab', the fragment of an antibody molecule can be obtained by treating whole antibody with pepsin, followed by reduction, to yield an intact light chain and a portion of the heavy chain; two Fab' fragments are obtained per antibody molecule;

(iii) F(ab')2, the fragment of the antibody that can be obtained by treating whole antibody with the enzyme pepsin without subsequent reduction; F(ab')2 is a dimer of two Fab' fragments held together by two disulfide bonds;

(iv) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In certain embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In an embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences. Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA, 1990; 87: 2264-2268, modified as in Karlin & Altschul, Proc. Natl. Acad. Sci. USA, 1993; 90: 5873-5877.

Another example of a mathematical algorithm used for comparison of sequences is the algorithm of Myers & Miller, CABIOS, 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA, 1988; 85: 2444-2448.

Advantageous for use according to the present invention is the WU-BLAST (Washington University BLAST) version 2.0 software. This program is based on WU-BLAST version 1.4, which in turn is based on the public domain NCBI-BLAST version 1.4 (see Altschul & Gish, 1996, Local alignment statistics, Doolittle ed., Methods in Enzymology 266: 460-480; Altschul et al., Journal of Molecular Biology, 1990; 215: 403-410; Gish & States, 1993; Nature Genetics 3: 266-272; Karlin & Altschul, 1993; Proc. Natl. Acad. Sci. USA, 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

2. Vectors

The nucleotide sequences of the present invention may comprise or be inserted into "vectors." The term vector is widely used and understood by those of skill in the art, and as used herein, the term vector is used consistent with its meaning to those of skill in the art. For example, the term vector is commonly used by those skilled in the art to refer to a vehicle that allows or facilitates the transfer of nucleic acid molecules from one environment to another or that allows or facilitates the manipulation of a nucleic acid molecule.

Accordingly, the present invention provides viral vectors and their use in generating recombinant virus or virus-like particles. In an embodiment of the invention, any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in the generation of vaccines, such as dendritic cell-based or DNA-containing vaccines, any vector that allows for the expression of the antibodies and/or antigens of the present invention and is safe for use in vivo may be used. In certain embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoan vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-1 antigen and/or protective immunity against HIV-1, expression vectors that are suitable for expression in that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to prevent replication in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In particular embodiments of the present invention viral vectors are used. Viral expression vectors are well known to those skilled in the art and include, for example, vectors derived from viruses such as adenoviruses, adeno-associated viruses (AAV), alphaviruses, herpesviruses, poxviruses, avipox viruses, attenuated poxviruses, vaccinia viruses, modified vaccinia viruses, retroviruses, and lentiviruses.

A particularly preferred lentiviral vector is one derived from HIV, most preferably HIV-1, HIV-2, or chimeric combinations thereof. Of course different serotypes of retroviruses, especially HIV, may be used singly or in any combination to prepare vectors for use in the present invention. In particular embodiments, vectors of the invention contain cis-acting elements that are present in the wild-type virus, but not present in a "basic" lentiviral vector. A "basic" lentiviral vector contains minimally, LTRs and packaging sequences in the 5' leader and gag encoding sequences, but can also optionally contain the RRE element to facilitate nuclear export of vector RNA in a Rev dependent manner. A preferred vector additionally contains nucleotide sequences that enhance the efficiency of transduction into cells.

An example of such a vector is pN2cGFP, a vector that contains the complete sequences of gag and pol. Another example is a vector that contains sequences from about position 4551 to position 5096 in pol (reference positions from the pNL4-3 sequence, Accession number M19921, HIVNL43 9709 bp, kindly provided by C. E. Buckler, NIAID, NIH, Bethesda, Md.). However any cis-acting sequence from the wt-HIV that can improve vector transduction efficiency may be used. Other examples of vectors capable of efficient transduction via the present invention are cr2HIV constructs as described in U.S. Pat. No. 5,885,806.

Additional examples of viral vector constructs that may be used in the present invention are found in U.S. Pat. No. 5,885,806, which is hereby incorporated by reference as if fully set forth. The constructs in U.S. Pat. No. 5,885,806 are merely examples that do not limit the scope of vectors that efficiently transduce cells. Instead, the constructs provide additional guidance to the skilled artisan that a viral vector for use with the present invention may contain minimal sequences from the wild-type virus or contain sequences up to almost the entire genome of wild-type virus, yet exclude an essential nucleic acid sequence required for replication and/or production of disease.

Furthermore, placing sequences from other viral backbones into viral vectors of interest, such as the cytomegalovirus (CMV), is also well known in the art. Regardless of the actual viral vector used, various accessory proteins encoded by, and sequences present in, the viral genetic material may be left in the vector or helper genomes if these proteins or sequences increase transduction efficiency in certain cell types. Numerous routine screens are available to determine whether certain genetic material increases transduction efficiency by incorporating the sequence in either the vector or helper genomes. A certain embodiment of the invention is to not include accessory proteins in either the vector or helper genomes. But this preference does not exclude embodiments of the invention where accessory proteins and other sequences are left in either the vector or a helper genome to increase transduction efficiency.

The viral vectors used in the present invention may also result from "pseudotype" formation, where co-infection of a cell by different viruses produces progeny virions containing the genome of one virus encapsulated within an outer layer containing one or more envelope protein of another virus. This phenomenon has been used to package viral vectors of interest in a "pseudotyped" virion by co-transfecting or co-infecting a packaging cell with both the viral vector of interest and genetic material encoding at least one envelope protein of another virus or a cell surface molecule. See U.S. Pat. No. 5,512,421. Such mixed viruses can be neutralized by anti-sera against the one or more heterologous envelope proteins used. One virus commonly used in pseudotype formation is the vesicular stomatitis virus (VSV), which is a rhabdovirus. The use of pseudotyping broadens the host cell range of the virus by including elements of the viral entry mechanism of the heterologous virus used.

Pseudotyping of viral vectors and VSV for use in the present invention results in viral particles containing the viral vector nucleic acid encapsulated in a nucleocapsid which is surrounded by a membrane containing the VSV G protein. The nucleocapsid preferably contains proteins normally associated with the viral vector. The surrounding VSV G protein containing membrane forms part of the viral particle upon its egress from the cell used to package the viral vector. Examples of packaging cells are described in U.S. Pat. No. 5,739,018. In a certain embodiment of the invention, the viral particle is derived from HIV and pseudotyped with VSV G protein. Pseudotyped viral particles containing the VSV G protein can infect a diverse array of cell types with higher efficiency than amphotropic viral vectors. The range of host cells include both mammalian and non-mammalian species, such as humans, rodents, fish, amphibians and insects. In certain embodiments of the present invention, HIV-1 viral particles are pseudotyped with either JRCSF or JRFL proteins which provide distinct cellular tropisms (see Koyanagi et al., 1987, Science; 236: 819-822). In particular embodiments, the viral particles are pseudotyped with the JRFL protein which allows the virions to bind to and transduce dendritic cells.

Viral vectors for use in the transduction methods of the invention can also comprise and express one or more nucleic acid sequences under the control of a promoter present in the virus or under the control of a heterologous promoter introduced into the vector. The promoters may further contain insulatory elements, such as erythroid DNAse hypersensitive sites, so as to flank the operon for tightly controlled gene expression. Preferred promoters include the HIV-LTR, CMV promoter, PGK, U1, EBER transcriptional units from Epstein Barr Virus, tRNA, U6 and U7. While Pol II promoters are preferred, Pol III promoters may also be used. Tissue specific promoters are also embodied by the present invention. For example, the beta globin Locus Control Region enhancer and the alpha and beta globin promoters can provide tissue specific expression in erythrocytes and erythroid cells. Another embodiment is to use cis-acting sequences that are associated with the promoters. For example, The U1 gene may be used to enhance antisense gene expression where non-promoter sequences are used to target the antisense or ribozymes molecule to a target spliced RNA as set out in U.S. Pat. No. 5,814,500, which is hereby incorporated by reference.

Of course any cis-acting nucleotide sequences from a virus may be incorporated into the viral vectors of the invention. In particular, cis-acting sequences found in retroviral genomes are preferred. For example, cis-acting nucleotide sequence derived from the gag, pol, env, vif, vpr, vpu, tat or rev genes may be incorporated into the viral vectors of the invention to further increase transduction efficiency. Preferably, a cis-acting sequence does not encode an expressed polypeptide; is not expressed as a polypeptide or part thereof due to genetic alteration, such as deletion of a translational start site; encodes only a portion or fragment of a larger polypeptide; or is a mutant sequence containing one or more substitutions, additions, or deletions from the native sequence. An example of a cis-acting sequence is the cPPT (central polypurine tract) sequence identified within the HIV pol gene.

Said one or more nucleotide sequence in the viral vectors of the invention may be found in the virus from which the vector is derived or be a "heterologous" sequence. The sequence is preferably a full-length or partial sequence that is or encodes a gene product of interest. Such sequences and gene products are preferably biologically active agents capable of producing a biological effect in a cell. Examples of such agents include proteins, ribonucleic acids, enzymes, transporters or other biologically active molecules. In a particular embodiment of the present invention, a heterologous sequence is the outer surface protein A (OspA) of the spirochete *Borrelia burgdorferi*.

The nucleotide sequences and vectors of the invention can be delivered to cells, for example, if the aim is to express the HIV-1 antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, mammalian cells, and mammalian hybridoma cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

Following expression, the antibodies and/or antigens of the invention can be isolated and/or purified or concentrated using any suitable technique known in the art. For example, anion or cation exchange chromatography, phosphocellulose chromatography, hydrophobic interaction chromatography, affinity chromatography, immuno-affinity chromatography, hydroxyapatite chromatography, lectin chromatography, molecular sieve chromatography, isoelectric focusing, gel electrophoresis, or any other suitable method or combination of methods can be used.

In particular embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In certain embodiments the subject is a human, for example a human that is infected with, or is at risk of infection with, HIV-1.

For such in vivo applications, the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

3. Transduction

The present invention also provides highly efficient methods, and compositions related thereto, for the stable transduction of target cells with viral vectors and viral particles. Of course any cell can be used in the practice of the invention. Preferably, the cell to be transduced is a eukaryotic cell. More preferably, the cell is a primary cell. Cell lines, however, may also be transduced with the methods of the invention and, in many cases, more easily transduced. In one embodiment of the invention, the cell to be transduced is a primary lymphocyte (such as a T lymphocyte) or a macrophage (such as a monocytic macrophage), or is a precursor to either of these cells, such as a hematopoietic stem cell. Other embodiments of the invention provide for transduction of cells of the hematopoietic system, or, more generally, cells formed by hematopoiesis as well as the stem cells from which they form. Such cells include granulocytes and lymphocytes formed by hematopoiesis as well as the progenitor pluripotent, lymphoid, and myeloid stem cells.

An embodiment of the present invention provides for the transduction of cells that aid in the functioning of immune system, such as antigen presenting dendritic cells. In a particular embodiment, the invention provides for the transduction of dendritic cells with an HIV-1 pseudotyped with an envelope that preferentially binds and fuses with dendritic cell membrane. In certain embodiments, the dendritic cells are virally transduced in vivo, whereas in other embodiments the dendritic cells are transduced ex vivo.

Incubation of the cells with the virus or virus-like particle may be for different lengths of time, depending on the conditions and materials used. Factors that influence the incubation time include the cell, vector and MOI (multiplicity of infection) used, the molecule(s) and amounts used to bind the cell surface, whether and how said molecule(s) are immobilized or solubilized, and the level of transduction efficiency desired.

A cell to be transduced can be present as a single entity, or can be part of a population of cells. Such a "population of cells" can comprise, for instance, a cell culture (either mixed or pure), a tissue (e.g., epithelial, stromal or other tissue), an organ (e.g., heart, lung, liver, gallbladder, urinary bladder, eye, and other organs), an organ system (e.g., circulatory system, respiratory system, gastrointestinal system, urinary system, nervous system, integumentary system or other organ system), a blastocyst, an embryonic stem cell a cell from a fetus (e.g. for the treatment of a genetic disorder/disease or for creating transgenic animals), diseased tissues such as a tumor or the site of an infection, or an organism (e.g., a bird, mammal, marine organism, fish, plant or the like). Preferably, the organs/tissues/cells being targeted are of the circulatory system (including for example, but not limited to heart, blood vessels, and blood), respiratory system (e.g., nose, pharynx, larynx, trachea, bronchi, bronchioles, lungs, and the like), gastrointestinal system (including for example mouth and oral tissues, pharynx, esophagus, stomach, intestines, salivary glands, pancreas, liver, gallbladder, and the like), mammary system (such as breast epithelial cells and supporting cells in the tissue), urinary system (such as kidneys, ureters, urinary bladder, urethra, and the like), nervous system (including, but not limited to, brain and spinal cord, and special sense organs, such as the eye) and integumentary system (e.g., skin).

4. Therapeutics

The present invention also includes the use of the transduced cells in other applications, including the production of useful gene products and proteins by expression of a nucleic acid present in the vector, or the therapy of living subjects afflicted or at risk of being afflicted with a disease. In an embodiment of the invention, the transduced cell is a dendritic cell. In another embodiment, the transduced dendritic cell comprises a dendritic cell vaccine.

The dendritic cell vaccine may be prepared from dendritic cells by any method without particular limitation. For example, the dendritic cells are mixed with an agent (such as physiological saline or a Ringer solution) that is commonly formulated in a vaccine preparation. In the method of producing a dendritic cell vaccine of the present invention, a sufficient amount of monocytes or dendritic cells for producing a dendritic cell vaccine can be prepared in a short period of time, and a dendritic cell vaccine can be timely prepared without requiring a store of monocytes or dendritic cells. Therefore, monocytes or dendritic cells optionally produced can be used without subjecting to cryopreservation for producing a dendritic cell vaccine. Consequently, damage of cells and a reduction in antigen-presenting ability of the dendritic cells by freezing can be avoided.

When provided prophylactically, the dendritic cell vaccine of the invention are ideally administered to a subject in advance of HIV infection, or evidence of HIV infection, or in advance of any symptom due to AIDS, especially in high-risk subjects. The prophylactic administration of the compositions can serve to provide protective immunity of a subject against HIV-1 infection or to prevent or attenuate the progression of AIDS in a subject already infected with HIV-1. When provided therapeutically, the compositions can serve to ameliorate and treat AIDS symptoms and are advantageously used as soon after infection as possible, preferably before appearance of any symptoms of AIDS but may also be used at (or after) the onset of the disease symptoms.

The compositions can be administered using any suitable delivery method including, but not limited to, intramuscular, intravenous, and intradermal. Such techniques are well known to those of skill in the art.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

The compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such certain immunogen is HIVA (described in WO 01/47955), which can be administered as a protein, on a plasmid (e.g., pTHr.HIVA) or in a viral vector (e.g., MVA. HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an antibody, antigen or antibody-antigen complex of the present invention, a nucleic acid encoding an antibody, antigen or antibody-antigen complex of the invention or an expression vector, preferably an adenovirus vector, encoding an antibody, antigen or antibody-antigen complex of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

It is to be understood and expected that variations in the principles of invention as described above may be made by one skilled in the art and it is intended that such modifications, changes, and substitutions are to be included within the scope of the present invention.

The invention will now be further described by way of the following non-limiting examples.

EXAMPLES

Example 1. Generation of HIV-1 Lentiviral Vectors and Infective Proviruses

Genetically divergent HIV-1 variants with distinct cellular tropisms have been isolated from individual patients. From one such patient identified as J.R., related but unique HIV-1 viruses were sequestered from frontal lobe brain tissue and cerebrospinal fluid. Accordingly, the viruses were identified as JR-FL (frontal lobe) and JR-CSF (cerebrospinal fluid), and while both viruses were capable of replicating in peripheral blood lymphocytes, only the JR-FL virus was able to replicate in monocytes or macrophages (see Koyanagi et al., 1987, Science; 236:819-822). Subsequent cloning and expression studies determined that the JR-FL and JR-CSF viruses contain unique env genes which confer their previously observed cellular tropisms (see Peters et al., 2004, J. Virol.; 78:6915-6926).

Figure 1B:
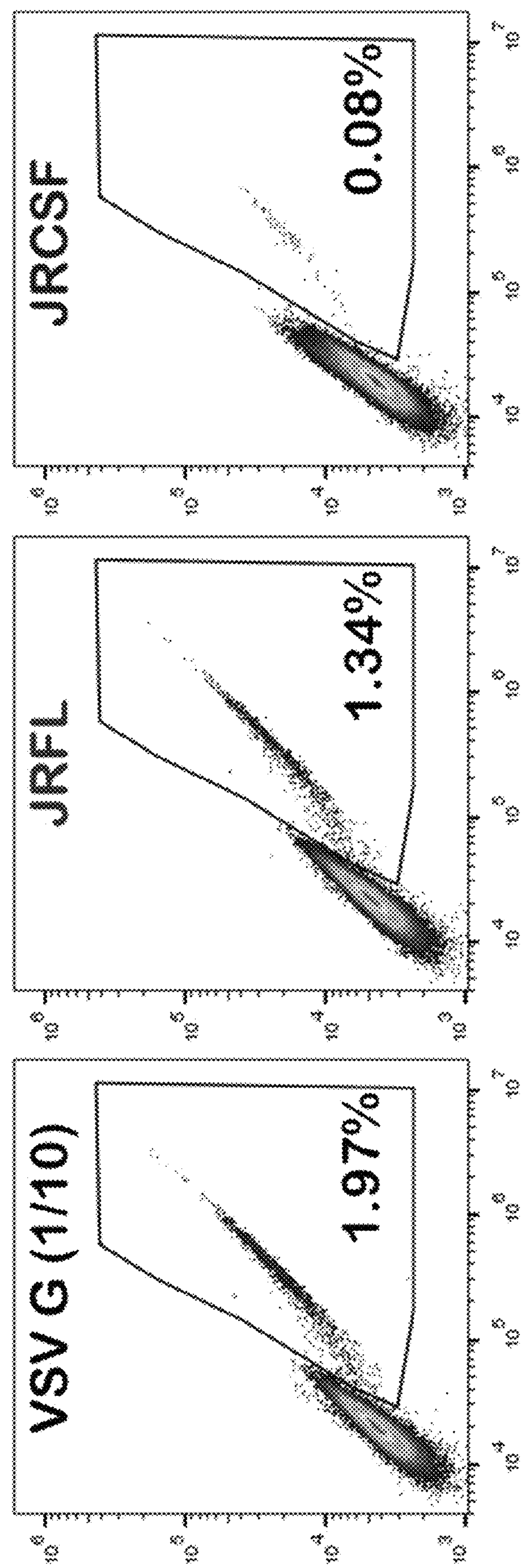
FIG. 1B depicts a FACS plot showing the transduction efficiency of VSV-G, JRFL, and JRCSF pseudotyped HIV-1 viruses.
Figure 1C:
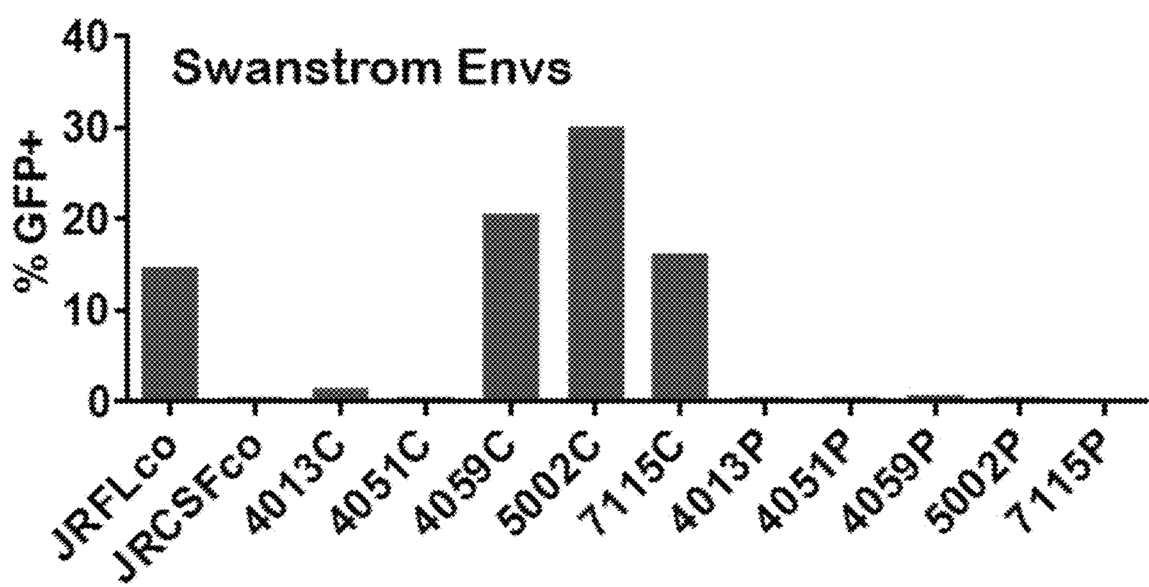
FIG. 1C depicts the transduction efficiency of HIV-1 pseudotyped with the indicated Env proteins.
Figure 2:
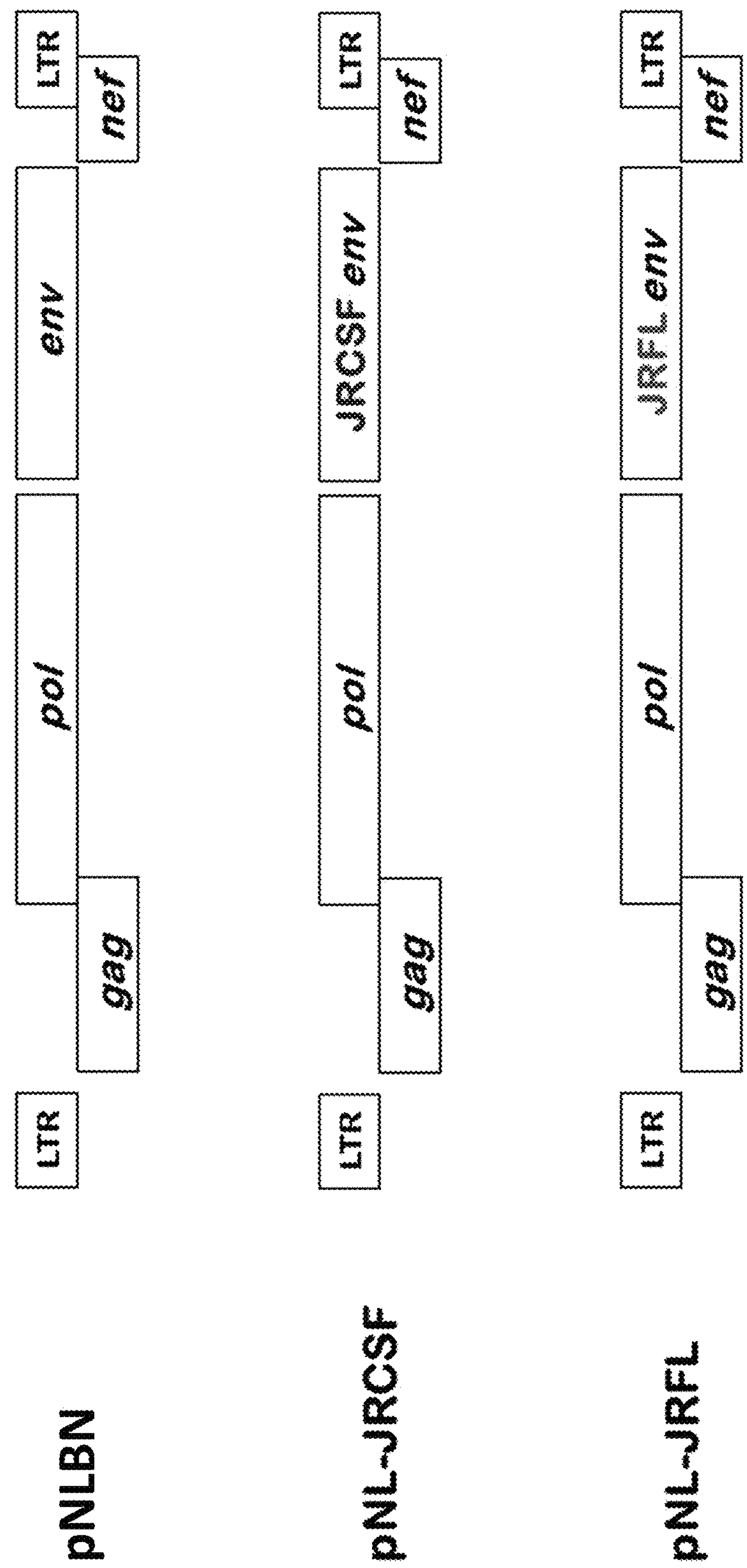
FIG. 2 depicts a schematic of the one-plasmid lentiviral system for generating pseudotyped lentivirus.

Since DCs infected with vesicular stomatitis virus-pseudotyped HIV-1 present viral antigens to $CD4^+$ and $CD8^+$ T-cells better than DCs infected with wild-type HIV-1 (see Granelli-Piperno et al., 2000, J. Immunol.; 165:6620-6626, which is incorporated by reference herein in its entirety), virus entry is considered an initial limiting factor in DC transduction and activation. Accordingly, the JRFL and JRCSF env genes were screened for their ability to support HIV-1 DC transduction. The pNL plasmids described herein are based upon the pNL4-3 lentiviral vector described by Akio Adachi et al., but with BstEII and NotI restrictions sites engineered 5' and 3', respectively, to the env gene (see Adachi et al., 1986, J. Virol.; 59:284-291, which is incorporated by reference herein in its entirety). For this study, HEK-293 cells were transfected using standard calcium phosphate transfection protocols with the pNLΔenvGFP lentiviral plasmid (SEQ ID NO:12). The pNLΔenvGFP is based upon the pNL plasmid with the env gene deleted and a heterologous green fluorescent protein (GFP) gene inserted. A second plasmid containing a VSV-G (SEQ ID NO:13), JRFL (SEQ ID NO: 15), or a JRCSF (SEQ ID NO: 14) env gene was provided to the HEK-293 cells in trans. FIG. 1A depicts a schematic of the two-plasmid lentiviral system described herein. Infective HIV-1 virus was collected and minimally processed prior to DC infection. Infected cells were analyzed by flow-activated cell sorting (FACS). As shown in FIG. 1B, the VSV-G and JRFL pseudotyped viruses were able to transduce DCs (1.97% and 1.34%, respectively), whereas the JRCSF pseudotyped virus was ineffective at transducing DCs (0.08%). FIG. 1C shows a screen of different HIV-1 Envelope proteins (cloned from the immunologically privileged, central nervous system of AIDS patients) for the ability to pseudotype HIV-1 and transduce DCs. Clones 4059C (SEQ ID NO:17), 5002C (SEQ ID NO:18), and 7115C (SEQ ID NO:19), for example, all have significantly more DC transducing activity than does JRFL, even though JRFL is codon optimized and these other Envelopes were not. In ongoing experiments, these Envelopes are being engineered into our provirus clones to be tested for the ability to elicit antibody responses. Accordingly, the JR-FL env provides a ready and effective means for transducing DCs. For subsequent in vitro and in vivo studies, HIV-1 plasmids were engineered to contain the JRFL and JRCSF env genes in cis. FIG. 2 depicts a schematic of the pNLBN (SEQ ID NO:5), pNL-JRCSF (SEQ ID NO:6), and pNL-JRFL (SEQ ID NO:7), and plasmids described herein.

Example 2. Generation of Monocyte-Derived DCs (MDDCs)

Figure 3:
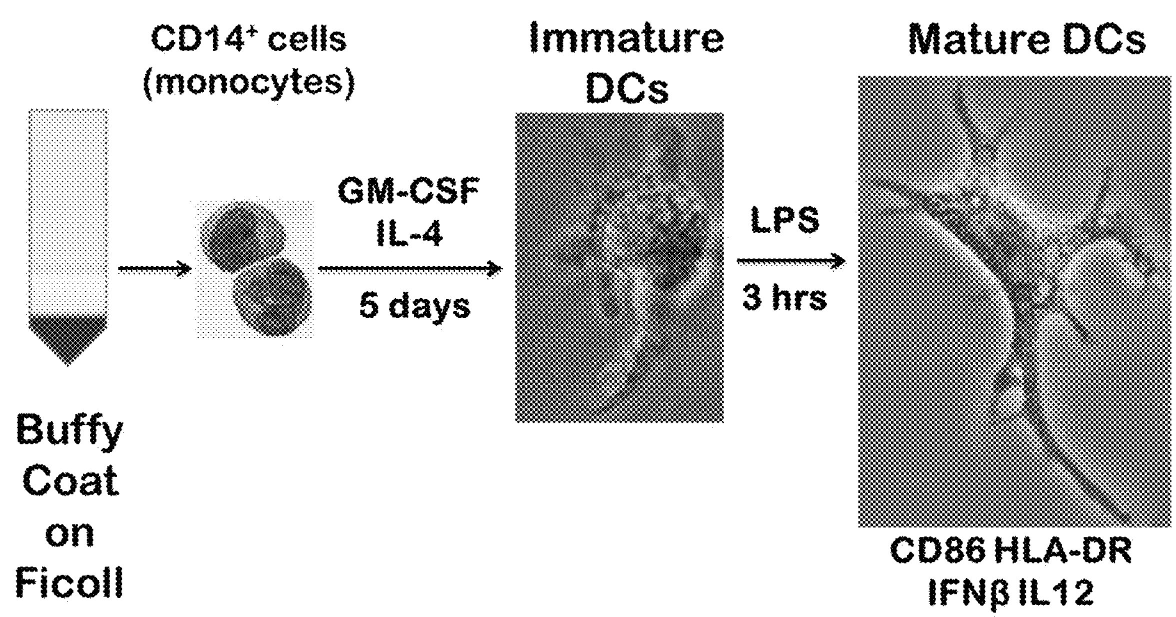
FIG. 3 depicts a schematic of the MDDC differentiation scheme.

MDDCs were differentiated from peripheral blood monocytes (PBMCs) for the purpose of studying DC transduction and viral gene knockdown (KD). Briefly, $CD14^+$ monocytes were isolated from buffy coats on Ficoll and incubated with GM-CSF and IL-4 to generate immature MDDCs. MDDC maturation was induced by the addition of LPS. FIG. 3 depicts a schematic of the MDDC differentiation scheme. MDDCs can be transduced with the HIV-1 viruses described herein at any stage of the differentiation process.

Example 3. In Vitro Challenge of MDDCs and $CD4^+$ T-Cells with HIV-1

Figure 4:
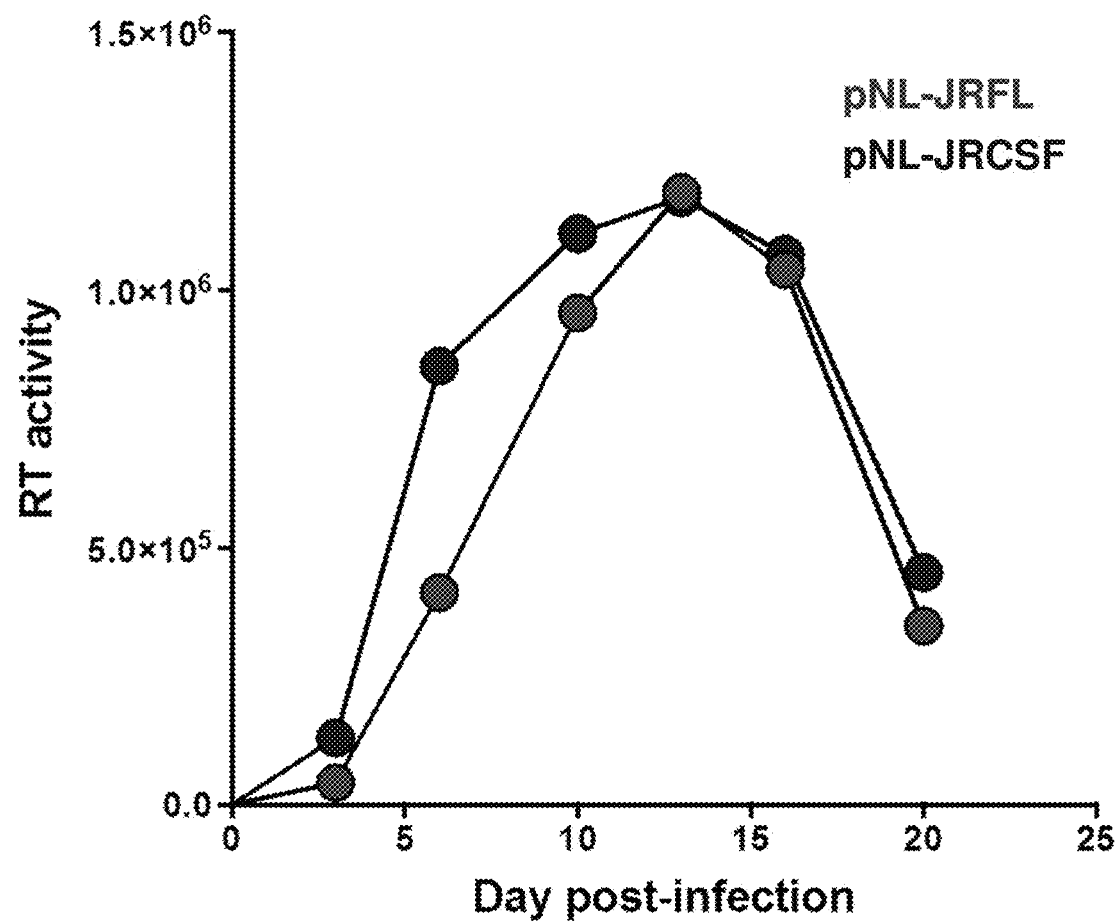
FIG. 4 depicts a graph showing the results of an in vitro challenge of primary $CD4^+$ T-cells with HIV-1 viruses generated with pNL-JRFL and pNL-JRCSF lentiviral plasmids.
Figure 5:
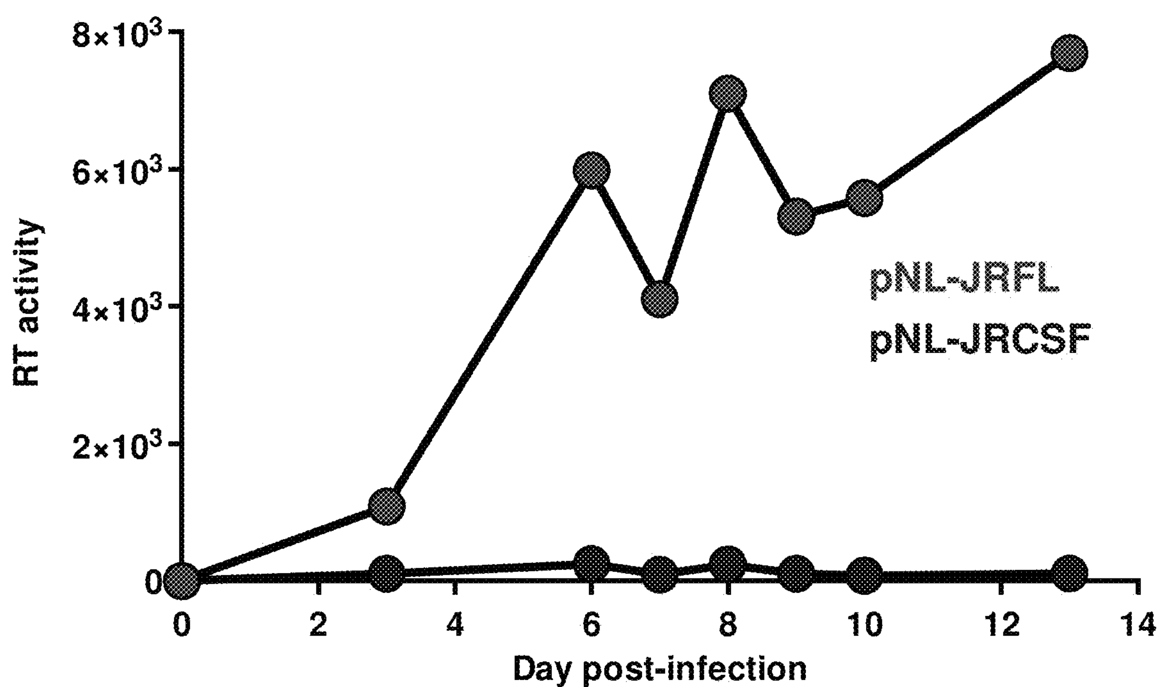
FIG. 5 depicts a graph showing the results of an in vitro challenge of primary MDDCs with HIV-1 viruses generated with pNL-JRFL and pNL-JRCSF lentiviral plasmids.

MDDCs were differentiated from PBMCs as described herein. Naïve primary $CD4^+$ T-cells were prepared by negative selection with magnetic beads (see Neagu et al., 2009, J. Clin. Invest.; 119:3035-3047, which is incorporated by reference herein in its entirety). MDDCs and $CD4^+$ T-cells were challenged in vitro with proviruses generated with the pNL-JRFL and pNL-JRCSF plasmids described herein. As shown in FIG. 4, in vitro challenge of primary $CD4^+$ T-cells with isogenic HIV-1 viruses that differ only in the composition of their respective envelope coat proteins demonstrated that pNLBN-JRCSF virus replicated at least as well as pNLBN-JRFL virus in T-cells. However, as shown in FIG. 5, in vitro challenge of MDDCs revealed that only the pNLBN-JRFL virus was capable of transducing MDDCs. These results were confirmed by FACS (p24 or GFP) and PCR (viral cDNA), and by testing the infectivity of the virion particles released from the DC cultures.

Example 4. NSG-BLT Transgenic Mice

Figure 6:
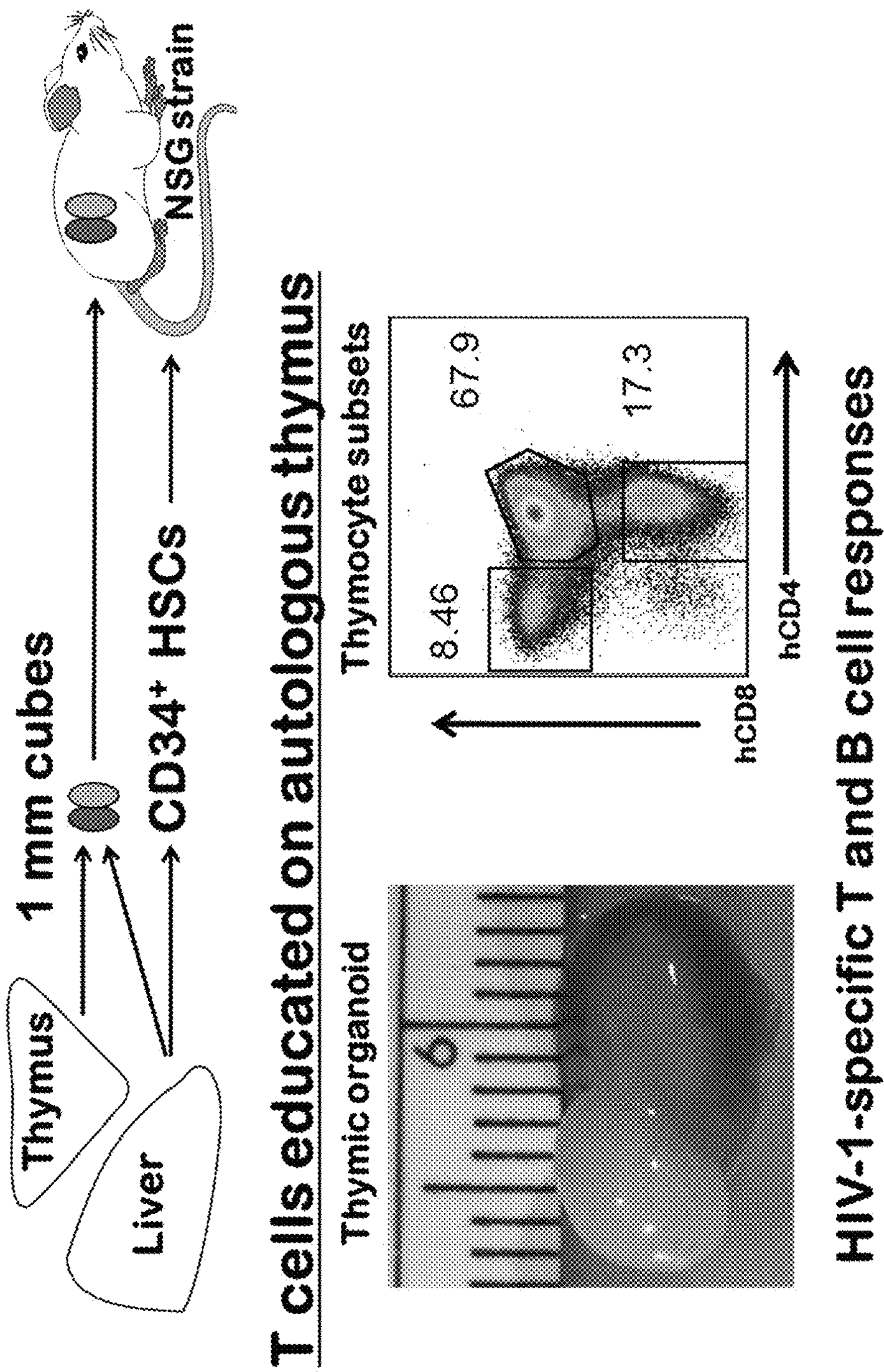
FIG. 6 depicts a schematic representation of the NSG-BLT mouse model.

The parental mouse strain, NOD-scid IL2Rg$^{null}$ (NSG), was developed by Leonard Schultz (see Shultz et al., 2005, J. Immunol.; 174:6477-6489, which is incorporated by reference herein in its entirety) and is now the world-wide standard strain for generating humanized mice. For the HLA-A2 mouse model, the transgenes HLA-A2 and huIL-7 (to enhance T cell responses), huBLyS/BAFF (to enhance human B cell responses), and huCSF-1 (to enhance APC development and function) were introduced into the NSG background (see Shultz et al., 2010, PNAS; 107:13022-13027; and Jaiswal et al., 2009, PLoS ONE; 4:e7251, which are each incorporated by reference herein in their entirety). The BLT model is generated by surgically implanting human fetal thymus and liver tissue under the kidney capsule followed by systemic injection of $CD34^+$ fetal liver cells (Tonomura et al., 2008, Blood; 111:4293-4296; Lan et al., 2006, Blood; 108:487-492; and Melkus et al., 2006. Nat. Med.; 12:1316-1322, which are each incorporated by reference herein in their entirety). Development of the xenograft is monitored by 10-color FACS of the peripheral blood for human lymphocyte subsets and other human hematopoietic lineages. The NSG-BLT model permits antigen-specific $CD4^+$ and $CD8^+$ T cell responses specific for HIV-1, as well as for other pathogens. FIG. 6 depicts a schematic representation of the NSG-BLT mouse model.

Example 5. In Vivo Challenge of NSG-BLT Transgenic Mice with HIV-1

Figure 7A:
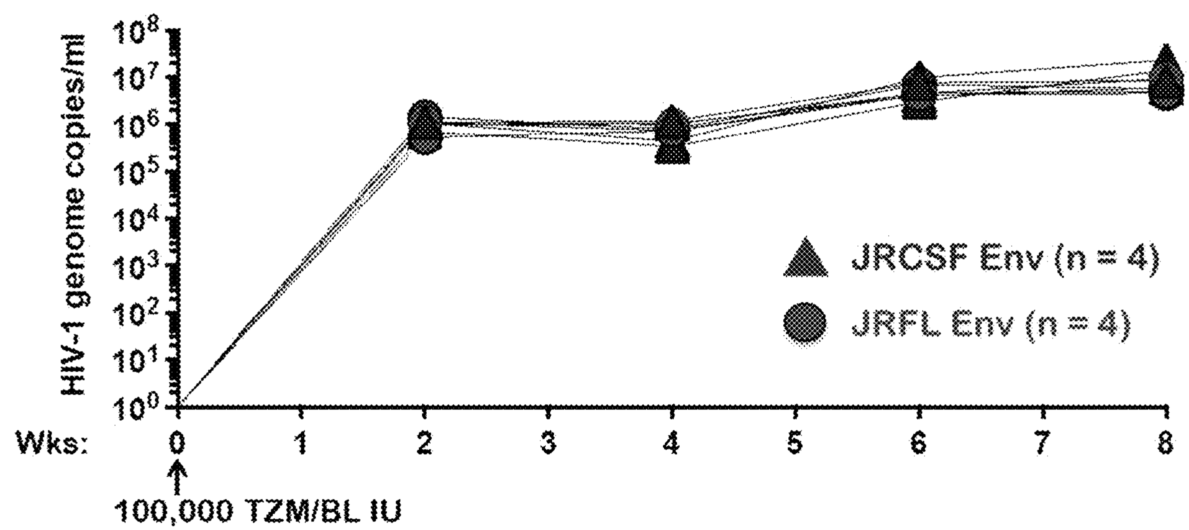
FIG. 7A depicts a graph showing the results of an in vivo challenge of NSG-BLT with HIV-1 viruses generated with pNL-JRFL and pNL-JRCSF lentiviral plasmids.
Figure 7B:
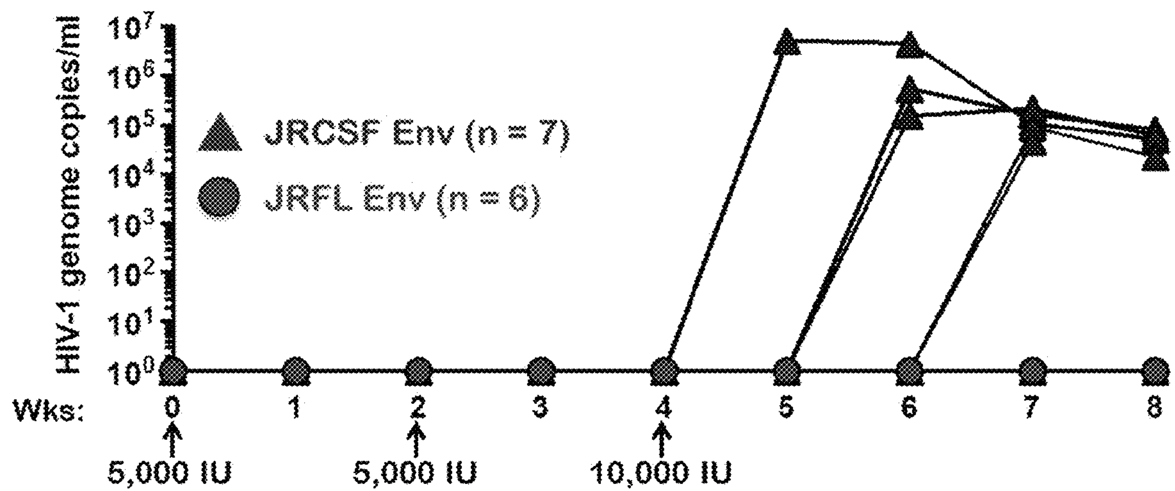
FIG. 7B depicts a graph showing the results of an in vivo challenge of NSG-BLT with isogenic HIV-1 viruses generated with pNL-JRFL and pNL-JRCSF lentiviral plasmids.
Figure 8:
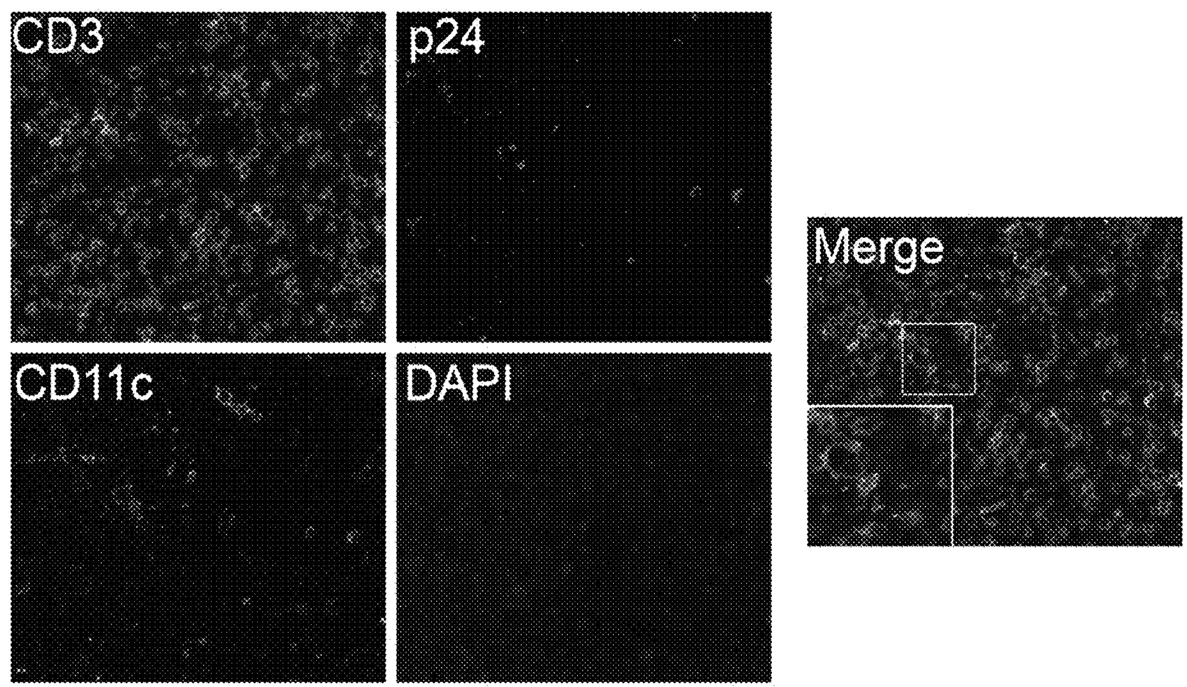
FIG. 8 depicts a fluorescent micrograph indicating the presence of HIV-1 infected DCs in virally-challenged NSG-BLT mice.
Figure 9:
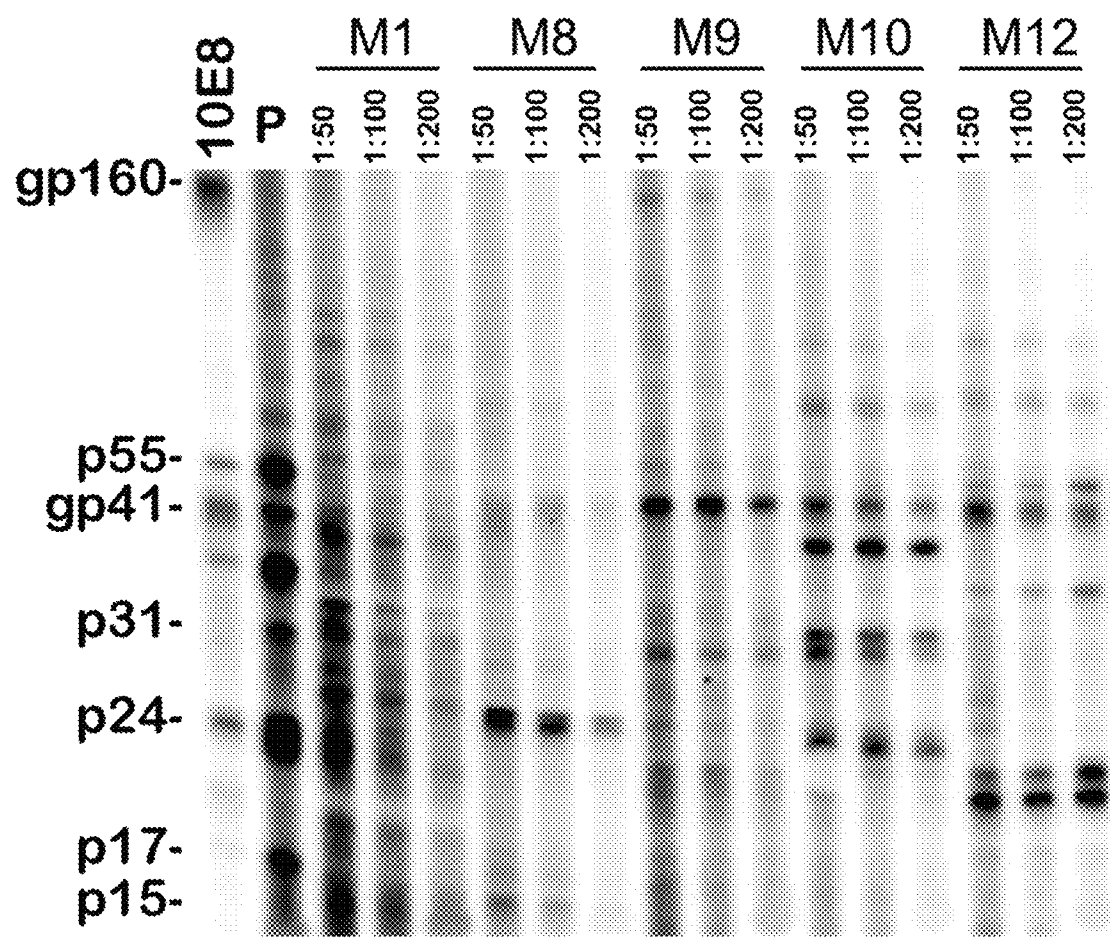
FIG. 9 depicts a Western blot demonstrating that several NSG-BLT mice infected with a JRFL pseudotyped recombinant HIV-1 virus generated human anti-HIV-1 IgG responses.

Though NSG-BLT mice generate antigen-specific antibody responses, they have poor class switching, and to date, anti-HIV-1 IgG responses have not been reported in these animals. Two separate cohorts of NSG-BLT mice (n=12 and 15) were challenged with two different stocks of recombinant virus on the pNL4-3 background; the first stock was pseudotyped with the JRFL env and the other with the JRCSF env. As shown in FIG. 7A, when mice were infected with 100,000 infective units (IU) at week 0, both cohorts demonstrated sustained infection at 2-8 weeks post-infection. All mice had viral loads between $10^5$ and $10^6$ HIV-1 genome copies per ml of mouse serum using as determined by RT-PCR. However, as shown in FIG. 7B, when challenged with lower doses of virus at weeks 0, 2, and 4, only the cohort infected with the JRCSF pseudotyped HIV-1 virus demonstrated sustained infection at weeks 4-8, while the cohort infected with the JRFL pseudotyped HIV-1 virus remained free of infection through week 8. As shown in FIG. 8, $CD3^+$, $CD11C^+$, $p24^+$ DCs were observed in mouse tissues, indicating that DCs had been transduced by the HIV-1 viruses. Many of the mice generated human anti-HIV-1 IgG responses, as confirmed by Western blot and shown in FIG. 9. As shown in Table 1 below, the cohort challenged with the JRFL pseudotyped HIV-1 virus generated a more robust anti-HIV-1 IgG response than the cohort infected with the JRCSF pseudotyped HIV-1 virus, and all of the JRFL cohort developed HIV-1 neutralizing antibodies compared to only one mouse in the JRCSF cohort. Similar results were observed regardless of whether the mice were challenged with virus by intraperitoneal, intrarectal, or intravaginal modes of administration.

TABLE 1

Antibody response of NSG-BLT mice challenged with HIV-1

| | JRFL | JRCSF |
|---|---|---|
| % mice with human anti-HIV-1 IgG | >90% | 38% |
| HIV-1 neutralizing Abs | 6/6 | 1/5 |

Example 6. Generation of Autologous Fetal Liver-Derived Dendritic Cells (FLDCs)

Figure 10:
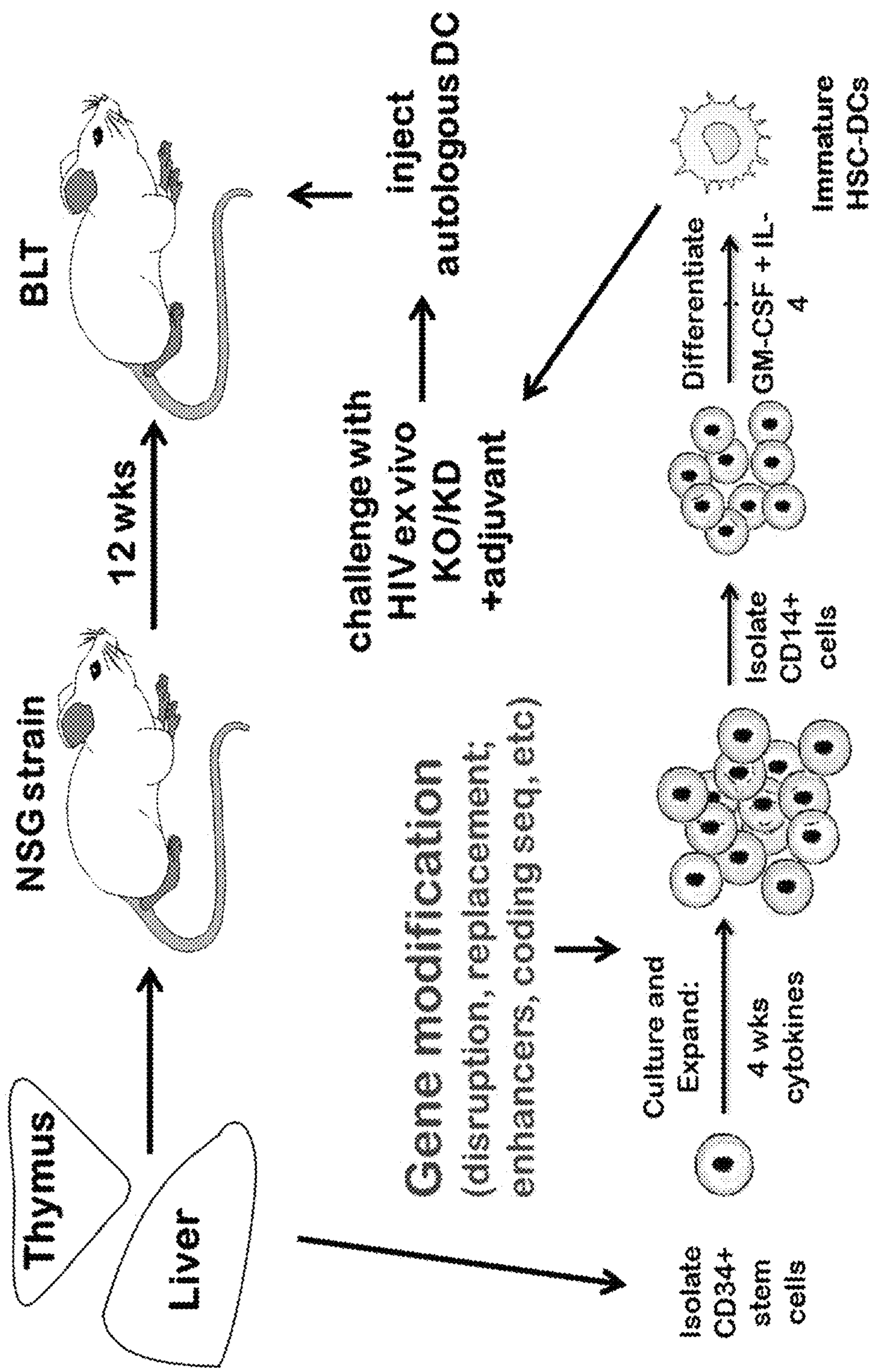
FIG. 10 depicts a schematic of the process for generating fetal liver derived dendritic cells (FLDCs).
Figure 11:
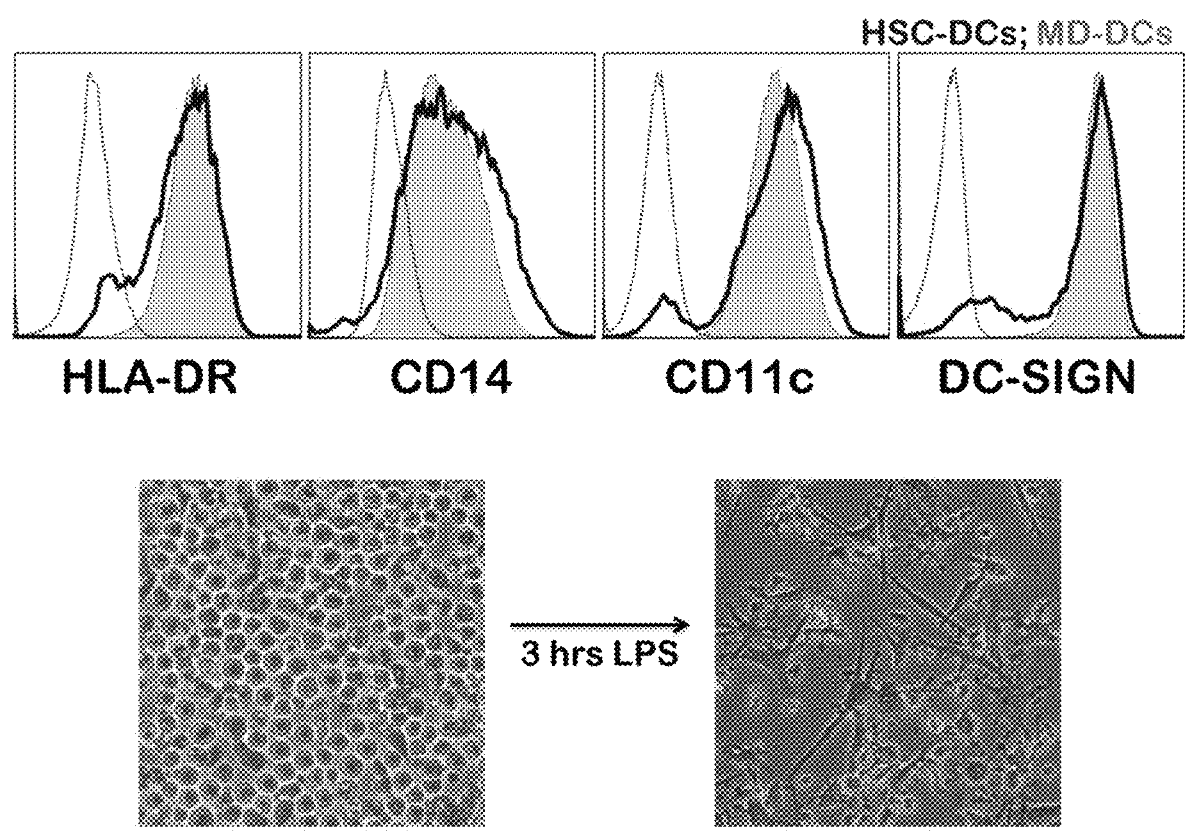
FIG. 11 depicts a micrographic image of FLDCs and a FACS histogram of FDLC markers.

In order to modify autologous DCs ex vivo for functional testing in humanized mice, DCs were generated from the same $CD34^+$ fetal liver cells that were used to reconstitute the BLT mice. To generate fetal liver derived DCs (FLDCs), mononuclear cells were harvested from a Ficoll-Hypaque gradient. $CD34^+$ cells were then enriched by two rounds of positive selection with Miltenyi beads, typically yielding cells that were >98% $CD34^+$. $CD34^+$ cells were plated in Nunc low cell binding plates ($10^5$ cells/plate) in supplemented RPMI (RPMI, 5% human $AB^+$ serum supplemented with GM-CSF and SCF). After 25 days, the cell number reached $10^9$ cells/plate, at which point the cells were re-plated in media containing GM-CSF and IL-4. FIG. 10 depicts a schematic of the process for generating FLDCs. As shown in FIG. 11, the population was indistinguishable from DCs generated from peripheral blood monocytes, as assessed by microscopy and flow cytometry (CD11C, CD14, CD11c, DC-SIGN) after one week of culture in the presence of GM-CSF and IL-4.

Example 7. The Role of Vpx in Lentiviral Replication

Figure 12:
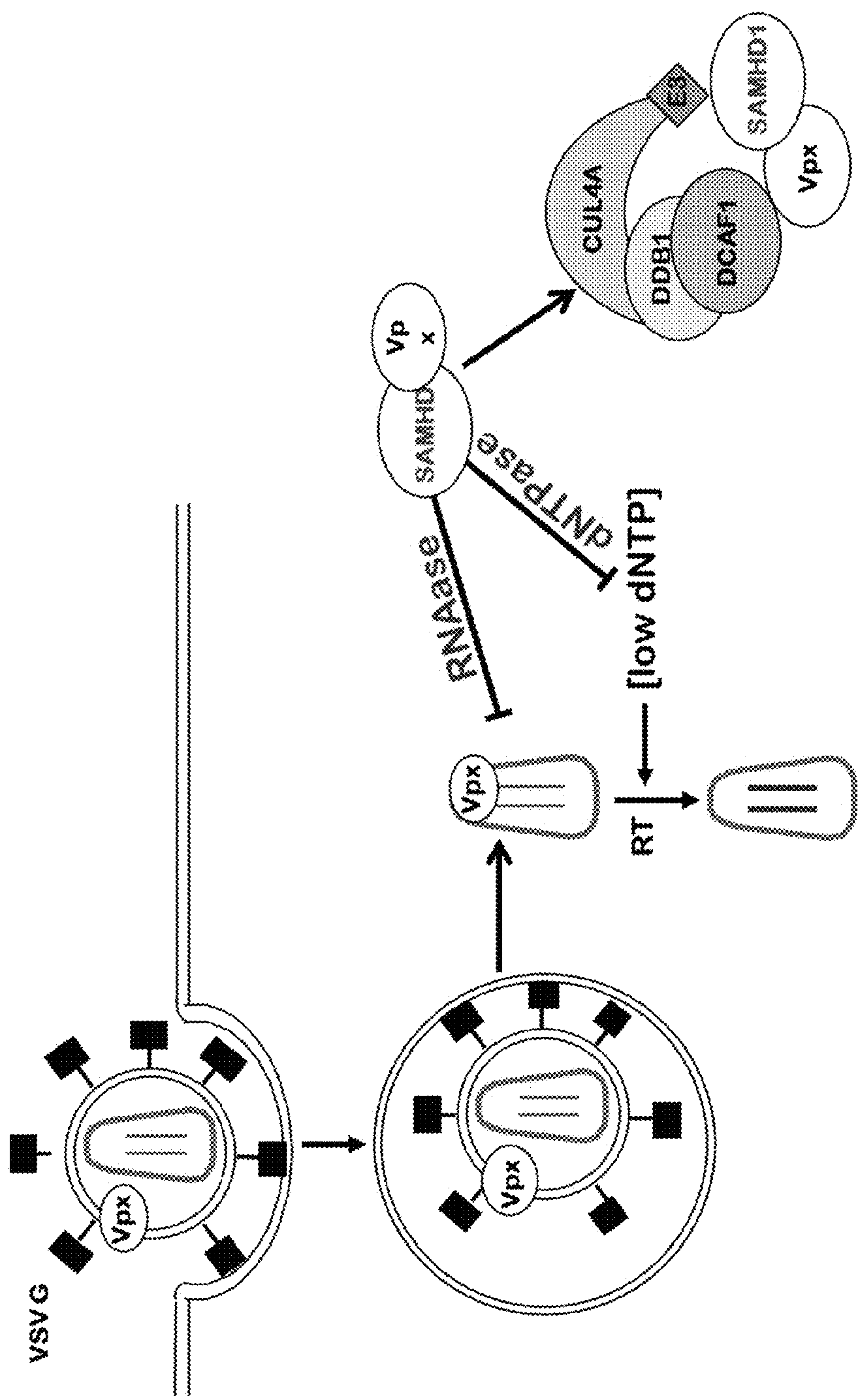
FIG. 12 depicts a schematic of the roles of SAMHD and Vpx in HIV-2 replication.

SAMHD1 is a triphosphohydrolase that blocks reverse transcription in DCs and other non-dividing cells by depleting dNTPs needed for HIV-1 reverse transcription. In addition, SAMHD1 has exonuclease activity that may contribute to the block in HIV-1 cDNA accumulation in DCs Viruses from the HIV-2/$SIV_{SM}$/$SIV_{MAC}$ lineage encode a protein called Vpx that binds SAMHD1 and recruits it to the DCAF1/DDB1/RBX1/CUL4A complex for ubiquitination and degradation. In contrast to infection with HIV-1, infection with HIV-2 rarely causes AIDS. Thus, by promoting replication within DCs, Vpx may increase the innate immune sensing of HIV-2, and thereby render more effective the acquired immunity targeting this virus. FIG. 12 depicts a schematic of the roles of SAMHD and Vpx in HIV-2 replication.

Figure 13:
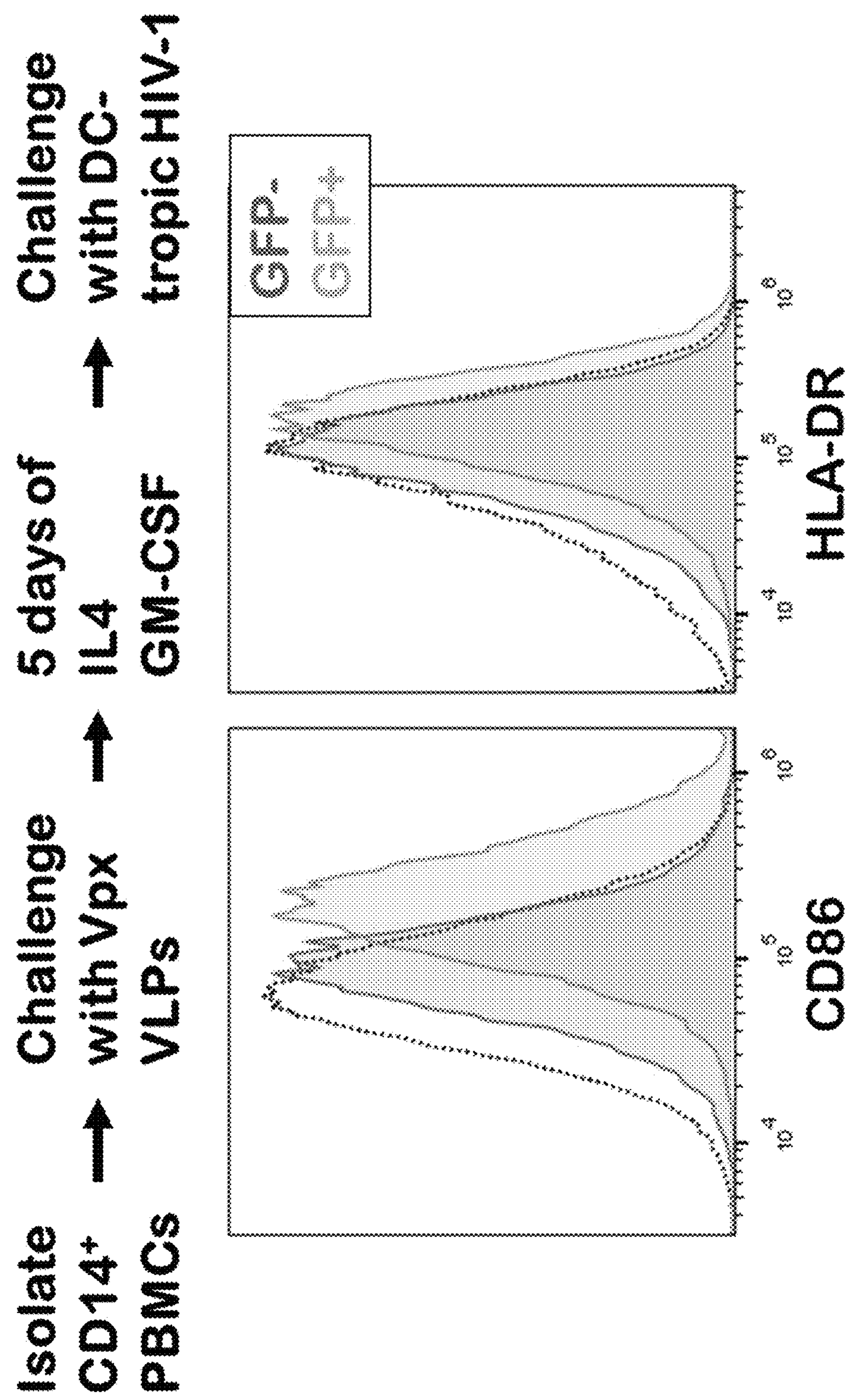
FIG. 13 depicts a FACS histogram showing that the Vpx provided in trans promotes the transduction of DCs by HIV-1.
Figure 14:
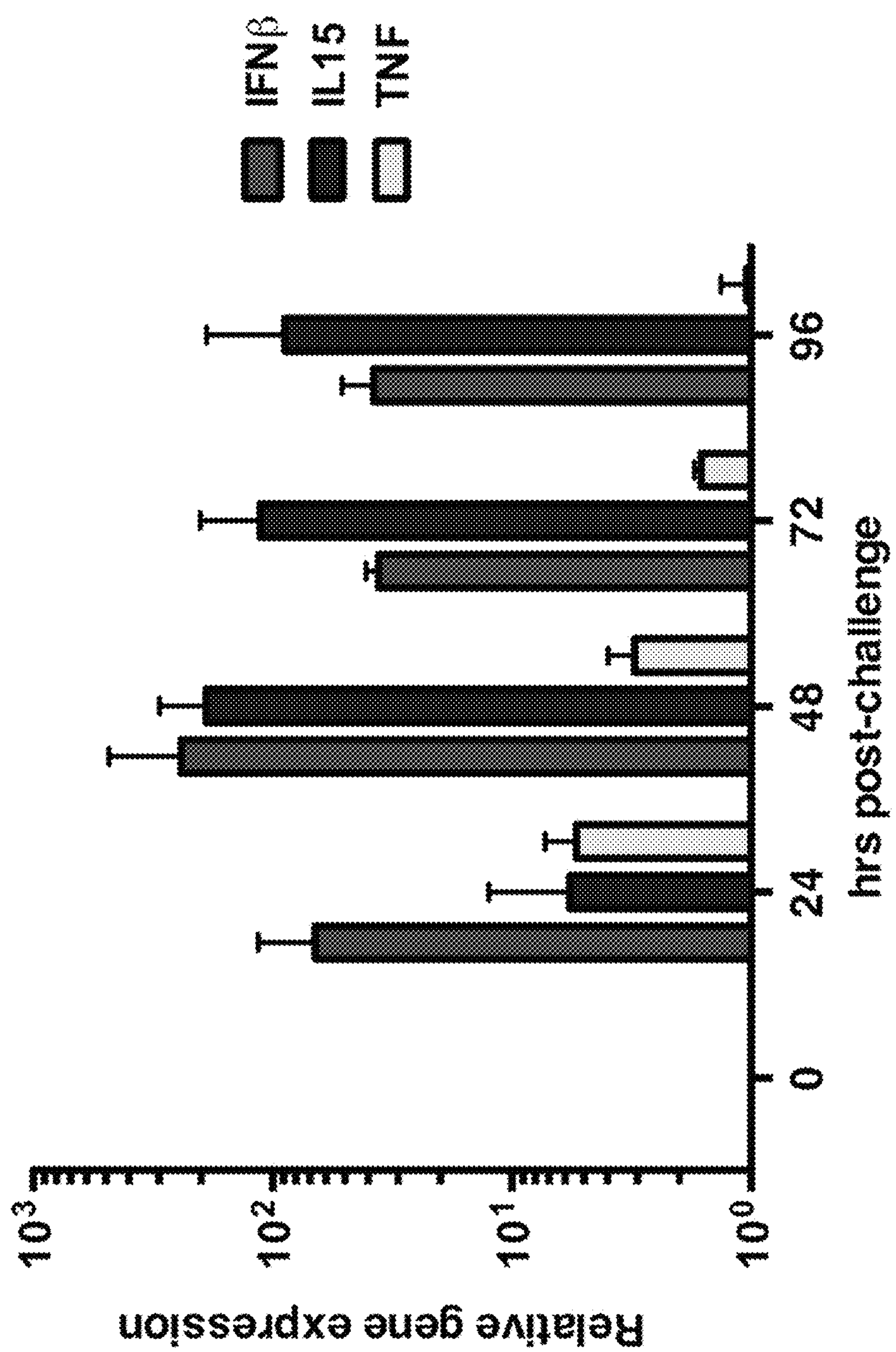
FIG. 14 depicts a bar graph showing that several cytokines indicative of an activated DC appeared up-regulated in DCs transduced by HIV-1 and Vpx.
Figure 15:
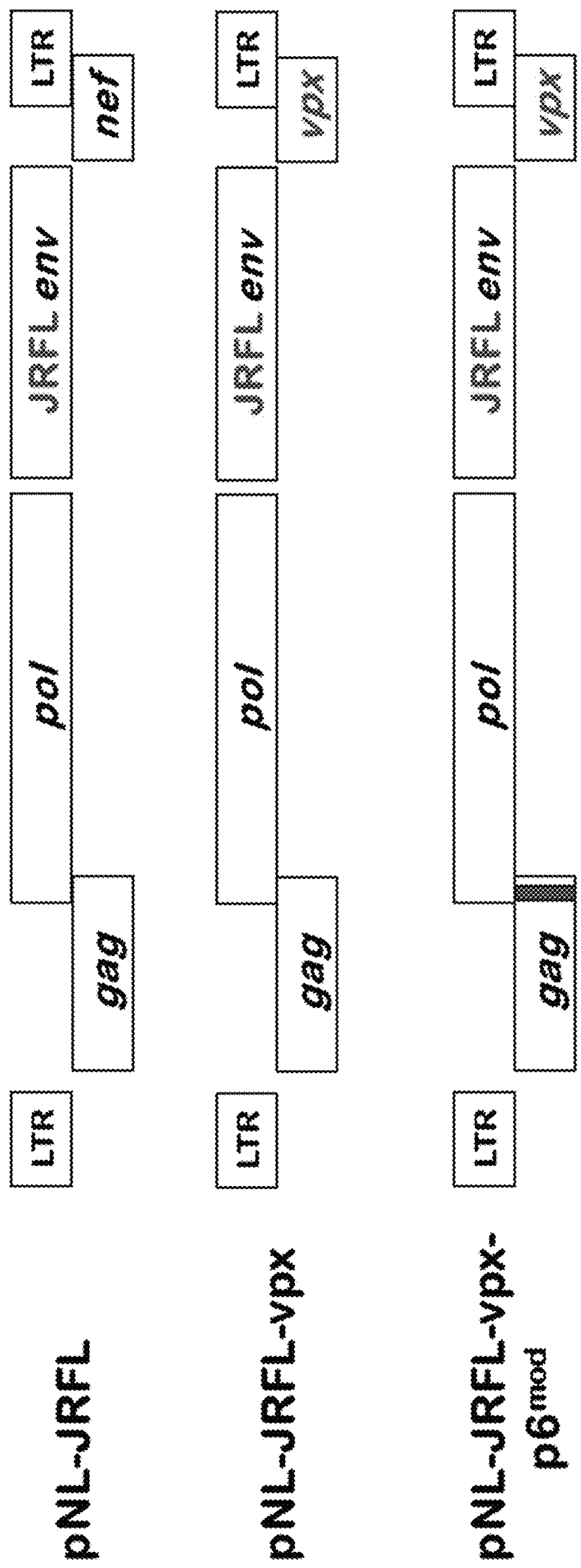
FIG. 15 depicts a schematic of the one-plasmid lentiviral system for generating pseudotyped lentivirus containing Vpx or Vpx and a modified p6.
Figure 16:
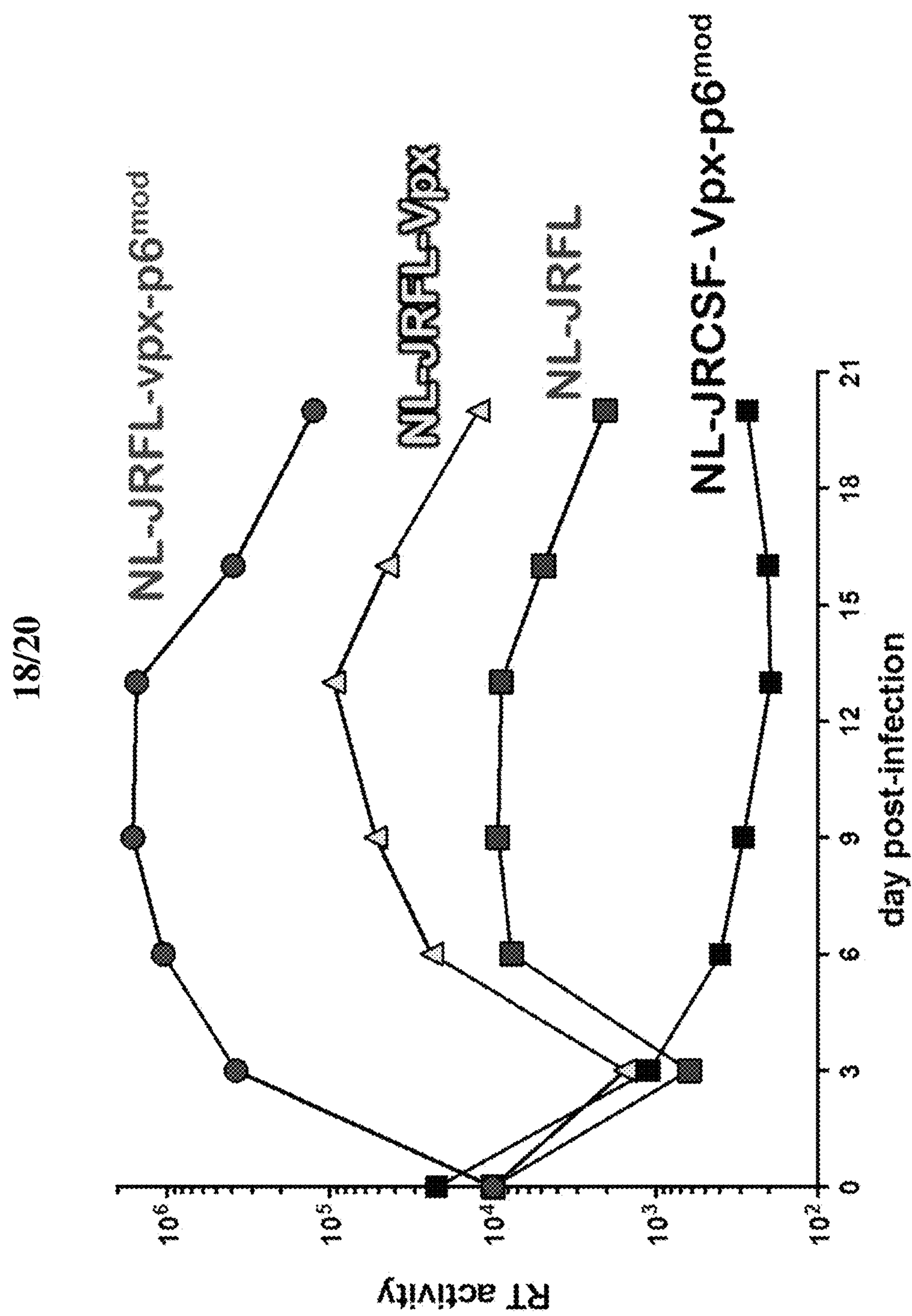
FIG. 16 depicts a line graph showing that the addition of Vpx and the Vpx+p6 modification increased HIV-1 virus transcription over a 21 day period.

HIV-1 does not encode Vpx. However, Vpx provided in trans promotes the transduction of DCs by HIV-1 (see FIG. 13). Furthermore, several cytokines indicative of an activated DC appeared up-regulated in DCs transduced by HIV-1 and Vpx (see FIG. 14). Accordingly, several HIV-1 proviral plasmids were engineered to further study the effect of Vpx on DC transduction when Vpx is provided in cis (see FIG. 15). One plasmid was contained Vpx substituted for nef (SEQ ID NO:8). Another plasmid contained the Vpx substitution and a p6 modification of the gag gene which better incorporates Vpx into the HIV-1 virion (SEQ ID NO:9). As shown in FIG. 16, the addition of Vpx and the Vpx+p6 modification increased virus transcription over a 21 day period.

Example 8. Eliciting Human IgG Against Heterologous Proteins

Figure 17:
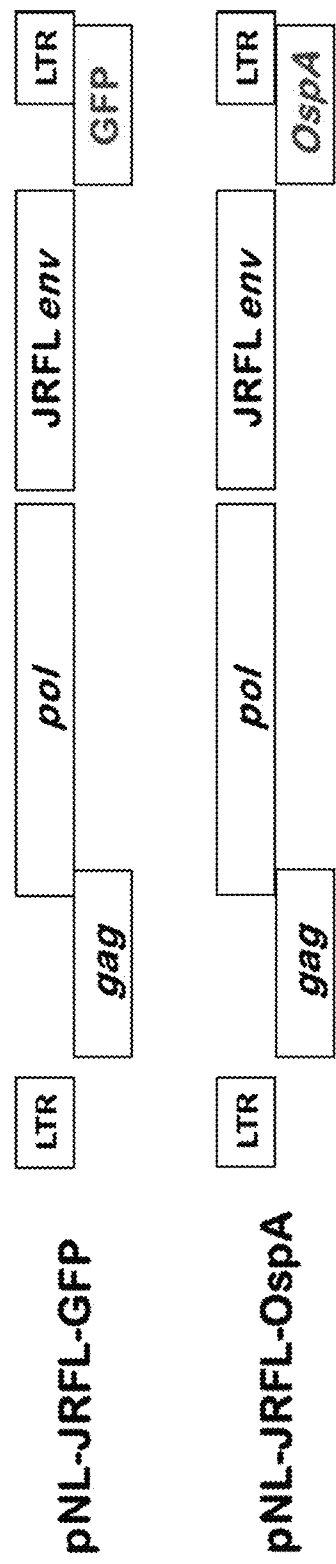
FIG. 17 depicts a schematic of the one-plasmid lentiviral system for generating pseudotyped lentivirus containing a heterologous protein.
Figure 18:
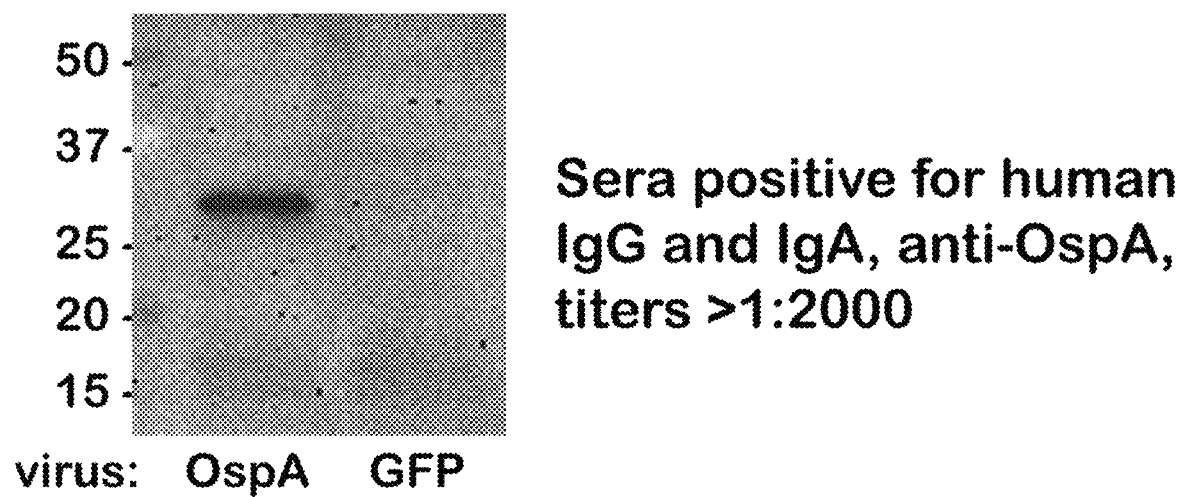
FIG. 18 depicts a PAGE gel showing that NSG-BLT transgenic mice generated human IgG and IgA antibodies against OspA upon challenge with the engineered viruses.

To determine whether the technology disclosed herein could be used to generate human IgG antibodies against heterologous proteins from viruses or diseases other than HIV-1, the nef gene was replaced from the pNLBN-JRFL proviral plasmid with either GFP (SEQ ID NO:10) or OspA (SEQ ID NO:11) from the Lyme disease spirochete (see FIG. 17). HIV-1 viruses were generated as described herein and NSG-BLT transgenic mice were challenged with the viruses. As shown in FIG. 18, NSG-BLT transgenic mice generated human IgG and IgA antibodies against OspA upon challenge with the engineered viruses. Accordingly, the instant technology provides a needed platform for generating human antibodies against a variety of disease antigens.

I claim:

1. A method of producing human antibodies or antibody fragments thereof comprising the steps of:

a) administering a virus or virus-like particle to a non-human mammal comprising heterologous human immune cells, wherein the virus or virus-like particle comprises a nucleotide sequence encoding an HIV-1 env gene as set forth in SEQ ID NO:15, and wherein the non-human mammal is a transgenic mouse that lacks mature lymphocytes and natural killer (NK) cells and comprises one or more engrafted human tissues selected from the group consisting of human fetal thymus tissue, human fetal liver tissue, and human CD34+ fetal liver cells; and b) isolating a population of mammalian immunoglobulin-producing cells from the non-human mammal, thereby producing the human antibodies or antibody fragments thereof, wherein the human antibodies are anti-HIV-1 antibodies.

2. The method of claim 1, further comprising the steps of:

c) reverse transcribing VH and VL mRNA of the cell population into a pooled population of VH and VL cDNA sequences;

d) cloning the pooled population of DNA fragments into expression vectors; and e) expressing the cloned DNA fragments, thereby producing the antibodies or fragments thereof;

or c) fusing the immunoglobulin-producing cells with myeloma cells to form parental hybridoma cells; and d) culturing the hybridoma cells, thereby producing the antibodies or antibody fragments thereof;

or c) fusing the immunoglobulin-producing cells with myeloma cells to form a population of parental hybridoma cells;

d) culturing the population of hybridoma cells;

e) reverse transcribing VH and VL mRNA of the cell population into a pooled population of VH and VL cDNA sequences;

f) cloning the pooled population of DNA fragments into expression vectors and amplifying the cloned expression vectors;

g) selecting a subpopulation of expression vectors which encodes antibodies or antibody fragments directed against a virus or virus-like particle encoded protein; and h) and amplifying the subpopulation selected, thereby producing the antibodies or antibody fragments thereof.

3. The method of claim 1, wherein the transgenic mouse is a NOD-scid IL2Rγnull mouse strain.

4. The method of claim 1, wherein the human antibodies or antibody fragments thereof are anti-HIV-1 neutralizing antibodies.

5. The method of claim 1, wherein the nucleotide sequence further encodes a heterologous protein.

6. The method of claim 5, wherein the heterologous protein is the outer surface protein A (OspA) of the spirochete *Borrelia burgdorferi*.

7. The method of claim 5, wherein the human antibodies are against the heterologous protein.

8. The method of claim 6, wherein the human antibodies are anti-OspA antibodies.

9. The method of claim 3, wherein the human fetal thymus tissue and/or human fetal liver tissue is engrafted under the mouse kidney capsule.

10. The method of claim 3, wherein the human CD34+ fetal liver cells are engrafted systemically.

* * * * *

SEQUENCE LISTING

```
<160> NUMBER OF SEQ ID NOS: 19

<210> SEQ ID NO 1
<211> LENGTH: 14825
<212> TYPE: DNA
<213> ORGANISM: Human immunodeficiency virus type 1

<400> SEQUENCE: 1

tggaagggct aatttggtcc caaaaaagac aagagatcct tgatctgtgg atctaccaca     60

cacaaggcta cttccctgat tggcagaact acacaccagg gccagggatc agatatccac    120

tgacctttgg atggtgcttc aagttagtac cagttgaacc agagcaagta gaagaggcca    180

atgaaggaga gaacaacagc ttgttacacc ctatgagcca gcatgggatg gaggacccgg    240

agggagaagt attagtgtgg aagtttgaca gcctcctagc atttcgtcac atggcccgag    300

agctgcatcc ggagtactac aaagactgct gacatcgagc tttctacaag ggactttccg    360

ctggggactt tccagggagg tgtggcctgg gcgggactgg ggagtggcga gccctcagat    420

gctacatata agcagctgct ttttgcctgt actgggtctc tctggttaga ccagatctga    480

gcctgggagc tctctggcta actagggaac ccactgctta agcctcaata aagcttgcct    540

tgagtgctca aagtagtgtg tgcccgtctg ttgtgtgact ctggtaacta gagatccctc    600

agaccctttt agtcagtgtg gaaaatctct agcagtggcg cccgaacagg gacttgaaag    660

cgaaagtaaa gccagaggag atctctcgac gcaggactcg gcttgctgaa gcgcgcacgg    720

caagaggcga ggggcggcga ctggtgagta cgccaaaaat tttgactagc ggaggctaga    780

aggagagaga tgggtgcgag agcgtcggta ttaagcgggg gagaattaga taaatgggaa    840

aaaattcggt taaggccagg gggaaagaaa caatataaac taaaacatat agtatgggca    900

agcagggagc tagaacgatt cgcagttaat cctggccttt tagagacatc agaaggctgt    960
```

```
agacaaatac tgggacagct acaaccatcc cttcagacag gatcagaaga acttagatca   1020
ttatataata caatagcagt cctctattgt gtgcatcaaa ggatagatgt aaaagacacc   1080
aaggaagcct tagataagat agaggaagag caaaacaaaa gtaagaaaaa ggcacagcaa   1140
gcagcagctg acacaggaaa caacagccag gtcagccaaa attaccctat agtgcagaac   1200
ctccaggggc aaatggtaca tcaggccata tcacctagaa ctttaaatgc atgggtaaaa   1260
gtagtagaag agaaggcttt cagcccagaa gtaataccca tgttttcagc attatcagaa   1320
ggagccaccc cacaagattt aaataccatg ctaaacacag tgggggggaca tcaagcagcc   1380
atgcaaatgt taaaagagac catcaatgag gaagctgcag aatgggatag attgcatcca   1440
gtgcatgcag ggcctattgc accaggccag atgagagaac caaggggaag tgacatagca   1500
ggaactacta gtacccttca ggaacaaata ggatggatga cacataatcc acctatccca   1560
gtaggagaaa tctataaaag atggataatc ctgggattaa ataaaatagt aagaatgtat   1620
agccctacca gcattctgga cataagacaa ggaccaaagg aaccctttag agactatgta   1680
gaccgattct ataaaactct aagagccgag caagcttcac aagaggtaaa aaattggatg   1740
acagaaacct tgttggtcca aaatgcgaac ccagattgta agactatttt aaaagcattg   1800
ggaccaggag cgacactaga agaaatgatg acagcatgtc agggagtggg gggacccggc   1860
cataaagcaa gagttttggc tgaagcaatg agccaagtaa caaatccagc taccataatg   1920
atacagaaag gcaattttag gaaccaaaga aagactgtta agtgtttcaa ttgtggcaaa   1980
gaagggcaca tagccaaaaa ttgcagggcc cctaggaaaa agggctgttg gaaatgtgga   2040
aaggaaggac accaaatgaa agattgtact gagagacagg ctaatttttt agggaagatc   2100
tggccttccc acaagggaag gccagggaat tttcttcaga gcagaccaga gccaacagcc   2160
ccaccagaag agagcttcag gtttggggaa gagacaacaa ctccctctca gaagcaggag   2220
ccgatagaca aggaactgta tcctttagct tccctcagat cactctttgg cagcgacccc   2280
tcgtcacaat aaagataggg gggcaattaa aggaagctct attagataca ggagcagatg   2340
atacagtatt agaagaaatg aatttgccag gaagatggaa accaaaaatg atagggggaa   2400
ttggaggttt tatcaaagta agacagtatg atcagatact catagaaatc tgcggacata   2460
aagctatagg tacagtatta gtaggaccta cacctgtcaa cataattgga agaaatctgt   2520
tgactcagat tggctgcact ttaaattttc ccattagtcc tattgagact gtaccagtaa   2580
aattaaagcc aggaatggat ggcccaaaag ttaaacaatg gccattgaca gaagaaaaaa   2640
taaaagcatt agtagaaatt tgtacagaaa tggaaaagga aggaaaaatt tcaaaaattg   2700
ggcctgaaaa tccatacaat actccagtat ttgccataaa gaaaaaagac agtactaaat   2760
ggagaaaatt agtagatttc agagaactta ataagagaac tcaagatttc tgggaagttc   2820
aattaggaat accacatcct gcagggttaa aacagaaaaa atcagtaaca gtactggatg   2880
tgggcgatgc atatttttca gttcccttag ataaagactt caggaagtat actgcattta   2940
ccatacctag tataaacaat gagacaccag ggattagata tcagtacaat gtgcttccac   3000
agggatggaa aggatcacca gcaatattcc agtgtagcat gacaaaaatc ttagagcctt   3060
ttagaaaaca aaatccagac atagtcatct atcaatacat ggatgatttg tatgtaggat   3120
ctgacttaga aatagggcag catagaacaa aaatagagga actgagacaa catctgttga   3180
ggtggggatt taccacacca gacaaaaaac atcagaaaga acctccattc ctttggatgg   3240
gttatgaact ccatcctgat aaatggacag tacagcctat agtgctgcca gaaaaggaca   3300
```

gctggactgt caatgacata cagaaattag tgggaaaatt gaattgggca agtcagattt 3360
atgcagggat taaagtaagg caattatgta aacttcttag gggaaccaaa gcactaacag 3420
aagtagtacc actaacagaa gaagcagagc tagaactggc agaaaacagg gagattctaa 3480
aagaaccggt acatggagtg tattatgacc catcaaaaga cttaatagca gaaatacaga 3540
agcaggggca aggccaatgg acatatcaaa tttatcaaga gccatttaaa aatctgaaaa 3600
caggaaagta tgcaagaatg aagggtgccc acactaatga tgtgaaacaa ttaacagagg 3660
cagtacaaaa aatagccaca gaaagcatag taatatgggg aaagactcct aaatttaaat 3720
tacccataca aaaggaaaca tgggaagcat ggtggacaga gtattggcaa gccacctgga 3780
ttcctgagtg ggagtttgtc aatacccctc ccttagtgaa gttatggtac cagttagaga 3840
aagaacccat aataggagca gaaactttct atgtagatgg ggcagccaat agggaaacta 3900
aattaggaaa agcaggatat gtaactgaca gaggaagaca aaaagttgtc cccctaacgg 3960
acacaacaaa tcagaagact gagttacaag caattcatct agctttgcag gattcgggat 4020
tagaagtaaa catagtgaca gactcacaat atgcattggg aatcattcaa gcacaaccag 4080
ataagagtga atcagagtta gtcagtcaaa taatagagca gttaataaaa aaggaaaaag 4140
tctacctggc atgggtacca gcacacaaag gaattggagg aaatgaacaa gtagataaat 4200
tggtcagtgc tggaatcagg aaagtactat ttttagatgg aatagataag gcccaagaag 4260
aacatgagaa atatcacagt aattggagag caatggctag tgattttaac ctaccacctg 4320
tagtagcaaa agaaatagta gccagctgtg ataaatgtca gctaaaaggg gaagccatgc 4380
atggacaagt agactgtagc ccaggaatat ggcagctaga ttgtacacat ttagaaggaa 4440
aagttatctt ggtagcagtt catgtagcca gtggatatat agaagcagaa gtaattccag 4500
cagagacagg gcaagaaaca gcatacttcc tcttaaaatt agcaggaaga tggccagtaa 4560
aaacagtaca tacagacaat ggcagcaatt tcaccagtac tacagttaag gccgcctgtt 4620
ggtgggcggg gatcaagcag gaatttggca ttccctacaa tccccaaagt caaggagtaa 4680
tagaatctat gaataaagaa ttaaagaaaa ttataggaca ggtaagagat caggctgaac 4740
atcttaagac agcagtacaa atggcagtat tcatccacaa ttttaaaaga aaagggggga 4800
ttggggggta cagtgcaggg gaaagaatag tagacataat agcaacagac atacaaacta 4860
aagaattaca aaaacaaatt acaaaaattc aaaattttcg ggtttattac agggacagca 4920
gagatccagt ttggaaagga ccagcaaagc tcctctggaa aggtgaaggg gcagtagtaa 4980
tacaagataa tagtgacata aaagtagtgc caagaagaaa agcaaagatc atcagggatt 5040
atggaaaaca gatggcaggt gatgattgtg tggcaagtag acaggatgag gattaacaca 5100
tggaaaagat tagtaaaaca ccatatgtat atttcaagga aagctaagga ctggttttat 5160
agacatcact atgaaagtac taatccaaaa ataagttcag aagtacacat cccactaggg 5220
gatgctaaat tagtaataac aacatattgg ggtctgcata caggagaaag agactggcat 5280
ttgggtcagg gagtctccat agaatggagg aaaaagagat atagcacaca agtagaccct 5340
gacctagcag accaactaat tcatctgcac tattttgatt gtttttcaga atctgctata 5400
agaaatacca tattaggacg tatagttagt cctaggtgtg aatatcaagc aggacataac 5460
aaggtaggat ctctacagta cttggcacta gcagcattaa taaaaccaaa acagataaag 5520
ccacctttgc ctagtgttag gaaactgaca gaggacagat ggaacaagcc ccagaagacc 5580
aagggccaca gagggagcca tacaatgaat ggacactaga gcttttagag gaacttaaga 5640
gtgaagctgt tagacatttt cctaggatat ggctccataa cttaggacaa catatctatg 5700

-continued

```
aaacttacgg ggatacttgg gcaggagtgg aagccataat aagaattctg caacaactgc   5760
tgtttatcca tttcagaatt gggtgtcgac atagcagaat aggcgttact cgacagagga   5820
gagcaagaaa tggagccagt agatcctaga ctagagccct ggaagcatcc aggaagtcag   5880
cctaaaactg cttgtaccaa ttgctattgt aaaaagtgtt gctttcattg ccaagtttgt   5940
ttcatgacaa aagccttagg catctcctat ggcaggaaga agcggagaca gcgacgaaga   6000
gctcatcaga acagtcagac tcatcaagct tctctatcaa agcagtaagt agtacatgta   6060
atgcaaccta taatagtagc aatagtagca ttagtagtag caataataat agcaatagtt   6120
gtgtggtcca tagtaatcat agaatatagg aaaatattaa gacaaagaaa aatagacagg   6180
ttaattgata gactaataga aagagcagaa gacagtggca atgagagtga aggagaagta   6240
tcagcacttg tggagatggg ggtggaaatg gggcaccatg ctccttggga tattgatgat   6300
ctgtagtgct acagaaaaat tgtgggtcac agtctattat ggggtacctg tgtggaagga   6360
agcaaccacc actctatttt gtgcatcaga tgctaaagca tatgatacag aggtacataa   6420
tgtttgggcc acacatgcct gtgtacccac agaccccaac ccacaagaag tagtattggt   6480
aaatgtgaca gaaaatttta acatgtggaa aaatgacatg gtagaacaga tgcatgagga   6540
tataatcagt ttatgggatc aaagcctaaa gccatgtgta aaattaaccc cactctgtgt   6600
tagtttaaag tgcactgatt tgaagaatga tactaatacc aatagtagta gcgggagaat   6660
gataatggag aaaggagaga taaaaaactg ctctttcaat atcagcacaa gcataagaga   6720
taaggtgcag aaagaatatg cattctttta taaacttgat atagtaccaa tagataatac   6780
cagctatagg ttgataagtt gtaacacctc agtcattaca caggcctgtc caaaggtatc   6840
ctttgagcca attcccatac attattgtgc cccggctggt tttgcgattc taaaatgtaa   6900
taataagacg ttcaatggaa caggaccatg tacaaatgtc agcacagtac aatgtacaca   6960
tggaatcagg ccagtagtat caactcaact gctgttaaat ggcagtctag cagaagaaga   7020
tgtagtaatt agatctgcca atttcacaga caatgctaaa accataatag tacagctgaa   7080
cacatctgta gaaattaatt gtacaagacc caacaacaat acaagaaaaa gtatccgtat   7140
ccagagggga ccagggagag catttgttac aataggaaaa ataggaaata tgagacaagc   7200
acattgtaac attagtagag caaaatggaa tgccacttta aaacagatag ctagcaaatt   7260
aagagaacaa tttggaaata ataaaacaat aatctttaag caatcctcag gaggggaccc   7320
agaaattgta acgcacagtt ttaattgtgg aggggaattt ttctactgta attcaacaca   7380
actgtttaat agtacttggt ttaatagtac ttggagtact gaagggtcaa ataacactga   7440
aggaagtgac acaatcacac tcccatgcag aataaaacaa tttataaaca tgtggcagga   7500
agtaggaaaa gcaatgtatg cccctcccat cagtggacaa attagatgtt catcaaatat   7560
tactgggctg ctattaacaa gagatggtgg taataacaac aatgggtccg agatcttcag   7620
acctggagga ggcgatatga gggacaattg gagaagtgaa ttatataaat ataaagtagt   7680
aaaaattgaa ccattaggag tagcacccac caaggcaaag agaagagtgg tgcagagaga   7740
aaaaagagca gtgggaatag gagctttgtt ccttgggttc ttgggagcag caggaagcac   7800
tatgggcgca gcgtcaatga cgctgacggt acaggccaga caattattgt ctgatatagt   7860
gcagcagcag aacaatttgc tgagggctat tgaggcgcaa cagcatctgt tgcaactcac   7920
agtctggggc atcaaacagc tccaggcaag aatcctggct gtggaaagat acctaaagga   7980
tcaacagctc ctggggattt ggggttgctc tggaaaactc atttgcacca ctgctgtgcc   8040
```

```
ttggaatgct agttggagta ataaatctct ggaacagatt tggaataaca tgacctggat   8100
ggagtgggac agagaaatta acaattacac aagcttaata cactccttaa ttgaagaatc   8160
gcaaaaccag caagaaaaga atgaacaaga attattggaa ttagataaat gggcaagttt   8220
gtggaattgg tttaacataa caaattggct gtggtatata aaattattca taatgatagt   8280
aggaggcttg gtaggtttaa gaatagtttt tgctgtactt tctatagtga atagagttag   8340
gcagggatat tcaccattat cgtttcagac ccacctccca atcccgaggg gacccgacag   8400
gcccgaagga atagaagaag aaggtggaga gagagacaga gacagatcca ttcgattagt   8460
gaacggatcc ttagcactta tctgggacga tctgcggagc ctgtgcctct tcagctacca   8520
ccgcttgaga gacttactct tgattgtaac gaggattgtg gaacttctgg gacgcagggg   8580
gtgggaagcc ctcaaatatt ggtggaatct cctacagtat tggagtcagg aactaaagaa   8640
tagtgctgtt aacttgctca atgccacagc catagcagta gctgagggga cagatagggt   8700
tatagaagta ttacaagcag cttatagagc tattcgccac atacctagaa gaataagaca   8760
gggcttggaa aggattttgc tataagatgg gtggcaagtg gtcaaaaagt agtgtgattg   8820
gatggcctgc tgtaagggaa agaatgagac gagctgagcc agcagcagat ggggtgggag   8880
cagtatctcg agacctagaa aaacatggag caatcacaag tagcaataca gcagctaaca   8940
atgctgcttg tgcctggcta gaagcacaag aggaggaaga ggtgggtttt ccagtcacac   9000
ctcaggtacc tttaagacca atgacttaca aggcagctgt agatcttagc cactttttaa   9060
aagaaaaggg gggactggaa gggctaattc actcccaaag aagacaagat atccttgatc   9120
tgtggatcta ccacacacaa ggctacttcc ctgattggca gaactacaca ccagggccag   9180
gggtcagata tccactgacc tttggatggt gctacaagct agtaccagtt gagccagata   9240
aggtagaaga ggccaataaa ggagagaaca ccagcttgtt acaccctgtg agcctgcatg   9300
gaatggatga ccctgagaga gaagtgttag agtggaggtt tgacagccgc ctagcatttc   9360
atcacgtggc ccgagagctg catccggagt acttcaagaa ctgctgacat cgagcttgct   9420
acaagggact ttccgctggg gactttccag ggaggcgtgg cctgggcggg actggggagt   9480
ggcgagccct cagatgctgc atataagcag ctgctttttg cctgtactgg gtctctctgg   9540
ttagaccaga tctgagcctg ggagctctct ggctaactag ggaacccact gcttaagcct   9600
caataaagct tgccttgagt gcttcaagta gtgtgtgccc gtctgttgtg tgactctggt   9660
aactagagat ccctcagacc cttttagtca gtgtggaaaa tctctagcac ccaggaggta   9720
gaggttgcag tgagccaaga tcgcgccact gcattccagc ctgggcaaga aaacaagact   9780
gtctaaaata ataataataa gttaagggta ttaaatatat ttatacatgg aggtcataaa   9840
aatatatata tttgggctgg gcgcagtggc tcacacctgc gcccggccct ttgggaggcc   9900
gaggcaggtg gatcacctga gtttgggagt tccagaccag cctgaccaac atggagaaac   9960
cccttctctg tgtattttta gtagatttta ttttatgtgt attttattca caggtatttc  10020
tggaaaactg aaactgtttt tcctctactc tgataccaca agaatcatca gcacagagga  10080
agacttctgt gatcaaatgt ggtgggagag ggaggttttc accagcacat gagcagtcag  10140
ttctgccgca gactcggcgg gtgtccttcg gttcagttcc aacaccgcct gcctggagag  10200
aggtcagacc acagggtgag ggctcagtcc ccaagacata aacacccaag acataaacac  10260
ccaacaggtc caccccgcct gctgcccagg cagagccgat tcaccaagac gggaattagg  10320
atagagaaag agtaagtcac acagagccgg ctgtgcggga gaacggagtt ctattatgac  10380
tcaaatcagt ctccccaagc attcggggat cagagttttt aaggataact tagtgtgtag  10440
```

```
ggggccagtg agttggagat gaaagcgtag ggagtcgaag gtgtcctttt gcgccgagtc  10500
agttcctggg tgggggccac aagatcggat gagccagttt atcaatccgg gggtgccagc  10560
tgatccatgg agtgcagggt ctgcaaaata tctcaagcac tgattgatct taggttttac  10620
aatagtgatg ttaccccagg aacaatttgg ggaaggtcag aatcttgtag cctgtagctg  10680
catgactcct aaaccataat ttcttttttg tttttttttt tttatttttg agacagggtc  10740
tcactctgtc acctaggctg gagtgcagtg gtgcaatcac agctcactgc agcctcaacg  10800
tcgtaagctc aagcgatcct cccacctcag cctgcctggt agctgagact acaagcgacg  10860
ccccagttaa tttttgtatt tttggtagag gcagcgtttt gccgtgtggc cctggctggt  10920
ctcgaactcc tgggctcaag tgatccagcc tcagcctccc aaagtgctgg gacaaccggg  10980
gccagtcact gcacctggcc ctaaaccata atttctaatc ttttggctaa tttgttagtc  11040
ctacaaaggc agtctagtcc ccaggcaaaa agggggtttg tttcgggaaa gggctgttac  11100
tgtctttgtt tcaaactata aactaagttc ctcctaaact tagttcggcc tacacccagg  11160
aatgaacaag gagagcttgg aggttagaag cacgatggaa ttggttaggt cagatctctt  11220
tcactgtctg agttataatt ttgcaatggt ggttcaaaga ctgcccgctt ctgacaccag  11280
tcgctgcatt aatgaatcgg ccaacgcgcg gggagaggcg gtttgcgtat tgggcgctct  11340
tccgcttcct cgctcactga ctcgctgcgc tcggtcgttc ggctgcggcg agcggtatca  11400
gctcactcaa aggcggtaat acggttatcc acagaatcag gggataacgc aggaaagaac  11460
atgtgagcaa aaggccagca aaaggccagg aaccgtaaaa aggccgcgtt gctggcgttt  11520
ttccataggc tccgcccccc tgacgagcat cacaaaaatc gacgctcaag tcagaggtgg  11580
cgaaacccga caggactata aagataccag gcgtttcccc ctggaagctc cctcgtgcgc  11640
tctcctgttc cgaccctgcc gcttaccgga tacctgtccg cctttctccc ttcgggaagc  11700
gtggcgcttt ctcatagctc acgctgtagg tatctcagtt cggtgtaggt cgttcgctcc  11760
aagctgggct gtgtgcacga accccccgtt cagcccgacc gctgcgcctt atccggtaac  11820
tatcgtcttg agtccaaccc ggtaagacac gacttatcgc cactggcagc agccactggt  11880
aacaggatta gcagagcgag gtatgtaggc ggtgctacag agttcttgaa gtggtggcct  11940
aactacggct acactagaag aacagtattt ggtatctgcg ctctgctgaa gccagttacc  12000
ttcggaaaaa gagttggtag ctcttgatcc ggcaaacaaa ccaccgctgg tagcggtggt  12060
ttttttgttt gcaagcagca gattacgcgc agaaaaaaag gatctcaaga agatcctttg  12120
atcttttcta cggggtctga cgctcagtgg aacgaaaact cacgttaagg gattttggtc  12180
atgagattat caaaaaggat cttcacctag atccttttaa attaaaaatg aagttttaaa  12240
tcaatctaaa gtatatatga gtaaacttgg tctgacagtt accaatgctt aatcagtgag  12300
gcacctatct cagcgatctg tctatttcgt tcatccatag ttgcctgact ccccgtcgtg  12360
tagataacta cgatacggga gggcttacca tctggcccca gtgctgcaat gataccgcga  12420
gacccacgct caccggctcc agatttatca gcaataaacc agccagccgg aagggccgag  12480
cgcagaagtg gtcctgcaac tttatccgcc tccatccagt ctattaattg ttgccgggaa  12540
gctagagtaa gtagttcgcc agttaatagt ttgcgcaacg ttgttgccat tgctacaggc  12600
atcgtggtgt cacgctcgtc gtttggtatg gcttcattca gctccggttc ccaacgatca  12660
aggcgagtta catgatcccc catgttgtgc aaaaaagcgg ttagctcctt cggtcctccg  12720
atcgttgtca gaagtaagtt ggccgcagtg ttatcactca tggttatggc agcactgcat  12780
```

```
aattctctta ctgtcatgcc atccgtaaga tgcttttctg tgactggtga gtactcaacc  12840
aagtcattct gagaatagtg tatgcggcga ccgagttgct cttgcccggc gtcaatacgg  12900
gataataccg cgccacatag cagaacttta aaagtgctca tcattggaaa acgttcttcg  12960
gggcgaaaac tctcaaggat cttaccgctg ttgagatcca gttcgatgta acccactcgt  13020
gcacccaact gatcttcagc atcttttact ttcaccagcg tttctgggtg agcaaaaaca  13080
ggaaggcaaa atgccgcaaa aaagggaata agggcgacac ggaaatgttg aatactcata  13140
ctcttccttt ttcaatatta ttgaagcatt tatcagggtt attgtctcat gagcggatac  13200
atatttgaat gtatttagaa aaataaacaa ataggggttc cgcgcacatt tccccgaaaa  13260
gtgccacctg acgtctaaga aaccattatt atcatgacat taacctataa aaataggcgt  13320
atcacgaggc cctttcgtct cgcgcgtttc ggtgatgacg gtgaaaacct ctgacacatg  13380
cagctcccgg agacggtcac agcttgtctg taagcggatg ccgggagcag acaagcccgt  13440
cagggcgcgt cagcgggtgt tggcgggtgt cggggctggc ttaactatgc ggcatcagag  13500
cagattgtac tgagagtgca ccatatgcgg tgtgaaatac cgcacagatg cgtaaggaga  13560
aaataccgca tcaggcgcca ttcgccattc aggctgcgca actgttggga agggcgatcg  13620
gtgcgggcct cttcgctatt acgccagggg aggcagagat tgcagtaagc tgagatcgca  13680
gcactgcact ccagcctggg cgacagagta agactctgtc tcaaaaataa aataaataaa  13740
tcaatcagat attccaatct tttcctttat ttatttattt attttctatt ttggaaacac  13800
agtccttcct tattccagaa ttacacatat attctatttt tctttatatg ctccagtttt  13860
ttttagacct tcacctgaaa tgtgtgtata caaaatctag gccagtccag cagagcctaa  13920
aggtaaaaaa taaaataata aaaaataaat aaaatctagc tcactccttc acatcaaaat  13980
ggagatacag ctgttagcat taaataccaa ataacccatc ttgtcctcaa taattttaag  14040
cgcctctctc caccacatct aactcctgtc aaaggcatgt gccccttccg ggcgctctgc  14100
tgtgctgcca accaactggc atgtggactc tgcagggtcc ctaactgcca agccccacag  14160
tgtgccctga ggctgcccct tccttctagc ggctgccccc actcggcttt gctttcccta  14220
gtttcagtta cttgcgttca gccaaggtct gaaactaggt gcgcacagag cggtaagact  14280
gcgagagaaa gagaccagct ttacaggggg tttatcacag tgcaccctga cagtcgtcag  14340
cctcacaggg ggtttatcac attgcaccct gacagtcgtc agcctcacag gggggtttatc  14400
acagtgcacc cttacaatca ttccatttga ttcacaattt ttttagtctc tactgtgcct  14460
aacttgtaag ttaaatttga tcagaggtgt gttcccagag ggaaaaacag tatatacagg  14520
gttcagtact atcgcatttc aggcctccac ctgggtcttg gaatgtgtcc cccgaggggt  14580
gatgactacc tcagttggat ctccacaggt cacagtgaca caagataacc aagacacctc  14640
ccaaggctac cacaatgggc cgccctccac gtgcacatgg ccggaggaac tgccatgtcg  14700
gaggtgcaag cacacctgcg catcagagtc cttggtgtgg agggagggac cagcgcagct  14760
tccagccatc cacctgatga acagaaccta gggaaagccc cagttctact tacaccagga  14820
aaggc                                                              14825
```

<210> SEQ ID NO 2
<211> LENGTH: 8
<212> TYPE: DNA
<213> ORGANISM: Human immunodeficiency virus type 1

<400> SEQUENCE: 2

```
cggccgcg                                                           8
```

<210> SEQ ID NO 3
<211> LENGTH: 13
<212> TYPE: DNA
<213> ORGANISM: Human immunodeficiency virus type 1

<400> SEQUENCE: 3
tcaagaactg cct 13

<210> SEQ ID NO 4
<211> LENGTH: 39
<212> TYPE: DNA
<213> ORGANISM: Human immunodeficiency virus type 1

<400> SEQUENCE: 4
gcagccatga cccagtcacg tagcgatagc ggagtgtac 39

<210> SEQ ID NO 5
<211> LENGTH: 14887
<212> TYPE: DNA
<213> ORGANISM: Human immunodeficiency virus type 1

<400> SEQUENCE: 5
tggaagggct aatttggtcc caaaaaagac aagagatcct tgatctgtgg atctaccaca 60
cacaaggcta cttccctgat tggcagaact acacaccagg gccagggatc agatatccac 120
tgacctttgg atggtgcttc aagttagtac cagttgaacc agagcaagta gaagaggcca 180
aataaggaga gaagaacagc ttgttacacc ctatgagcca gcatgggatg gaggacccgg 240
agggagaagt attagtgtgg aagtttgaca gcctcctagc atttcgtcac atggcccgag 300
agctgcatcc ggagtactac aaagactgct gacatcgagc tttctacaag ggactttccg 360
ctggggactt tccagggagg tgtggcctgg gcgggactgg ggagtggcga gccctcagat 420
gctacatata agcagctgct ttttgcctgt actgggtctc tctggttaga ccagatctga 480
gcctgggagc tctctggcta actagggaac ccactgctta agcctcaata aagcttgcct 540
tgagtgctca aagtagtgtg tgcccgtctg ttgtgtgact ctggtaacta gagatccctc 600
agaccctttt agtcagtgtg gaaaatctct agcagtggcg cccgaacagg gacttgaaag 660
cgaaagtaaa gccagaggag atctctcgac gcaggactcg gcttgctgaa gcgcgcacgg 720
caagaggcga ggggcggcga ctggtgagta cgccaaaaat tttgactagc ggaggctaga 780
aggagagaga tgggtgcgag agcgtcggta ttaagcgggg gagaattaga taaatgggaa 840
aaaattcggt taaggccagg gggaaagaaa caatataaac taaaacatat agtatgggca 900
agcagggagc tagaacgatt cgcagttaat cctggccttt tagagacatc agaaggctgt 960
agacaaatac tgggacagct acaaccatcc cttcagacag gatcagaaga acttagatca 1020
ttatataata caatagcagt cctctattgt gtgcatcaaa ggatagatgt aaaagacacc 1080
aaggaagcct tagataagat agaggaagag caaaacaaaa gtaagaaaaa ggcacagcaa 1140
gcagcagctg acacaggaaa caacagccag gtcagccaaa attaccctat agtgcagaac 1200
ctccaggggc aaatggtaca tcaggccata tcacctagaa ctttaaatgc atgggtaaaa 1260
gtagtagaag agaaggcttt cagcccagaa gtaataccca tgttttcagc attatcagaa 1320
ggagccaccc cacaagattt aaataccatg ctaaacacag tggggggaca tcaagcagcc 1380
atgcaaatgt taaaagagac catcaatgag gaagctgcag aatgggatag attgcatcca 1440
gtgcatgcag ggcctattgc accaggccag atgagagaac caaggggaag tgacatagca 1500

-continued

```
ggaactacta gtacccttca ggaacaaata ggatggatga cacataatcc acctatccca   1560
gtaggagaaa tctataaaag atggataatc ctgggattaa ataaaatagt aagaatgtat   1620
agccctacca gcattctgga cataagacaa ggaccaaagg aaccctttag agactatgta   1680
gaccgattct ataaaactct aagagccgag caagcttcac aagaggtaaa aaattggatg   1740
acagaaacct tgttggtcca aaatgcgaac ccagattgta agactatttt aaaagcattg   1800
ggaccaggag cgacactaga agaaatgatg acagcatgtc agggagtggg gggacccggc   1860
cataaagcaa gagttttggc tgaagcaatg agccaagtaa caaatccagc taccataatg   1920
atacagaaag gcaattttag gaaccaaaga aagactgtta agtgtttcaa ttgtggcaaa   1980
gaagggcaca tagccaaaaa ttgcagggcc cctaggaaaa agggctgttg gaaatgtgga   2040
aaggaaggac accaaatgaa agattgtact gagagacagg ctaatttttt agggaagatc   2100
tggccttccc acaagggaag gccagggaat tttcttcaga gcagaccaga gccaacagcc   2160
ccaccagaag agagcttcag gtttggggaa gagacaacaa ctccctctca gaagcaggag   2220
ccgatagaca aggaactgta tcctttagct tccctcagat cactctttgg cagcgacccc   2280
tcgtcacaat aaagataggg gggcaattaa aggaagctct attagataca ggagcagatg   2340
atacagtatt agaagaaatg aatttgccag gaagatggaa accaaaaatg atagggggaa   2400
ttggaggttt tatcaaagta ggacagtatg atcagatact catagaaatc tgcggacata   2460
aagctatagg tacagtatta gtaggaccta cacctgtcaa cataattgga agaaatctgt   2520
tgactcagat tggctgcact ttaaattttc ccattagtcc tattgagact gtaccagtaa   2580
aattaaagcc aggaatggat ggcccaaaag ttaaacaatg gccattgaca gaagaaaaaa   2640
taaaagcatt agtagaaatt tgtacagaaa tggaaaagga aggaaaaatt tcaaaaattg   2700
ggcctgaaaa tccatacaat actccagtat ttgccataaa gaaaaaagac agtactaaat   2760
ggagaaaatt agtagatttc agagaactta ataagagaac tcaagatttc tgggaagttc   2820
aattaggaat accacatcct gcagggttaa aacagaaaaa atcagtaaca gtactggatg   2880
tgggcgatgc atatttttca gttcccttag ataaagactt caggaagtat actgcattta   2940
ccatacctag tataaacaat gagacaccag ggattagata tcagtacaat gtgcttccac   3000
agggatggaa aggatcacca gcaatattcc agtgtagcat gacaaaaatc ttagagcctt   3060
ttagaaaaca aaatccagac atagtcatct atcaatacat ggatgatttg tatgtaggat   3120
ctgacttaga aatagggcag catagaacaa aaatagagga actgagacaa catctgttga   3180
ggtggggatt taccacacca gacaaaaaac atcagaaaga acctccattc ctttggatgg   3240
gttatgaact ccatcctgat aaatggacag tacagcctat agtgctgcca gaaaaggaca   3300
gctggactgt caatgacata cagaaattag tgggaaaatt gaattgggca agtcagattt   3360
atgcagggat taaagtaagg caattatgta aacttcttag gggaaccaaa gcactaacag   3420
aagtagtacc actaacagaa gaagcagagc tagaactggc agaaaacagg gagattctaa   3480
aagaaccggt acatggagtg tattatgacc catcaaaaga cttaatagca gaaatacaga   3540
agcaggggca aggccaatgg acatatcaaa tttatcaaga gccatttaaa aatctgaaaa   3600
caggaaaata tgcaagaatg aagggtgccc acactaatga tgtgaaacaa ttaacagagg   3660
cagtacaaaa aatagccaca gaaagcatag taatatgggg aaagactcct aaatttaaat   3720
tacccataca aaaggaaaca tgggaagcat ggtggacaga gtattggcaa gccacctgga   3780
ttcctgagtg ggagtttgtc aatacccctc ccttagtgaa gttatggtac cagttagaga   3840
aagaacccat aataggagca gaaactttct atgtagatgg ggcagccaat agggaaacta   3900
```

```
aattaggaaa agcaggatat gtaactgaca gaggaagaca aaaagttgtc cccctaacgg   3960
acacaacaaa tcagaagact gagttacaag caattcatct agctttgcag gattcgggat   4020
tagaagtaaa catagtgaca gactcacaat atgcattggg aatcattcaa gcacaaccag   4080
ataagagtga atcagagtta gtcagtcaaa taatagagca gttaataaaa aaggaaaaag   4140
tctacctggc atgggtacca gcacacaaag gaattggagg aaatgaacaa gtagatgggt   4200
tggtcagtgc tggaatcagg aaagtactat ttttagatgg aatagataag gcccaagaag   4260
aacatgagaa atatcacagt aattggagag caatggctag tgattttaac ctaccacctg   4320
tagtagcaaa agaaatagta gccagctgtg ataaatgtca gctaaaaggg gaagccatgc   4380
atggacaagt agactgtagc ccaggaatat ggcagctaga ttgtacacat ttagaaggaa   4440
aagttatctt ggtagcagtt catgtagcca gtggatatat agaagcagaa gtaattccag   4500
cagagacagg gcaagaaaca gcatacttcc tcttaaaatt agcaggaaga tggccagtaa   4560
aaacagtaca tacagacaat ggcagcaatt tcaccagtac tacagttaag gccgcctgtt   4620
ggtgggcggg gatcaagcag gaatttggca ttccctacaa tccccaaagt caaggagtaa   4680
tagaatctat gaataaagaa ttaaagaaaa ttataggaca ggtaagagat caggctgaac   4740
atcttaagac agcagtacaa atggcagtat tcatccacaa ttttaaaaga aaagggggga   4800
ttggggggta cagtgcaggg gaaagaatag tagacataat agcaacagac atacaaacta   4860
aagaattaca aaaacaaatt acaaaaattc aaaattttcg ggtttattac agggacagca   4920
gagatccagt ttggaaagga ccagcaaagc tcctctggaa aggtgaaggg gcagtagtaa   4980
tacaagataa tagtgacata aaagtagtgc caagaagaaa agcaaagatc atcagggatt   5040
atggaaaaca gatggcaggt gatgattgtg tggcaagtag acaggatgag gattaacaca   5100
tggaaaagat tagtaaaaca ccatatgtat atttcaagga aagctaagga ctggttttat   5160
agacatcact atgaaagtac taatccaaaa ataagttcag aagtacacat cccactaggg   5220
gatgctaaat tagtaataac aacatattgg ggtctgcata caggagaaag agactggcat   5280
ttgggtcagg gagtctccat agaatggagg aaaaagagat atagcacaca agtagaccct   5340
gacctagcag accaactaat tcatctgcac tattttgatt gtttttcaga atctgctata   5400
agaaatacca tattaggacg tatagttagt cctaggtgtg aatatcaagc aggacataac   5460
aaggtaggat ctctacagta cttggcacta gcagcattaa taaaaccaaa acagataaag   5520
ccacctttgc ctagtgttag gaaactgaca gaggacagat ggaacaagcc ccagaagacc   5580
aagggccaca gagggagcca tacaatgaat ggacactaga gcttttagag gaacttaaga   5640
gtgaagctgt tagacatttt cctaggatat ggctccataa cttaggacaa catatctatg   5700
aaacttacgg ggatacttgg gcaggagtgg aagccataat aagaattctg caacaactgc   5760
tgtttatcca tttcagaatt gggtgtcgac atagcagaat aggcgttact cgacagagga   5820
gagcaagaaa tggagccagt agatcctaga ctagagccct ggaagcatcc aggaagtcag   5880
cctaaaactg cttgtaccaa ttgctattgt aaaaagtgtt gctttcattg ccaagtttgt   5940
ttcatgacaa aagccttagg catctcctat ggcaggaaga agcggagaca gcgacgaaga   6000
gctcatcaga acagtcagac tcatcaagct tctctatcaa agcagtaagt agtacatgta   6060
atgcaaccta taatagtagc aatagtagca ttagtagtag caataataat agcaatagtt   6120
gtgtggtcca tagtaatcat agaatatagg aaaatattaa gacaaagaaa aatagacagg   6180
ttaattgata gactaataga aagagcagaa gacagtggca atgagagtga aggagaagta   6240
```

-continued

```
tcagcacttg tggagatggg ggtggaaatg gggcaccatg ctccttggga tattgatgat   6300
ctgtagtgct acagaaaaat tgtgggtcac cgtctattat ggggtacctg tgtggaagga   6360
agcaaccacc actctatttt gtgcatcaga tgctaaagca tatgatacag aggtacataa   6420
tgtttgggcc acacatgcct gtgtacccac agaccccaac ccacaagaag tagtattggt   6480
aaatgtgaca gaaaatttta acatgtggaa aaatgacatg gtagaacaga tgcatgagga   6540
tataatcagt ttatgggatc aaagcctaaa gccatgtgta aaattaaccc cactctgtgt   6600
tagtttaaag tgcactgatt tgaagaatga tactaatacc aatagtagta gcgggagaat   6660
gataatggag aaaggagaga taaaaaactg ctctttcaat atcagcacaa gcataagaga   6720
taaggtgcag aaagaatatg cattctttta taaacttgat atagtaccaa tagataatac   6780
cagctatagg ttgataagtt gtaacacctc agtcattaca caggcctgtc caaaggtatc   6840
ctttgagcca attcccatac attattgtgc cccggctggt tttgcgattc taaaatgtaa   6900
taataagacg ttcaatggaa caggaccatg tacaaatgtc agcacagtac aatgtacaca   6960
tggaatcagg ccagtagtat caactcaact gctgttaaat ggcagtctag cagaagaaga   7020
tgtagtaatt agatctgcca atttcacaga caatgctaaa accataatag tacagctgaa   7080
cacatctgta gaaattaatt gtacaagacc caacaacaat acaagaaaaa gtatccgtat   7140
ccagagggga ccagggagag catttgttac aataggaaaa ataggaaata tgagacaagc   7200
acattgtaac attagtagag caaaatggaa tgccacttta aaacagatag ctagcaaatt   7260
aagagaacaa tttggaaata ataaaacaat aatctttaag caatcctcag gaggggaccc   7320
agaaattgta acgcacagtt ttaattgtgg aggggaattt ttctactgta attcaacaca   7380
actgtttaat agtacttggt ttaatagtac ttggagtact gaagggtcaa ataacactga   7440
aggaagtgac acaatcacac tcccatgcag aataaaacaa tttataaaca tgtggcagga   7500
agtaggaaaa gcaatgtatg cccctcccat cagtggacaa attagatgtt catcaaatat   7560
tactgggctg ctattaacaa gagatggtgg taataacaac aatgggtccg agatcttcag   7620
acctggagga ggcgatatga gggacaattg gagaagtgaa ttatataaat ataaagtagt   7680
aaaaattgaa ccattaggag tagcacccac caaggcaaag agaagagtgg tgcagagaga   7740
aaaaagagca gtgggaatag gagctttgtt ccttgggttc ttgggagcag caggaagcac   7800
tatgggcgca gcgtcaatga cgctgacggt acaggccaga caattattgt ctgatatagt   7860
gcagcagcag aacaatttgc tgagggctat tgaggcgcaa cagcatctgt tgcaactcac   7920
agtctggggc atcaaacagc tccaggcaag aatcctggct gtggaaagat acctaaagga   7980
tcaacagctc ctggggattt ggggttgctc tggaaaactc atttgcacca ctgctgtgcc   8040
ttggaatgct agttggagta ataaatctct ggaacagatt tggaataaca tgacctggat   8100
ggagtgggac agagaaatta acaattacac aagcttaata cactccttaa ttgaagaatc   8160
gcaaaaccag caagaaaaga atgaacaaga attattggaa ttagataaat gggcaagttt   8220
gtggaattgg tttaacataa caaattggct gtggtatata aaattattca taatgatagt   8280
aggaggcttg gtaggtttaa gaatagtttt tgctgtactt tctatagtga atagagttag   8340
gcagggatat tcaccattat cgtttcagac ccacctccca atcccgaggg gacccgacag   8400
gcccgaagga atagaagaag aaggtggaga gagagacaga gacagatcca ttcgattagt   8460
gaacggatcc ttagcactta tctgggacga tctgcggagc ctgtgcctct tcagctacca   8520
ccgcttgaga gacttactct tgattgtaac gaggattgtg gaacttctgg gacgcagggg   8580
gtgggaagcc ctcaaatatt ggtggaatct cctacagtat tggagtcagg aactaaagaa   8640
```

```
tagtgctgtt aacttgctca atgccacagc catagcagta gctgagggga cagatagggt   8700
tatagaagta ttacaagcag cttatagagc tattcgccac atacctagaa gaataagaca   8760
gggcttggaa aggattttgc tataagcggc cgcgatgggt ggcaagtggt caaaaagtag   8820
tgtgattgga tggcctgctg taagggaaag aatgagacga gctgagccag cagcagatgg   8880
ggtgggagca gtatctcgag acctagaaaa acatggagca atcacaagta gcaatacagc   8940
agctaacaat gctgcttgtg cctggctaga agcacaagag gaggaagagg tgggttttcc   9000
agtcacacct caggtacctt taagaccaat gacttacaag gcagctgtag atcttagcca   9060
ctttttaaaa gaaaaggggg gactggaagg gctaattcac tcccaaagaa gacaagatat   9120
ccttgatctg tggatctacc acacacaagg ctacttccct gattggcaga actacacacc   9180
agggccaggg gtcagatatc cactgacctt tggatggtgc tacaagctag taccagttga   9240
gccagataag gtagaagagg ccaataaagg agagaacacc agcttgttac accctgtgag   9300
cctgcatgga atggatgacc ctgagagaga agtgttagag tggaggtttg acagccgcct   9360
agcatttcat cacgtggccc gagagctgca tccggagtac ttcaagaact gctgacatcg   9420
agcttgctac aagggacttt ccgctgggga ctttccaggg aggcgtggcc tgggcgggac   9480
tggggagtgg cgagccctca gatgctgcat ataagcagct gctttttgcc tgtactgggt   9540
ctctctggtt agaccagatc tgagcctggg agctctctgg ctaactaggg aacccactgc   9600
ttaagcctca ataaagcttg ccttgagtgc ttcaagtagt gtgtgcccgt ctgttgtgtg   9660
actctggtaa ctagagatcc ctcagaccct tttagtcagt gtggaaaatc tctagcaccc   9720
cccaggaggt agaggttgca gtgagccaag atcgcgccac tgcattccag cctgggcaag   9780
aaaacaagac tgtctaaaat aataataata agttaagggt attaaatata tttatacatg   9840
gaggtcataa aaatatatat atttgggctg ggcgcagtgg ctcacacctg cgcccggccc   9900
tttgggaggc cgaggcaggt ggatcacctg agtttgggag ttccagacca gcctgaccaa   9960
catggagaaa ccccttctct gtgtattttt agtagatttt attttatgtg tattttattc  10020
acaggtattt ctggaaaact gaaactgttt ttcctctact ctgataccac aagaatcatc  10080
agcacagagg aagacttctg tgatcaaatg tggtgggaga gggaggtttt caccagcaca  10140
tgagcagtca gttctgccgc agactcggcg ggtgtccttc ggttcagttc caacaccgcc  10200
tgcctggaga gaggtcagac cacagggtga gggctcagtc cccaagacat aaacacccaa  10260
gacataaaca cccaacaggt ccaccccgcc tgctgcccag gcagagccga ttcaccaaga  10320
cgggaattag gatagagaaa gagtaagtca cacagagccg gctgtgcggg agaacggagt  10380
tctattatga ctcaaatcag tctccccaag cattcgggga tcagagtttt taaggataac  10440
ttagtgtgta gggggccagt gagttggaga tgaaagcgta gggagtcgaa ggtgtccttt  10500
tgcgccgagt cagttcctgg gtgggggcca caagatcgga tgagccagtt tatcaatccg  10560
gggtgccag ctgatccatg gagtgcaggg tctgcaaaat atctcaagca ctgattgatc   10620
ttaggtttta caatagtgat gttaccccag gaacaatttg gggaaggtca gaatcttgta  10680
gcctgtagct gcatgactcc taaaccataa tttctttttt gttttttttt ttttattttt  10740
gagacagggt ctcactctgt cacctaggct ggagtgcagt ggtgcaatca cagctcactg  10800
cagcctcaac gtcgtaagct caagcgatcc tcccacctca gcctgcctgg tagctgagac  10860
tacaagcgac gccccagtta atttttgtat ttttggtaga ggcagcgttt tgccgtgtgg  10920
ccctggctgg tctcgaactc ctgggctcaa gtgatccagc ctcagcctcc caaagtgctg  10980
```

-continued

```
ggacaaccgg ggccagtcac tgcacctggc cctaaaccat aatttctaat cttttggcta  11040
atttgttagt cctacaaagg cagtctagtc cccaggcaaa aagggggttt gtttcgggaa  11100
agggctgtta ctgtctttgt ttcaaactat aaactaagtt cctcctaaac ttagttcggc  11160
ctacacccag gaatgaacaa ggagagcttg gaggttagaa gcacgatgga attggttagg  11220
tcagatctct ttcactgtct gagttataat tttgcaatgg tggttcaaag actgcccgct  11280
tctgacacca gtcgctgcat taatgaatcg gccaacgcgc ggggagaggc ggtttgcgta  11340
ttggcgctct tccgcttcct cgctcactga ctcgctgcgc tcggtcgttc ggctgcggcg  11400
agcggtatca gctcactcaa aggcggtaat acggttatcc acagaatcag gggataacgc  11460
aggaaagaac atgtgagcaa aaggccagca aaaggccagg aaccgtaaaa aggccgcgtt  11520
gctggcgttt ttccataggc tccgcccccc tgacgagcat cacaaaaatc gacgctcaag  11580
tcagaggtgg cgaaacccga caggactata aagataccag gcgtttcccc ctggaagctc  11640
cctcgtgcgc tctcctgttc cgaccctgcc gcttaccgga tacctgtccg cctttctccc  11700
ttcgggaagc gtggcgcttt ctcaatgctc acgctgtagg tatctcagtt cggtgtaggt  11760
cgttcgctcc aagctgggct gtgtgcacga accccccgtt cagcccgacc gctgcgcctt  11820
atccggtaac tatcgtcttg agtccaaccc ggtaagacac gacttatcgc cactggcagc  11880
agccactggt aacaggatta gcagagcgag gtatgtaggc ggtgctacag agttcttgaa  11940
gtggtggcct aactacggct acactagaag gacagtattt ggtatctgcg ctctgctgaa  12000
gccagttacc ttcggaaaaa gagttggtag ctcttgatcc ggcaaacaaa ccaccgctgg  12060
tagcggtggt ttttttgttt gcaagcagca gattacgcgc agaaaaaaag gatctcaaga  12120
agatcctttg atcttttcta cggggtctga cgctcagtgg aacgaaaact cacgttaagg  12180
gattttggtc atgagattat caaaaaggat cttcacctag atccttttaa attaaaaatg  12240
aagttttaaa tcaatctaaa gtatatatga gtaaacttgg tctgacagtt accaatgctt  12300
aatcagtgag gcacctatct cagcgatctg tctatttcgt tcatccatag ttgcctgact  12360
ccccgtcgtg tagataacta cgatacggga gggcttacca tctggcccca gtgctgcaat  12420
gataccgcga gacccacgct caccggctcc agatttatca gcaataaacc agccagccgg  12480
aagggccgag cgcagaagtg gtcctgcaac tttatccgcc tccatccagt ctattaattg  12540
ttgccgggaa gctagagtaa gtagttcgcc agttaatagt ttgcgcaacg ttgttgccat  12600
tgctacaggc atcgtggtgt cacgctcgtc gtttggtatg gcttcattca gctccggttc  12660
ccaacgatca aggcgagtta catgatcccc catgttgtgc aaaaaagcgg ttagctcctt  12720
cggtcctccg atcgttgtca gaagtaagtt ggccgcagtg ttatcactca tggttatggc  12780
agcactgcat aattctctta ctgtcatgcc atccgtaaga tgcttttctg tgactggtga  12840
gtactcaacc aagtcattct gagaatagtg tatgcggcga ccgagttgct cttgcccggc  12900
gtcaatacgg gataataccg cgccacatag cagaacttta aaagtgctca tcattggaaa  12960
acgttcttcg gggcgaaaac tctcaaggat cttaccgctg ttgagatcca gttcgatgta  13020
acccactcgt gcacccaact gatcttcagc atcttttact ttcaccagcg tttctgggtg  13080
agcaaaaaca ggaaggcaaa atgccgcaaa aaagggaata agggcgacac ggaaatgttg  13140
aatactcata ctcttccttt ttcaatatta ttgaagcatt tatcagggtt attgtctcat  13200
gagcggatac atatttgaat gtatttagaa aaataaacaa ataggggttc cgcgcacatt  13260
tccccgaaaa gtgccacctg acgtctaaga aaccattatt atcatgacat taacctataa  13320
aaataggcgt atcacgaggc cctttcgtct tcaagaactg cctcgcgcgt ttcggtgatg  13380
```

```
acggtgaaaa cctctgacac atgcagctcc cggagacggt cacagcttgt ctgtaagcgg  13440
atgccgggag cagacaagcc cgtcagggcg cgtcagcggg tgttggcggg tgtcggggcg  13500
cagccatgac ccagtcacgt agcgatagcg gagtgtactg gcttaactat gcggcatcag  13560
agcagattgt actgagagtg caccatatgc ggtgtgaaat accgcacaga tgcgtaagga  13620
gaaaataccg catcaggcgc cattcgccat tcaggctgcg caactgttgg gaagggcgat  13680
cggtgcgggc ctcttcgcta ttacgccagg ggaggcagag attgcagtaa gctgagatcg  13740
cagcactgca ctccagcctg ggcgacagag taagactctg tctcaaaaat aaaataaata  13800
aatcaatcag atattccaat cttttccttt atttatttat ttattttcta ttttggaaac  13860
acagtccttc cttattccag aattacacat atattctatt tttctttata tgctccagtt  13920
tttttagac cttcacctga aatgtgtgta tacaaaatct aggccagtcc agcagagcct  13980
aaaggtaaaa aataaaataa taaaaaataa ataaaatcta gctcactcct tcacatcaaa  14040
atggagatac agctgttagc attaaatacc aaataaccca tcttgtcctc aataatttta  14100
agcgcctctc tccaccacat ctaactcctg tcaaaggcat gtgccccttc cgggcgctct  14160
gctgtgctgc caaccaactg gcatgtggac tctgcagggt ccctaactgc caagccccac  14220
agtgtgccct gaggctgccc cttccttcta gcggctgccc ccactcggct ttgctttccc  14280
tagtttcagt tacttgcgtt cagccaaggt ctgaaactag gtgcgcacag agcggtaaga  14340
ctgcgagaga aagagaccag ctttacaggg ggtttatcac agtgcaccct gacagtcgtc  14400
agcctcacag gggggtttatc acattgcacc ctgacagtcg tcagcctcac agggggttta  14460
tcacagtgca cccttacaat cattccattt gattcacaat ttttttagtc tctactgtgc  14520
ctaacttgta agttaaattt gatcagaggt gtgttcccag aggggaaaac agtatataca  14580
gggttcagta ctatcgcatt tcaggcctcc acctgggtct tggaatgtgt cccccgaggg  14640
gtgatgacta cctcagttgg atctccacag gtcacagtga cacaagataa ccaagacacc  14700
tcccaaggct accacaatgg gccgccctcc acgtgcacat ggccggagga actgccatgt  14760
cggaggtgca agcacacctg cgcatcagag tccttggtgt ggagggaggg accagcgcag  14820
cttccagcca tccacctgat gaacagaacc tagggaaagc cccagttcta cttacaccag  14880
gaaaggc                                                            14887
```

<210> SEQ ID NO 6
<211> LENGTH: 14812
<212> TYPE: DNA
<213> ORGANISM: Human immunodeficiency virus type 1

<400> SEQUENCE: 6

```
tggaagggct aatttggtcc caaaaaagac aagagatcct tgatctgtgg atctaccaca     60
cacaaggcta cttccctgat tggcagaact acacaccagg gccagggatc agatatccac    120
tgacctttgg atggtgcttc aagttagtac cagttgaacc agagcaagta gaagaggcca    180
aataaggaga gaagaacagc ttgttacacc ctatgagcca gcatgggatg gaggacccgg    240
agggagaagt attagtgtgg aagtttgaca gcctcctagc atttcgtcac atggcccgag    300
agctgcatcc ggagtactac aaagactgct gacatcgagc tttctacaag ggactttccg    360
ctggggactt tccagggagg tgtggcctgg gcgggactgg ggagtggcga gccctcagat    420
gctacatata agcagctgct ttttgcctgt actgggtctc tctggttaga ccagatctga    480
gcctgggagc tctctggcta actagggaac ccactgctta agcctcaata aagcttgcct    540
```

```
tgagtgctca aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagtaaa gccagaggag atctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcggta ttaagcgggg gagaattaga taaatgggaa    840
aaaattcggt taaggccagg gggaaagaaa caatataaac taaaacatat agtatgggca    900
agcagggagc tagaacgatt cgcagttaat cctggccttt tagagacatc agaaggctgt    960
agacaaatac tgggacagct acaaccatcc cttcagacag gatcagaaga acttagatca   1020
ttatataata caatagcagt cctctattgt gtgcatcaaa ggatagatgt aaaagacacc   1080
aaggaagcct tagataagat agaggaagag caaaacaaaa gtaagaaaaa ggcacagcaa   1140
gcagcagctg acacaggaaa caacagccag gtcagccaaa attaccctat agtgcagaac   1200
ctccaggggc aaatggtaca tcaggccata tcacctagaa ctttaaatgc atgggtaaaa   1260
gtagtagaag agaaggcttt cagcccagaa gtaataccca tgttttcagc attatcagaa   1320
ggagccaccc cacaagattt aaataccatg ctaaacacag tggggggaca tcaagcagcc   1380
atgcaaatgt taaaagagac catcaatgag gaagctgcag aatgggatag attgcatcca   1440
gtgcatgcag ggcctattgc accaggccag atgagagaac caaggggaag tgacatagca   1500
ggaactacta gtacccttca ggaacaaata ggatggatga cacataatcc acctatccca   1560
gtaggagaaa tctataaaag atggataatc ctgggattaa ataaaatagt aagaatgtat   1620
agccctacca gcattctgga cataagacaa ggaccaaagg aaccctttag agactatgta   1680
gaccgattct ataaaactct aagagccgag caagcttcac aagaggtaaa aaattggatg   1740
acagaaacct tgttggtcca aaatgcgaac ccagattgta agactatttt aaaagcattg   1800
ggaccaggag cgacactaga agaaatgatg acagcatgtc agggagtggg gggacccggc   1860
cataaagcaa gagttttggc tgaagcaatg agccaagtaa caaatccagc taccataatg   1920
atacagaaag gcaattttag gaaccaaaga aagactgtta agtgtttcaa ttgtggcaaa   1980
gaagggcaca tagccaaaaa ttgcagggcc cctaggaaaa agggctgttg gaaatgtgga   2040
aaggaaggac accaaatgaa agattgtact gagagacagg ctaatttttt agggaagatc   2100
tggccttccc acaagggaag gccagggaat tttcttcaga gcagaccaga gccaacagcc   2160
ccaccagaag agagcttcag gtttggggaa gagacaacaa ctccctctca gaagcaggag   2220
ccgatagaca aggaactgta tcctttagct tccctcagat cactctttgg cagcgacccc   2280
tcgtcacaat aaagataggg gggcaattaa aggaagctct attagataca ggagcagatg   2340
atacagtatt agaagaaatg aatttgccag gaagatggaa accaaaaatg atagggggaa   2400
ttggaggttt tatcaaagta ggacagtatg atcagatact catagaaatc tgcggacata   2460
aagctatagg tacagtatta gtaggaccta cacctgtcaa cataattgga agaaatctgt   2520
tgactcagat tggctgcact ttaaattttc ccattagtcc tattgagact gtaccagtaa   2580
aattaaagcc aggaatggat ggcccaaaag ttaaacaatg gccattgaca gaagaaaaaa   2640
taaaagcatt agtagaaatt tgtacagaaa tggaaaagga aggaaaaatt tcaaaaattg   2700
ggcctgaaaa tccatacaat actccagtat ttgccataaa gaaaaaagac agtactaaat   2760
ggagaaaatt agtagatttc agagaactta ataagagaac tcaagatttc tgggaagttc   2820
aattaggaat accacatcct gcagggttaa aacagaaaaa atcagtaaca gtactggatg   2880
tgggcgatgc atatttttca gttcccttag ataaagactt caggaagtat actgcattta   2940
```

```
ccatacctag tataaacaat gagacaccag ggattagata tcagtacaat gtgcttccac   3000
agggatggaa aggatcacca gcaatattcc agtgtagcat gacaaaaatc ttagagcctt   3060
ttagaaaaca aaatccagac atagtcatct atcaatacat ggatgatttg tatgtaggat   3120
ctgacttaga aatagggcag catagaacaa aaatagagga actgagacaa catctgttga   3180
ggtggggatt taccacacca gacaaaaaac atcagaaaga acctccattc ctttggatgg   3240
gttatgaact ccatcctgat aaatggacag tacagcctat agtgctgcca gaaaaggaca   3300
gctggactgt caatgacata cagaaattag tgggaaaatt gaattgggca agtcagattt   3360
atgcagggat taaagtaagg caattatgta aacttcttag gggaaccaaa gcactaacag   3420
aagtagtacc actaacagaa gaagcagagc tagaactggc agaaaacagg gagattctaa   3480
aagaaccggt acatggagtg tattatgacc catcaaaaga cttaatagca gaaatacaga   3540
agcaggggca aggccaatgg acatatcaaa tttatcaaga gccatttaaa aatctgaaaa   3600
caggaaaata tgcaagaatg aagggtgccc acactaatga tgtgaaacaa ttaacagagg   3660
cagtacaaaa aatagccaca gaaagcatag taatatgggg aaagactcct aaatttaaat   3720
tacccataca aaaggaaaca tggaagcat ggtggacaga gtattggcaa gccacctgga   3780
ttcctgagtg ggagtttgtc aatacccctc ccttagtgaa gttatggtac cagttagaga   3840
aagaacccat aataggagca gaaactttct atgtagatgg ggcagccaat agggaaacta   3900
aattaggaaa agcaggatat gtaactgaca gaggaagaca aaaagttgtc cccctaacgg   3960
acacaacaaa tcagaagact gagttacaag caattcatct agctttgcag gattcgggat   4020
tagaagtaaa catagtgaca gactcacaat atgcattggg aatcattcaa gcacaaccag   4080
ataagagtga atcagagtta gtcagtcaaa taatagagca gttaataaaa aaggaaaaag   4140
tctacctggc atgggtacca gcacacaaag gaattggagg aaatgaacaa gtagatgggt   4200
tggtcagtgc tggaatcagg aaagtactat ttttagatgg aatagataag gcccaagaag   4260
aacatgagaa atatcacagt aattggagag caatggctag tgattttaac ctaccacctg   4320
tagtagcaaa agaaatagta gccagctgtg ataaatgtca gctaaaaggg gaagccatgc   4380
atggacaagt agactgtagc ccaggaatat ggcagctaga ttgtacacat ttagaaggaa   4440
aagttatctt ggtagcagtt catgtagcca gtggatatat agaagcagaa gtaattccag   4500
cagagacagg gcaagaaaca gcatacttcc tcttaaaatt agcaggaaga tggccagtaa   4560
aaacagtaca tacagacaat ggcagcaatt tcaccagtac tacagttaag gccgcctgtt   4620
ggtgggcggg gatcaagcag gaatttggca ttccctacaa tccccaaagt caaggagtaa   4680
tagaatctat gaataaagaa ttaaagaaaa ttataggaca ggtaagagat caggctgaac   4740
atcttaagac agcagtacaa atggcagtat tcatccacaa ttttaaaaga aaagggggga   4800
ttggggggta cagtgcaggg gaaagaatag tagacataat agcaacagac atacaaacta   4860
aagaattaca aaaacaaatt acaaaaattc aaaattttcg ggtttattac agggacagca   4920
gagatccagt ttggaaagga ccagcaaagc tcctctggaa aggtgaaggg gcagtagtaa   4980
tacaagataa tagtgacata aaagtagtgc caagaagaaa agcaaagatc atcagggatt   5040
atggaaaaca gatggcaggt gatgattgtg tggcaagtag acaggatgag gattaacaca   5100
tggaaaagat tagtaaaaca ccatatgtat atttcaagga aagctaagga ctggttttat   5160
agacatcact atgaaagtac taatccaaaa ataagttcag aagtacacat cccactaggg   5220
gatgctaaat tagtaataac aacatattgg ggtctgcata caggagaaag agactggcat   5280
```

-continued

```
ttgggtcagg gagtctccat agaatggagg aaaaagagat atagcacaca agtagaccct   5340
gacctagcag accaactaat tcatctgcac tattttgatt gtttttcaga atctgctata   5400
agaaatacca tattaggacg tatagttagt cctaggtgtg aatatcaagc aggacataac   5460
aaggtaggat ctctacagta cttggcacta gcagcattaa taaaaccaaa acagataaag   5520
ccacctttgc ctagtgttag gaaactgaca gaggacagat ggaacaagcc ccagaagacc   5580
aagggccaca gagggagcca tacaatgaat ggacactaga gcttttagag gaacttaaga   5640
gtgaagctgt tagacatttt cctaggatat ggctccataa cttaggacaa catatctatg   5700
aaacttacgg ggatacttgg gcaggagtgg aagccataat aagaattctg caacaactgc   5760
tgtttatcca tttcagaatt gggtgtcgac atagcagaat aggcgttact cgacagagga   5820
gagcaagaaa tggagccagt agatcctaga ctagagccct ggaagcatcc aggaagtcag   5880
cctaaaactg cttgtaccaa ttgctattgt aaaaagtgtt gctttcattg ccaagtttgt   5940
ttcatgacaa aagccttagg catctcctat ggcaggaaga agcggagaca gcgacgaaga   6000
gctcatcaga acagtcagac tcatcaagct tctctatcaa agcagtaagt agtacatgta   6060
atgcaaccta taatagtagc aatagtagca ttagtagtag caataataat agcaatagtt   6120
gtgtggtcca tagtaatcat agaatatagg aaaatattaa gacaaagaaa aatagacagg   6180
ttaattgata gactaataga aagagcagaa gacagtggca atgagagtga aggagaagta   6240
tcagcacttg tggagatggg ggtggaaatg gggcaccatg ctccttggga tattgatgat   6300
ctgtagtgct acagaaaaat tgtgggtcac cgtctattat ggggtacctg tgtggaaaga   6360
aacaaccacc actctatttt gtgcatcaga tgctaaagca tatgatacag aggtacataa   6420
tgtttgggcc acacatgcct gtgtacccac agaccccaac ccacaagaag tagtattgga   6480
aaatgtaaca gaagatttta acatgtggaa aaataacatg gtagaacaga tgcaggagga   6540
tgtaatcaat ttatgggatc aaagcttaaa gccatgtgta aaattaaccc cactctgtgt   6600
tactttaaat tgcaaagatg tgaatgctac taataccact agtagtagtg agggaatgat   6660
ggagagagga gaaataaaaa actgctcttt caatatcacc aaaagcataa gagataaggt   6720
gcagaaagaa tatgctcttt tttataaact ggatgtagta ccaatagata ataagaataa   6780
taccaaatat aggttaataa gttgtaacac ctcagtcatt acacaagcct gtccaaaggt   6840
atcctttgaa ccaattccca tacattattg tgccccggct ggttttgcga ttctaaagtg   6900
taataataag acattcaatg gaaaaggaca atgtaaaaat gtcagcacag tacaatgtac   6960
acatggaatt aggccagtag tatcaactca actgctgcta aatggcagtc tagcagaaga   7020
aaaggttgta attagatctg acaattttac ggacaatgct aaaaccataa tagtacagct   7080
gaatgaatct gtaaaaatta attgtacaag gcccagcaac aatacaagaa aaagtataca   7140
tataggacca gggagagcat tttatacaac aggagaaata ataggagata taagacaagc   7200
acattgtaac attagtagag cacaatggaa taacacttta aaacagatag ttgaaaaatt   7260
aagagaacaa tttaataata aaacaatagt ctttactcac tcctcaggag gggatccaga   7320
aattgtaatg cacagtttta attgtggagg ggaatttttc tactgtaatt caacacaact   7380
gtttaatagt acttggaatg atactgaaaa gtcaagtggc actgaaggaa atgacaccat   7440
catactccca tgcagaataa aacaaattat aaacatgtgg caggaagtgg gaaaagcaat   7500
gtatgctcct cccattaaag gacaaattag atgttcatca aatattacag ggctgctatt   7560
aacaagagat ggtggtaaaa atgagagtga gatcgagatc ttcagacctg gaggaggaga   7620
catgagggac aattggagaa gtgaattata taaatataaa gtagtaaaaa ttgaaccatt   7680
```

-continued

```
aggagtagca cccaccaagg caaagagaag agtggtgcaa agagaaaaaa gagcagtggg   7740
aataggagct ttgttccttg ggttcttggg agcagcagga agcactatgg gcgcagcgtc   7800
aatgacactg acggtacagg ccagacaatt attgtctggt atagtgcaac agcaaaacaa   7860
tttgctgagg gctattgagg cgcaacagca tatgttgcaa ctcacagtct ggggcatcaa   7920
gcagctccag gcaagagtcc tggctgtgga aagataccta aaggatcaac agctcatggg   7980
gatttggggt tgctctggaa aactcatttg caccactgct gtgccttgga atactagttg   8040
gagtaataaa tctctggata gtatttggaa taacatgacc tggatggagt gggaaaaaga   8100
aattgagaat tacacaaaca caatatacac cctaattgaa gaatcgcaga tccaacaaga   8160
aaagaatgaa caagaattat tggaattaga taaatgggca agtttgtgga attggtttgg   8220
cataacaaaa tggctgtggt atataaaaat attcataatg atagtaggag gcttgatagg   8280
tttaagaata gtttttctg tactttctat agtgaataga gttaggcagg gatactcacc   8340
cttatcgttt cagaccctcc tcccagcaac gaggggaccc gacaggcccg aaggaatcga   8400
agaagaaggt ggagagagag acagagacag atccggacaa ttagtgaacg gattcttagc   8460
acttatctgg gtcgacctgc ggagcctgtt cctcttcagc taccaccgct tgagagactt   8520
actcttgact gtaacgagga ttgtggaact tctgggacgc agggggtggg aaatcctgaa   8580
atactggtgg aatctcctac agtattggag tcaggaacta aagaatagtg ctgttagctt   8640
gcttaatgcc acagctatag cagtagctga ggggacagat aggattatag aagtagtaca   8700
aagagtttat agggctattc tccacatacc tacaagaata agacagggct tggaaagggc   8760
tttgctataa gcggccgcga tgggtggcaa gtggtcaaaa agtagtgtga ttggatggcc   8820
tgctgtaagg gaaagaatga gacgagctga gccagcagca gatggggtgg gagcagtatc   8880
tcgagaccta gaaaaacatg gagcaatcac aagtagcaat acagcagcta acaatgctgc   8940
ttgtgcctgg ctagaagcac aagaggagga agaggtgggt tttccagtca cacctcaggt   9000
acctttaaga ccaatgactt acaaggcagc tgtagatctt agccactttt taaaagaaaa   9060
ggggggactg gaagggctaa ttcactccca aagaagacaa gatatccttg atctgtggat   9120
ctaccacaca caaggctact tccctgattg gcagaactac acaccagggc caggggtcag   9180
atatccactg acctttggat ggtgctacaa gctagtacca gttgagccag ataaggtaga   9240
tgaccctgag agagaagtgt tagagtggag gtttgacagc cgcctagcat ttcatcacgt   9300
ggcccgagag ctgcatccgg agtacttcaa gaactgctga catcgagctt gctacaaggg   9360
actttccgct ggggactttc cagggaggcg tggcctgggc gggactgggg agtggcgagc   9420
cctcagatgc tgcatataag cagctgcttt ttgcctgtac tgggtctctc tggttagacc   9480
agatctgagc ctgggagctc tctggctaac tagggaaccc actgcttaag cctcaataaa   9540
gcttgccttg agtgcttcaa gtagtgtgtg cccgtctgtt gtgtgactct ggtaactaga   9600
gatccctcag accctttag tcagtgtgga aaatctctag cacccccag gaggtagagg   9660
ttgcagtgag ccaagatcgc gccactgcat tccagcctgg gcaagaaaac aagactgtct   9720
aaaataataa taataagtta agggtattaa atatatttat acatggaggt cataaaaata   9780
tatatatttg ggctgggcgc agtggctcac acctgcgccc ggccctttgg gaggccgagg   9840
caggtggatc acctgagttt gggagttcca gaccagcctg accaacatgg agaaacccct   9900
tctctgtgta tttttagtag attttatttt atgtgtattt tattcacagg tatttctgga   9960
aaactgaaac tgtttttcct ctactctgat accacaagaa tcatcagcac agaggaagac  10020
```

```
ttctgtgatc aaatgtggtg ggagagggag gttttcacca gcacatgagc agtcagttct  10080
gccgcagact cggcgggtgt ccttcggttc agttccaaca ccgcctgcct ggagagaggt  10140
cagaccacag ggtgagggct cagtccccaa gacataaaca cccaagacat aaacacccaa  10200
caggtccacc ccgcctgctg cccaggcaga gccgattcac caagacggga attaggatag  10260
agaaagagta agtcacacag agccggctgt gcgggagaac ggagttctat tatgactcaa  10320
atcagtctcc ccaagcattc ggggatcaga gtttttaagg ataacttagt gtgtaggggg  10380
ccagtgagtt ggagatgaaa gcgtagggag tcgaaggtgt ccttttgcgc cgagtcagtt  10440
cctgggtggg ggccacaaga tcggatgagc cagtttatca atccgggggt gccagctgat  10500
ccatggagtg cagggtctgc aaaatatctc aagcactgat tgatcttagg ttttacaata  10560
gtgatgttac cccaggaaca atttggggaa ggtcagaatc ttgtagcctg tagctgcatg  10620
actcctaaac cataatttct tttttgtttt tttttttta tttttgagac agggtctcac  10680
tctgtcacct aggctggagt gcagtggtgc aatcacagct cactgcagcc tcaacgtcgt  10740
aagctcaagc gatcctccca cctcagcctg cctggtagct gagactacaa gcgacgcccc  10800
agttaatttt tgtatttttg gtagaggcag cgttttgccg tgtggccctg gctggtctcg  10860
aactcctggg ctcaagtgat ccagcctcag cctcccaaag tgctgggaca accggggcca  10920
gtcactgcac ctggccctaa accataattt ctaatctttt ggctaatttg ttagtcctac  10980
aaaggcagtc tagtccccag gcaaaaaggg ggtttgtttc gggaaagggc tgttactgtc  11040
tttgtttcaa actataaact aagttcctcc taaacttagt tcggcctaca cccaggaatg  11100
aacaaggaga gcttggaggt tagaagcacg atggaattgg ttaggtcaga tctctttcac  11160
tgtctgagtt ataattttgc aatggtggtt caaagactgc ccgcttctga caccagtcgc  11220
tgcattaatg aatcggccaa cgcgcgggga gaggcggttt gcgtattggc gctcttccgc  11280
ttcctcgctc actgactcgc tgcgctcggt cgttcggctg cggcgagcgg tatcagctca  11340
ctcaaaggcg gtaatacggt tatccacaga atcaggggat aacgcaggaa agaacatgtg  11400
agcaaaaggc cagcaaaagg ccaggaaccg taaaaaggcc gcgttgctgg cgtttttcca  11460
taggctccgc ccccctgacg agcatcacaa aaatcgacgc tcaagtcaga ggtggcgaaa  11520
cccgacagga ctataaagat accaggcgtt tccccctgga agctccctcg tgcgctctcc  11580
tgttccgacc ctgccgctta ccggatacct gtccgccttt ctcccttcgg gaagcgtggc  11640
gctttctcaa tgctcacgct gtaggtatct cagttcggtg taggtcgttc gctccaagct  11700
gggctgtgtg cacgaacccc ccgttcagcc cgaccgctgc gccttatccg gtaactatcg  11760
tcttgagtcc aacccggtaa gacacgactt atcgccactg gcagcagcca ctggtaacag  11820
gattagcaga gcgaggtatg taggcggtgc tacagagttc ttgaagtggt ggcctaacta  11880
cggctacact agaaggacag tatttggtat ctgcgctctg ctgaagccag ttaccttcgg  11940
aaaaagagtt ggtagctctt gatccggcaa acaaaccacc gctggtagcg gtggtttttt  12000
tgtttgcaag cagcagatta cgcgcagaaa aaaaggatct caagaagatc ctttgatctt  12060
ttctacgggg tctgacgctc agtggaacga aaactcacgt taagggattt tggtcatgag  12120
attatcaaaa aggatcttca cctagatcct tttaaattaa aaatgaagtt ttaaatcaat  12180
ctaaagtata tatgagtaaa cttggtctga cagttaccaa tgcttaatca gtgaggcacc  12240
tatctcagcg atctgtctat ttcgttcatc catagttgcc tgactccccg tcgtgtagat  12300
aactacgata cgggagggct taccatctgg ccccagtgct gcaatgatac cgcgagaccc  12360
acgctcaccg gctccagatt tatcagcaat aaaccagcca gccggaaggg ccgagcgcag  12420
```

```
aagtggtcct gcaactttat ccgcctccat ccagtctatt aattgttgcc gggaagctag  12480
agtaagtagt tcgccagtta atagtttgcg caacgttgtt gccattgcta caggcatcgt  12540
ggtgtcacgc tcgtcgtttg gtatggcttc attcagctcc ggttcccaac gatcaaggcg  12600
agttacatga tcccccatgt tgtgcaaaaa agcggttagc tccttcggtc ctccgatcgt  12660
tgtcagaagt aagttggccg cagtgttatc actcatggtt atggcagcac tgcataattc  12720
tcttactgtc atgccatccg taagatgctt ttctgtgact ggtgagtact caaccaagtc  12780
attctgagaa tagtgtatgc ggcgaccgag ttgctcttgc ccggcgtcaa tacgggataa  12840
taccgcgcca catagcagaa ctttaaaagt gctcatcatt ggaaaacgtt cttcggggcg  12900
aaaactctca aggatcttac cgctgttgag atccagttcg atgtaaccca ctcgtgcacc  12960
caactgatct tcagcatctt ttactttcac cagcgtttct gggtgagcaa aaacaggaag  13020
gcaaaatgcc gcaaaaaagg gaataagggc gacacggaaa tgttgaatac tcatactctt  13080
cctttttcaa tattattgaa gcatttatca gggttattgt ctcatgagcg gatacatatt  13140
tgaatgtatt tagaaaaata aacaaatagg ggttccgcgc acatttcccc gaaaagtgcc  13200
acctgacgtc taagaaacca ttattatcat gacattaacc tataaaaata ggcgtatcac  13260
gaggcccttt cgtcttcaag aactgcctcg cgcgtttcgg tgatgacggt gaaaacctct  13320
gacacatgca gctcccggag acggtcacag cttgtctgta agcggatgcc gggagcagac  13380
aagcccgtca gggcgcgtca gcgggtgttg gcgggtgtcg gggcgcagcc atgacccagt  13440
cacgtagcga tagcggagtg tactggctta actatgcggc atcagagcag attgtactga  13500
gagtgcacca tatgcggtgt gaaataccgc acagatgcgt aaggagaaaa taccgcatca  13560
ggcgccattc gccattcagg ctgcgcaact gttgggaagg gcgatcggtg cgggcctctt  13620
cgctattacg ccaggggagg cagagattgc agtaagctga gatcgcagca ctgcactcca  13680
gcctgggcga cagagtaaga ctctgtctca aaaataaaat aaataaatca atcagatatt  13740
ccaatctttt cctttattta tttatttatt ttctattttg gaaacacagt ccttccttat  13800
tccagaatta cacatatatt ctatttttct ttatatgctc cagttttttt tagaccttca  13860
cctgaaatgt gtgtatacaa aatctaggcc agtccagcag agcctaaagg taaaaaataa  13920
aataataaaa aataaataaa atctagctca ctccttcaca tcaaaatgga gatacagctg  13980
ttagcattaa ataccaaata acccatcttg tcctcaataa ttttaagcgc ctctctccac  14040
cacatctaac tcctgtcaaa ggcatgtgcc ccttccgggc gctctgctgt gctgccaacc  14100
aactggcatg tggactctgc agggtcccta actgccaagc cccacagtgt gccctgaggc  14160
tgccccttcc ttctagcggc tgcccccact cggctttgct ttccctagtt tcagttactt  14220
gcgttcagcc aaggtctgaa actaggtgcg cacagagcgg taagactgcg agagaaagag  14280
accagcttta caggggggttt atcacagtgc accctgacag tcgtcagcct cacagggggt  14340
ttatcacatt gcaccctgac agtcgtcagc ctcacagggg gtttatcaca gtgcaccctt  14400
acaatcattc catttgattc acaatttttt tagtctctac tgtgcctaac ttgtaagtta  14460
aatttgatca gaggtgtgtt cccagagggg aaaacagtat atacagggtt cagtactatc  14520
gcatttcagg cctccacctg ggtcttggaa tgtgtccccc gaggggtgat gactacctca  14580
gttggatctc cacaggtcac agtgacacaa gataaccaag acacctccca aggctaccac  14640
aatgggccgc cctccacgtg cacatggccg gaggaactgc catgtcggag gtgcaagcac  14700
acctgcgcat cagagtcctt ggtgtggagg gagggaccag cgcagcttcc agccatccac  14760
```

```
ctgatgaaca gaacctaggg aaagccccag ttctacttac accaggaaag gc         14812


<210> SEQ ID NO 7
<211> LENGTH: 14872
<212> TYPE: DNA
<213> ORGANISM: Human immunodeficiency virus type 1

<400> SEQUENCE: 7

tggaagggct aatttggtcc caaaaaagac aagagatcct tgatctgtgg atctaccaca     60

cacaaggcta cttccctgat tggcagaact acacaccagg gccagggatc agatatccac    120

tgacctttgg atggtgcttc aagttagtac cagttgaacc agagcaagta gaagaggcca    180

aataaggaga gaagaacagc ttgttacacc ctatgagcca gcatgggatg gaggacccgg    240

agggagaagt attagtgtgg aagtttgaca gcctcctagc atttcgtcac atggcccgag    300

agctgcatcc ggagtactac aaagactgct gacatcgagc tttctacaag ggactttccg    360

ctggggactt tccagggagg tgtggcctgg gcgggactgg ggagtggcga gccctcagat    420

gctacatata agcagctgct ttttgcctgt actgggtctc tctggttaga ccagatctga    480

gcctgggagc tctctggcta actagggaac ccactgctta agcctcaata aagcttgcct    540

tgagtgctca aagtagtgtg tgcccgtctg ttgtgtgact ctggtaacta gagatccctc    600

agaccctttt agtcagtgtg gaaaatctct agcagtggcg cccgaacagg gacttgaaag    660

cgaaagtaaa gccagaggag atctctcgac gcaggactcg gcttgctgaa gcgcgcacgg    720

caagaggcga ggggcggcga ctggtgagta cgccaaaaat tttgactagc ggaggctaga    780

aggagagaga tgggtgcgag agcgtcggta ttaagcgggg gagaattaga taaatgggaa    840

aaaattcggt taaggccagg gggaaagaaa caatataaac taaaacatat agtatgggca    900

agcagggagc tagaacgatt cgcagttaat cctggccttt tagagacatc agaaggctgt    960

agacaaatac tgggacagct acaaccatcc cttcagacag gatcagaaga acttagatca   1020

ttatataata caatagcagt cctctattgt gtgcatcaaa ggatagatgt aaaagacacc   1080

aaggaagcct tagataagat agaggaagag caaaacaaaa gtaagaaaaa ggcacagcaa   1140

gcagcagctg acacaggaaa caacagccag gtcagccaaa attaccctat agtgcagaac   1200

ctccaggggc aaatggtaca tcaggccata tcacctagaa ctttaaatgc atgggtaaaa   1260

gtagtagaag agaaggcttt cagcccagaa gtaataccca tgttttcagc attatcagaa   1320

ggagccaccc cacaagattt aaataccatg ctaaacacag tggggggaca tcaagcagcc   1380

atgcaaatgt taaaagagac catcaatgag gaagctgcag aatgggatag attgcatcca   1440

gtgcatgcag ggcctattgc accaggccag atgagagaac caaggggaag tgacatagca   1500

ggaactacta gtacccttca ggaacaaata ggatggatga cacataatcc acctatccca   1560

gtaggagaaa tctataaaag atggataatc ctgggattaa ataaaatagt aagaatgtat   1620

agccctacca gcattctgga cataagacaa ggaccaaagg aaccctttag agactatgta   1680

gaccgattct ataaaactct aagagccgag caagcttcac aagaggtaaa aaattggatg   1740

acagaaacct tgttggtcca aaatgcgaac ccagattgta agactatttt aaaagcattg   1800

ggaccaggag cgacactaga agaaatgatg acagcatgtc agggagtggg gggacccggc   1860

cataaagcaa gagttttggc tgaagcaatg agccaagtaa caaatccagc taccataatg   1920

atacagaaag gcaattttag gaaccaaaga aagactgtta agtgtttcaa ttgtggcaaa   1980

gaagggcaca tagccaaaaa ttgcagggcc cctaggaaaa agggctgttg gaaatgtgga   2040

aaggaaggac accaaatgaa agattgtact gagagacagg ctaatttttt agggaagatc   2100
```

```
tggccttccc acaagggaag gccagggaat tttcttcaga gcagaccaga gccaacagcc   2160
ccaccagaag agagcttcag gtttggggaa gagacaacaa ctccctctca gaagcaggag   2220
ccgatagaca aggaactgta tcctttagct tccctcagat cactctttgg cagcgacccc   2280
tcgtcacaat aaagataggg gggcaattaa aggaagctct attagataca ggagcagatg   2340
atacagtatt agaagaaatg aatttgccag gaagatggaa accaaaaatg atagggggaa   2400
ttggaggttt tatcaaagta ggacagtatg atcagatact catagaaatc tgcggacata   2460
aagctatagg tacagtatta gtaggaccta cacctgtcaa cataattgga agaaatctgt   2520
tgactcagat tggctgcact ttaaattttc ccattagtcc tattgagact gtaccagtaa   2580
aattaaagcc aggaatggat ggcccaaaag ttaaacaatg gccattgaca gaagaaaaaa   2640
taaaagcatt agtagaaatt tgtacagaaa tggaaaagga aggaaaaatt tcaaaaattg   2700
ggcctgaaaa tccatacaat actccagtat ttgccataaa gaaaaaagac agtactaaat   2760
ggagaaaatt agtagatttc agagaactta ataagagaac tcaagatttc tgggaagttc   2820
aattaggaat accacatcct gcagggttaa aacagaaaaa atcagtaaca gtactggatg   2880
tgggcgatgc atatttttca gttcccttag ataaagactt caggaagtat actgcattta   2940
ccatacctag tataaacaat gagacaccag ggattagata tcagtacaat gtgcttccac   3000
agggatggaa aggatcacca gcaatattcc agtgtagcat gacaaaaatc ttagagcctt   3060
ttagaaaaca aaatccagac atagtcatct atcaatacat ggatgatttg tatgtaggat   3120
ctgacttaga aatagggcag catagaacaa aaatagagga actgagacaa catctgttga   3180
ggtggggatt taccacacca gacaaaaaac atcagaaaga acctccattc ctttggatgg   3240
gttatgaact ccatcctgat aaatggacag tacagcctat agtgctgcca gaaaaggaca   3300
gctggactgt caatgacata cagaaattag tgggaaaatt gaattgggca agtcagattt   3360
atgcagggat taaagtaagg caattatgta aacttcttag gggaaccaaa gcactaacag   3420
aagtagtacc actaacagaa gaagcagagc tagaactggc agaaaacagg gagattctaa   3480
aagaaccggt acatggagtg tattatgacc catcaaaaga cttaatagca gaaatacaga   3540
agcaggggca aggccaatgg acatatcaaa tttatcaaga gccatttaaa aatctgaaaa   3600
caggaaaata tgcaagaatg aagggtgccc acactaatga tgtgaaacaa ttaacagagg   3660
cagtacaaaa aatagccaca gaaagcatag taatatgggg aaagactcct aaatttaaat   3720
tacccataca aaaggaaaca tggaagcat ggtggacaga gtattggcaa gccacctgga   3780
ttcctgagtg ggagtttgtc aatacccctc ccttagtgaa gttatggtac cagttagaga   3840
aagaacccat aataggagca gaaactttct atgtagatgg ggcagccaat agggaaacta   3900
aattaggaaa agcaggatat gtaactgaca gaggaagaca aaaagttgtc cccctaacgg   3960
acacaacaaa tcagaagact gagttacaag caattcatct agctttgcag gattcgggat   4020
tagaagtaaa catagtgaca gactcacaat atgcattggg aatcattcaa gcacaaccag   4080
ataagagtga atcagagtta gtcagtcaaa taatagagca gttaataaaa aaggaaaaag   4140
tctacctggc atgggtacca gcacacaaag gaattggagg aaatgaacaa gtagatgggt   4200
tggtcagtgc tggaatcagg aaagtactat ttttagatgg aatagataag gcccaagaag   4260
aacatgagaa atatcacagt aattggagag caatggctag tgattttaac ctaccacctg   4320
tagtagcaaa agaaatagta gccagctgtg ataaatgtca gctaaaaggg gaagccatgc   4380
atggacaagt agactgtagc ccaggaatat ggcagctaga ttgtacacat ttagaaggaa   4440
```

-continued

```
aagttatctt ggtagcagtt catgtagcca gtggatatat agaagcagaa gtaattccag   4500
cagagacagg gcaagaaaca gcatacttcc tcttaaaatt agcaggaaga tggccagtaa   4560
aaacagtaca tacagacaat ggcagcaatt tcaccagtac tacagttaag gccgcctgtt   4620
ggtgggcggg gatcaagcag gaatttggca ttccctacaa tccccaaagt caaggagtaa   4680
tagaatctat gaataaagaa ttaaagaaaa ttataggaca ggtaagagat caggctgaac   4740
atcttaagac agcagtacaa atggcagtat tcatccacaa ttttaaaaga aaagggggga   4800
ttggggggta cagtgcaggg gaaagaatag tagacataat agcaacagac atacaaacta   4860
aagaattaca aaaacaaatt acaaaaattc aaaattttcg ggtttattac agggacagca   4920
gagatccagt ttggaaagga ccagcaaagc tcctctggaa aggtgaaggg gcagtagtaa   4980
tacaagataa tagtgacata aaagtagtgc caagaagaaa agcaaagatc atcagggatt   5040
atggaaaaca gatggcaggt gatgattgtg tggcaagtag acaggatgag gattaacaca   5100
tggaaaagat tagtaaaaca ccatatgtat atttcaagga aagctaagga ctggttttat   5160
agacatcact atgaaagtac taatccaaaa ataagttcag aagtacacat cccactaggg   5220
gatgctaaat tagtaataac aacatattgg ggtctgcata caggagaaag agactggcat   5280
ttgggtcagg gagtctccat agaatggagg aaaaagagat atagcacaca agtagaccct   5340
gacctagcag accaactaat tcatctgcac tattttgatt gtttttcaga atctgctata   5400
agaaatacca tattaggacg tatagttagt cctaggtgtg aatatcaagc aggacataac   5460
aaggtaggat ctctacagta cttggcacta gcagcattaa taaaaccaaa acagataaag   5520
ccacctttgc ctagtgttag gaaactgaca gaggacagat ggaacaagcc ccagaagacc   5580
aagggccaca gagggagcca tacaatgaat ggacactaga gcttttagag gaacttaaga   5640
gtgaagctgt tagacatttt cctaggatat ggctccataa cttaggacaa catatctatg   5700
aaacttacgg ggatacttgg gcaggagtgg aagccataat aagaattctg caacaactgc   5760
tgtttatcca tttcagaatt gggtgtcgac atagcagaat aggcgttact cgacagagga   5820
gagcaagaaa tggagccagt agatcctaga ctagagccct ggaagcatcc aggaagtcag   5880
cctaaaactg cttgtaccaa ttgctattgt aaaaagtgtt gctttcattg ccaagtttgt   5940
ttcatgacaa aagccttagg catctcctat ggcaggaaga agcggagaca gcgacgaaga   6000
gctcatcaga acagtcagac tcatcaagct tctctatcaa agcagtaagt agtacatgta   6060
atgcaaccta taatagtagc aatagtagca ttagtagtag caataataat agcaatagtt   6120
gtgtggtcca tagtaatcat agaatatagg aaaatattaa gacaaagaaa aatagacagg   6180
ttaattgata gactaataga aagagcagaa gacagtggca atgagagtga aggagaagta   6240
tcagcacttg tggagatggg ggtggaaatg gggcaccatg ctccttggga tattgatgat   6300
ctgtagtgct acagaaaaat tgtgggtcac cgtctattat ggggtacctg tgtggaaaga   6360
aacaaccacc actctatttt gtgcatcaga tgctaaagca tatgatacag aggtacataa   6420
tgtttgggcc acacatgcct gtgtacccac agaccccaac ccacaagaag tagtattgga   6480
aaatgtaaca gaagatttta acatgtggaa aaataacatg gtagaacaga tgcaggagga   6540
tgtaatcaat ttatgggatc aaagcttaaa gccatgtgta aaattaaccc cactctgtgt   6600
tactttaaat tgcaaagatg tgaatgctac taataccact agtagtagtg agggaatgat   6660
ggagagagga gaaataaaaa actgctcttt caatatcacc aaaagcataa gagataaggt   6720
gcagaaagaa tatgctcttt tttataaact ggatgtagta ccaatagata ataagaataa   6780
taccaaatat aggttaataa gttgtaacac ctcagtcatt acacaagcct gtccaaaggt   6840
```

```
atcctttgaa ccaattccca tacattattg tgccccggct ggttttgcga ttctaaagtg   6900
taataataag acattcaatg gaaaaggaca atgtaaaaat gtcagcacag tacaatgtac   6960
acatggaatt aggccagtag tatcaactca actgctgcta aatggcagtc tagcagaaga   7020
aaaggttgta attagatctg acaattttac ggacaatgct aaaaccataa tagtacagct   7080
gaatgaatct gtaaaaatta attgtacaag gcccagcaac aatacaagaa aaagtataca   7140
tataggacca gggagagcat tttatacaac aggagaaata ataggagata taagacaagc   7200
acattgtaac attagtagag cacaatggaa taacacttta aaacagatag ttgaaaaatt   7260
aagagaacaa tttaataata aaacaatagt ctttactcac tcctcaggag gggatccaga   7320
aattgtaatg cacagtttta attgtggagg ggaatttttc tactgtaatt caacacaact   7380
gtttaatagt acttggaatg atactgaaaa gtcaagtggc actgaaggaa atgacaccat   7440
catactccca tgcagaataa aacaaattat aaacatgtgg caggaagtgg gaaaagcaat   7500
gtatgctcct cccattaaag gacaaattag atgttcatca aatattacag ggctgctatt   7560
aacaagagat ggtggtaaaa atgagagtga gatcgagatc ttcagacctg gaggaggaga   7620
catgagggac aattggagaa gtgaattata taaatataaa gtagtaaaaa ttgaaccatt   7680
aggagtagca cccaccaagg caaagagaag agtggtgcaa agagaaaaaa gagcagtggg   7740
aataggagct ttgttccttg ggttcttggg agcagcagga agcactatgg gcgcagcgtc   7800
aatgacactg acggtacagg ccagacaatt attgtctggt atagtgcaac agcaaaacaa   7860
tttgctgagg gctattgagg cgcaacagca tatgttgcaa ctcacagtct ggggcatcaa   7920
gcagctccag gcaagagtcc tggctgtgga aagataccta aaggatcaac agctcatggg   7980
gatttggggt tgctctggaa aactcatttg caccactgct gtgccttgga atactagttg   8040
gagtaataaa tctctggata gtatttggaa taacatgacc tggatggagt gggaaaaaga   8100
aattgagaat tacacaaaca caatatacac cctaattgaa gaatcgcaga tccaacaaga   8160
aaagaatgaa caagaattat tggaattaga taaatgggca agtttgtgga attggtttgg   8220
cataacaaaa tggctgtggt atataaaaat attcataatg atagtaggag gcttgatagg   8280
tttaagaata gtttttctg tactttctat agtgaataga gttaggcagg gatactcacc   8340
cttatcgttt cagaccctcc tcccagcaac gaggggaccc gacaggcccg aaggaatcga   8400
agaagaaggt ggagagagag acagagacag atccggacaa ttagtgaacg gattcttagc   8460
acttatctgg gtcgacctgc ggagcctgtt cctcttcagc taccaccgct tgagagactt   8520
actcttgact gtaacgagga ttgtggaact tctgggacgc agggggtggg aaatcctgaa   8580
atactggtgg aatctcctac agtattggag tcaggaacta aagaatagtg ctgttagctt   8640
gcttaatgcc acagctatag cagtagctga ggggacagat aggattatag aagtagtaca   8700
aagagtttat agggctattc tccacatacc tacaagaata agacagggct tggaaagggc   8760
tttgctataa gcggccgcga tgggtggcaa gtggtcaaaa agtagtgtga ttggatggcc   8820
tgctgtaagg gaaagaatga gacgagctga gccagcagca gatggggtgg gagcagtatc   8880
tcgagaccta gaaaaacatg gagcaatcac aagtagcaat acagcagcta acaatgctgc   8940
ttgtgcctgg ctagaagcac aagaggagga agaggtgggt tttccagtca cacctcaggt   9000
acctttaaga ccaatgactt acaaggcagc tgtagatctt agccactttt taaaagaaaa   9060
ggggggactg gaagggctaa ttcactccca aagaagacaa gatatccttg atctgtggat   9120
ctaccacaca caaggctact tccctgattg gcagaactac acaccagggc caggggtcag   9180
```

```
atatccactg acctttggat ggtgctacaa gctagtacca gttgagccag ataaggtaga   9240
agaggccaat aaaggagaga acaccagctt gttacaccct gtgagcctgc atggaatgga   9300
tgaccctgag agagaagtgt tagagtggag gtttgacagc cgcctagcat ttcatcacgt   9360
ggcccgagag ctgcatccgg agtacttcaa gaactgctga catcgagctt gctacaaggg   9420
actttccgct ggggactttc cagggaggcg tggcctgggc gggactgggg agtggcgagc   9480
cctcagatgc tgcatataag cagctgcttt ttgcctgtac tgggtctctc tggttagacc   9540
agatctgagc ctgggagctc tctggctaac tagggaaccc actgcttaag cctcaataaa   9600
gcttgccttg agtgcttcaa gtagtgtgtg cccgtctgtt gtgtgactct ggtaactaga   9660
gatccctcag acccttttag tcagtgtgga aaatctctag caccccccag gaggtagagg   9720
ttgcagtgag ccaagatcgc gccactgcat tccagcctgg gcaagaaaac aagactgtct   9780
aaaataataa taataagtta agggtattaa atatatttat acatggaggt cataaaaata   9840
tatatatttg ggctgggcgc agtggctcac acctgcgccc ggccctttgg gaggccgagg   9900
caggtggatc acctgagttt gggagttcca gaccagcctg accaacatgg agaaacccct   9960
tctctgtgta tttttagtag attttatttt atgtgtattt tattcacagg tatttctgga  10020
aaactgaaac tgtttttcct ctactctgat accacaagaa tcatcagcac agaggaagac  10080
ttctgtgatc aaatgtggtg ggagagggag gttttcacca gcacatgagc agtcagttct  10140
gccgcagact cggcgggtgt ccttcggttc agttccaaca ccgcctgcct ggagagaggt  10200
cagaccacag ggtgagggct cagtccccaa gacataaaca cccaagacat aaacacccaa  10260
caggtccacc ccgcctgctg cccaggcaga gccgattcac caagacggga attaggatag  10320
agaaagagta agtcacacag agccggctgt gcgggagaac ggagttctat tatgactcaa  10380
atcagtctcc ccaagcattc ggggatcaga gtttttaagg ataacttagt gtgtaggggg  10440
ccagtgagtt ggagatgaaa gcgtagggag tcgaaggtgt ccttttgcgc cgagtcagtt  10500
cctgggtggg ggccacaaga tcggatgagc cagtttatca atccgggggt gccagctgat  10560
ccatggagtg cagggtctgc aaaatatctc aagcactgat tgatcttagg ttttacaata  10620
gtgatgttac cccaggaaca atttggggaa ggtcagaatc ttgtagcctg tagctgcatg  10680
actcctaaac cataatttct tttttgtttt ttttttttta tttttgagac agggtctcac  10740
tctgtcacct aggctggagt gcagtggtgc aatcacagct cactgcagcc tcaacgtcgt  10800
aagctcaagc gatcctccca cctcagcctg cctggtagct gagactacaa gcgacgcccc  10860
agttaatttt tgtatttttg gtagaggcag cgttttgccg tgtggccctg gctggtctcg  10920
aactcctggg ctcaagtgat ccagcctcag cctcccaaag tgctgggaca accggggcca  10980
gtcactgcac ctggccctaa accataattt ctaatctttt ggctaatttg ttagtcctac  11040
aaaggcagtc tagtccccag gcaaaaaggg ggtttgtttc gggaaagggc tgttactgtc  11100
tttgtttcaa actataaact aagttcctcc taaacttagt tcggcctaca cccaggaatg  11160
aacaaggaga gcttggaggt tagaagcacg atggaattgg ttaggtcaga tctctttcac  11220
tgtctgagtt ataattttgc aatggtggtt caaagactgc ccgcttctga caccagtcgc  11280
tgcattaatg aatcggccaa cgcgcgggga gaggcggttt gcgtattggc gctcttccgc  11340
ttcctcgctc actgactcgc tgcgctcggt cgttcggctg cggcgagcgg tatcagctca  11400
ctcaaaggcg gtaatacggt tatccacaga atcaggggat aacgcaggaa agaacatgtg  11460
agcaaaaggc cagcaaaagg ccaggaaccg taaaaaggcc gcgttgctgg cgtttttcca  11520
taggctccgc ccccctgacg agcatcacaa aaatcgacgc tcaagtcaga ggtggcgaaa  11580
```

```
cccgacagga ctataaagat accaggcgtt tccccctgga agctccctcg tgcgctctcc  11640

tgttccgacc ctgccgctta ccggatacct gtccgccttt ctcccttcgg gaagcgtggc  11700

gctttctcaa tgctcacgct gtaggtatct cagttcggtg taggtcgttc gctccaagct  11760

gggctgtgtg cacgaacccc ccgttcagcc cgaccgctgc gccttatccg gtaactatcg  11820

tcttgagtcc aacccggtaa gacacgactt atcgccactg gcagcagcca ctggtaacag  11880

gattagcaga gcgaggtatg taggcggtgc tacagagttc ttgaagtggt ggcctaacta  11940

cggctacact agaaggacag tatttggtat ctgcgctctg ctgaagccag ttaccttcgg  12000

aaaaagagtt ggtagctctt gatccggcaa acaaaccacc gctggtagcg gtggtttttt  12060

tgtttgcaag cagcagatta cgcgcagaaa aaaaggatct caagaagatc ctttgatctt  12120

ttctacgggg tctgacgctc agtggaacga aaactcacgt taagggattt tggtcatgag  12180

attatcaaaa aggatcttca cctagatcct tttaaattaa aaatgaagtt ttaaatcaat  12240

ctaaagtata tatgagtaaa cttggtctga cagttaccaa tgcttaatca gtgaggcacc  12300

tatctcagcg atctgtctat ttcgttcatc catagttgcc tgactccccg tcgtgtagat  12360

aactacgata cgggagggct taccatctgg ccccagtgct gcaatgatac cgcgagaccc  12420

acgctcaccg gctccagatt tatcagcaat aaaccagcca gccggaaggg ccgagcgcag  12480

aagtggtcct gcaactttat ccgcctccat ccagtctatt aattgttgcc gggaagctag  12540

agtaagtagt tcgccagtta atagtttgcg caacgttgtt gccattgcta caggcatcgt  12600

ggtgtcacgc tcgtcgtttg gtatggcttc attcagctcc ggttcccaac gatcaaggcg  12660

agttacatga tcccccatgt tgtgcaaaaa agcggttagc tccttcggtc ctccgatcgt  12720

tgtcagaagt aagttggccg cagtgttatc actcatggtt atggcagcac tgcataattc  12780

tcttactgtc atgccatccg taagatgctt ttctgtgact ggtgagtact caaccaagtc  12840

attctgagaa tagtgtatgc ggcgaccgag ttgctcttgc ccggcgtcaa tacgggataa  12900

taccgcgcca catagcagaa ctttaaaagt gctcatcatt ggaaaacgtt cttcggggcg  12960

aaaactctca aggatcttac cgctgttgag atccagttcg atgtaaccca ctcgtgcacc  13020

caactgatct tcagcatctt ttactttcac cagcgtttct gggtgagcaa aaacaggaag  13080

gcaaaatgcc gcaaaaaagg gaataagggc gacacggaaa tgttgaatac tcatactctt  13140

cctttttcaa tattattgaa gcatttatca gggttattgt ctcatgagcg gatacatatt  13200

tgaatgtatt tagaaaaata aacaaatagg ggttccgcgc acatttcccc gaaaagtgcc  13260

acctgacgtc taagaaacca ttattatcat gacattaacc tataaaaata ggcgtatcac  13320

gaggcccttt cgtcttcaag aactgcctcg cgcgtttcgg tgatgacggt gaaaacctct  13380

gacacatgca gctcccggag acggtcacag cttgtctgta agcggatgcc gggagcagac  13440

aagcccgtca gggcgcgtca gcgggtgttg gcgggtgtcg gggcgcagcc atgacccagt  13500

cacgtagcga tagcggagtg tactggctta actatgcggc atcagagcag attgtactga  13560

gagtgcacca tatgcggtgt gaaataccgc acagatgcgt aaggagaaaa taccgcatca  13620

ggcgccattc gccattcagg ctgcgcaact gttgggaagg gcgatcggtg cgggcctctt  13680

cgctattacg ccaggggagg cagagattgc agtaagctga gatcgcagca ctgcactcca  13740

gcctgggcga cagagtaaga ctctgtctca aaaataaaat aaataaatca atcagatatt  13800

ccaatctttt cctttattta tttatttatt ttctattttg gaaacacagt ccttccttat  13860

tccagaatta cacatatatt ctatttttct ttatatgctc cagttttttt tagaccttca  13920
```

```
cctgaaatgt gtgtatacaa aatctaggcc agtccagcag agcctaaagg taaaaaataa  13980
aataataaaa aataaataaa atctagctca ctccttcaca tcaaaatgga gatacagctg  14040
ttagcattaa ataccaaata acccatcttg tcctcaataa ttttaagcgc ctctctccac  14100
cacatctaac tcctgtcaaa ggcatgtgcc ccttccgggc gctctgctgt gctgccaacc  14160
aactggcatg tggactctgc agggtcccta actgccaagc cccacagtgt gccctgaggc  14220
tgccccttcc ttctagcggc tgcccccact cggctttgct ttccctagtt tcagttactt  14280
gcgttcagcc aaggtctgaa actaggtgcg cacagagcgg taagactgcg agagaaagag  14340
accagcttta caggggggttt atcacagtgc accctgacag tcgtcagcct cacagggggt  14400
ttatcacatt gcaccctgac agtcgtcagc ctcacagggg gtttatcaca gtgcaccctt  14460
acaatcattc catttgattc acaatttttt tagtctctac tgtgcctaac ttgtaagtta  14520
aatttgatca gaggtgtgtt cccagagggg aaaacagtat atacagggtt cagtactatc  14580
gcatttcagg cctccacctg ggtcttggaa tgtgtccccc gaggggtgat gactacctca  14640
gttggatctc cacaggtcac agtgacacaa gataaccaag acacctccca aggctaccac  14700
aatgggccgc cctccacgtg cacatggccg gaggaactgc catgtcggag gtgcaagcac  14760
acctgcgcat cagagtcctt ggtgtggagg gagggaccag cgcagcttcc agccatccac  14820
ctgatgaaca gaacctaggg aaagccccag ttctacttac accaggaaag gc          14872
```

<210> SEQ ID NO 8
<211> LENGTH: 14976
<212> TYPE: DNA
<213> ORGANISM: Human immunodeficiency virus type 1

<400> SEQUENCE: 8

```
tggaagggct aatttggtcc caaaaaagac aagagatcct tgatctgtgg atctaccaca     60
cacaaggcta cttccctgat tggcagaact acacaccagg gccagggatc agatatccac    120
tgacctttgg atggtgcttc aagttagtac cagttgaacc agagcaagta gaagaggcca    180
aataaggaga gaagaacagc ttgttacacc ctatgagcca gcatgggatg gaggacccgg    240
agggagaagt attagtgtgg aagtttgaca gcctcctagc atttcgtcac atggcccgag    300
agctgcatcc ggagtactac aaagactgct gacatcgagc tttctacaag ggactttccg    360
ctggggactt tccagggagg tgtggcctgg gcgggactgg ggagtggcga gccctcagat    420
gctacatata agcagctgct tttgcctgt actgggtctc tctggttaga ccagatctga    480
gcctgggagc tctctggcta actagggaac ccactgctta agcctcaata aagcttgcct    540
tgagtgctca aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagtaaa gccagaggag atctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcggta ttaagcgggg gagaattaga taaatgggaa    840
aaaattcggt taaggccagg gggaaagaaa caatataaac taaaacatat agtatgggca    900
agcagggagc tagaacgatt cgcagttaat cctggccttt tagagacatc agaaggctgt    960
agacaaatac tgggacagct acaaccatcc cttcagacag gatcagaaga acttagatca   1020
ttatataata caatagcagt cctctattgt gtgcatcaaa ggatagatgt aaaagacacc   1080
aaggaagcct tagataagat agaggaagag caaaacaaaa gtaagaaaaa ggcacagcaa   1140
gcagcagctg acacaggaaa caacagccag gtcagccaaa attaccctat agtgcagaac   1200
```

```
ctccaggggc aaatggtaca tcaggccata tcacctagaa ctttaaatgc atgggtaaaa   1260
gtagtagaag agaaggcttt cagcccagaa gtaataccca tgttttcagc attatcagaa   1320
ggagccaccc cacaagattt aaataccatg ctaaacacag tggggggaca tcaagcagcc   1380
atgcaaatgt taaaagagac catcaatgag gaagctgcag aatgggatag attgcatcca   1440
gtgcatgcag ggcctattgc accaggccag atgagagaac caaggggaag tgacatagca   1500
ggaactacta gtacccttca ggaacaaata ggatggatga cacataatcc acctatccca   1560
gtaggagaaa tctataaaag atggataatc ctgggattaa ataaaatagt aagaatgtat   1620
agccctacca gcattctgga cataagacaa ggaccaaagg aaccctttag agactatgta   1680
gaccgattct ataaaactct aagagccgag caagcttcac aagaggtaaa aaattggatg   1740
acagaaacct tgttggtcca aaatgcgaac ccagattgta agactatttt aaaagcattg   1800
ggaccaggag cgacactaga agaaatgatg acagcatgtc agggagtggg gggacccggc   1860
cataaagcaa gagttttggc tgaagcaatg agccaagtaa caaatccagc taccataatg   1920
atacagaaag gcaattttag gaaccaaaga aagactgtta agtgtttcaa ttgtggcaaa   1980
gaagggcaca tagccaaaaa ttgcagggcc cctaggaaaa agggctgttg gaaatgtgga   2040
aaggaaggac accaaatgaa agattgtact gagagacagg ctaatttttt agggaagatc   2100
tggccttccc acaagggaag gccagggaat tttcttcaga gcagaccaga gccaacagcc   2160
ccaccagaag agagcttcag gtttggggaa gagacaacaa ctccctctca gaagcaggag   2220
ccgatagaca aggaactgta tcctttagct tccctcagat cactctttgg cagcgacccc   2280
tcgtcacaat aaagataggg gggcaattaa aggaagctct attagataca ggagcagatg   2340
atacagtatt agaagaaatg aatttgccag gaagatggaa accaaaaatg atagggggaa   2400
ttggaggttt tatcaaagta ggacagtatg atcagatact catagaaatc tgcggacata   2460
aagctatagg tacagtatta gtaggaccta cacctgtcaa cataattgga agaaatctgt   2520
tgactcagat tggctgcact ttaaattttc ccattagtcc tattgagact gtaccagtaa   2580
aattaaagcc aggaatggat ggcccaaaag ttaaacaatg gccattgaca gaagaaaaaa   2640
taaaagcatt agtagaaatt tgtacagaaa tggaaaagga aggaaaaatt tcaaaaattg   2700
ggcctgaaaa tccatacaat actccagtat ttgccataaa gaaaaaagac agtactaaat   2760
ggagaaaatt agtagatttc agagaactta ataagagaac tcaagatttc tgggaagttc   2820
aattaggaat accacatcct gcagggttaa aacagaaaaa atcagtaaca gtactggatg   2880
tgggcgatgc atatttttca gttcccttag ataaagactt caggaagtat actgcattta   2940
ccatacctag tataaacaat gagacaccag ggattagata tcagtacaat gtgcttccac   3000
agggatggaa aggatcacca gcaatattcc agtgtagcat gacaaaaatc ttagagcctt   3060
ttagaaaaca aaatccagac atagtcatct atcaatacat ggatgatttg tatgtaggat   3120
ctgacttaga aatagggcag catagaacaa aaatagagga actgagacaa catctgttga   3180
ggtggggatt taccacacca gacaaaaaac atcagaaaga acctccattc ctttggatgg   3240
gttatgaact ccatcctgat aaatggacag tacagcctat agtgctgcca gaaaaggaca   3300
gctggactgt caatgacata cagaaattag tgggaaaatt gaattgggca agtcagattt   3360
atgcagggat taaagtaagg caattatgta aacttcttag gggaaccaaa gcactaacag   3420
aagtagtacc actaacagaa gaagcagagc tagaactggc agaaaacagg gagattctaa   3480
aagaaccggt acatggagtg tattatgacc catcaaaaga cttaatagca gaaatacaga   3540
```

```
agcaggggca aggccaatgg acatatcaaa tttatcaaga gccatttaaa aatctgaaaa   3600
caggaaaata tgcaagaatg aagggtgccc acactaatga tgtgaaacaa ttaacagagg   3660
cagtacaaaa aatagccaca gaaagcatag taatatgggg aaagactcct aaatttaaat   3720
tacccataca aaaggaaaca tgggaagcat ggtggacaga gtattggcaa gccacctgga   3780
ttcctgagtg ggagtttgtc aataccoctc ccttagtgaa gttatggtac cagttagaga   3840
aagaacccat aataggagca gaaactttct atgtagatgg ggcagccaat agggaaacta   3900
aattaggaaa agcaggatat gtaactgaca gaggaagaca aaaagttgtc cccctaacgg   3960
acacaacaaa tcagaagact gagttacaag caattcatct agctttgcag gattcgggat   4020
tagaagtaaa catagtgaca gactcacaat atgcattggg aatcattcaa gcacaaccag   4080
ataagagtga atcagagtta gtcagtcaaa taatagagca gttaataaaa aaggaaaaag   4140
tctacctggc atgggtacca gcacacaaag gaattggagg aaatgaacaa gtagatgggt   4200
tggtcagtgc tggaatcagg aaagtactat ttttagatgg aatagataag gcccaagaag   4260
aacatgagaa atatcacagt aattggagag caatggctag tgattttaac ctaccacctg   4320
tagtagcaaa agaaatagta gccagctgtg ataaatgtca gctaaaaggg gaagccatgc   4380
atggacaagt agactgtagc ccaggaatat ggcagctaga ttgtacacat ttagaaggaa   4440
aagttatctt ggtagcagtt catgtagcca gtggatatat agaagcagaa gtaattccag   4500
cagagacagg gcaagaaaca gcatacttcc tcttaaaatt agcaggaaga tggccagtaa   4560
aaacagtaca tacagacaat ggcagcaatt tcaccagtac tacagttaag gccgcctgtt   4620
ggtgggcggg gatcaagcag gaatttggca ttccctacaa tccccaaagt caaggagtaa   4680
tagaatctat gaataaagaa ttaaagaaaa ttataggaca ggtaagagat caggctgaac   4740
atcttaagac agcagtacaa atggcagtat tcatccacaa ttttaaaaga aaagggggga   4800
ttggggggta cagtgcaggg gaaagaatag tagacataat agcaacagac atacaaacta   4860
aagaattaca aaaacaaatt acaaaaattc aaaattttcg ggtttattac agggacagca   4920
gagatccagt ttggaaagga ccagcaaagc tcctctggaa aggtgaaggg gcagtagtaa   4980
tacaagataa tagtgacata aaagtagtgc caagaagaaa agcaaagatc atcagggatt   5040
atggaaaaca gatggcaggt gatgattgtg tggcaagtag acaggatgag gattaacaca   5100
tggaaaagat tagtaaaaca ccatatgtat atttcaagga aagctaagga ctggttttat   5160
agacatcact atgaaagtac taatccaaaa ataagttcag aagtacacat cccactaggg   5220
gatgctaaat tagtaataac aacatattgg ggtctgcata caggagaaag agactggcat   5280
ttgggtcagg gagtctccat agaatggagg aaaaagagat atagcacaca agtagaccct   5340
gacctagcag accaactaat tcatctgcac tattttgatt gtttttcaga atctgctata   5400
agaaatacca tattaggacg tatagttagt cctaggtgtg aatatcaagc aggacataac   5460
aaggtaggat ctctacagta cttggcacta gcagcattaa taaaaccaaa acagataaag   5520
ccacctttgc ctagtgttag gaaactgaca gaggacagat ggaacaagcc ccagaagacc   5580
aagggccaca gagggagcca tacaatgaat ggacactaga gcttttagag gaacttaaga   5640
gtgaagctgt tagacatttt cctaggatat ggctccataa cttaggacaa catatctatg   5700
aaacttacgg ggatacttgg gcaggagtgg aagccataat aagaattctg caacaactgc   5760
tgtttatcca tttcagaatt gggtgtcgac atagcagaat aggcgttact cgacagagga   5820
gagcaagaaa tggagccagt agatcctaga ctagagccct ggaagcatcc aggaagtcag   5880
cctaaaactg cttgtaccaa ttgctattgt aaaaagtgtt gctttcattg ccaagtttgt   5940
```

ttcatgacaa aagccttagg catctcctat ggcaggaaga agcggagaca gcgacgaaga 6000
gctcatcaga acagtcagac tcatcaagct tctctatcaa agcagtaagt agtacatgta 6060
atgcaaccta taatagtagc aatagtagca ttagtagtag caataataat agcaatagtt 6120
gtgtggtcca tagtaatcat agaatatagg aaaatattaa gacaaagaaa aatagacagg 6180
ttaattgata gactaataga aagagcagaa gacagtggca atgagagtga aggagaagta 6240
tcagcacttg tggagatggg ggtggaaatg gggcaccatg ctccttggga tattgatgat 6300
ctgtagtgct acagaaaaat tgtgggtcac cgtctattat ggggtacctg tgtggaaaga 6360
agcaaccacc actctatttt gtgcatcaga tgctaaagca tatgatacag aggtacataa 6420
tgtttgggcc acacatgcct gtgtacccac agaccccaac ccacaagaag tagtattgga 6480
aaatgtaaca gaacatttta acatgtggaa aaataacatg gtagaacaga tgcaggagga 6540
tataatcagt ttatgggatc aaagcctaaa gccatgtgta aaattaaccc cactctgtgt 6600
tactttaaat tgcaaggatg tgaatgctac taataccact aatgatagcg agggaacgat 6660
ggagagagga gaaataaaaa actgctcttt caatatcacc acaagcataa gagatgaggt 6720
gcagaaagaa tatgctcttt tttataaact tgatgtagta ccaatagata ataataatac 6780
cagctatagg ttgataagtt gtgacacctc agtcattaca caggcctgtc caaagatatc 6840
ctttgagcca attcccatac attattgtgc cccggctggt tttgcgattc taaagtgtaa 6900
tgataagacg ttcaatggaa aaggaccatg taaaaatgtc agcacagtac aatgtacaca 6960
tggaattagg ccagtagtat caactcaact gctgctaaat ggcagtctag cagaagaaga 7020
ggtagtaatt agatctgaca atttcacgaa caatgctaaa accataatag tacagctgaa 7080
agaatctgta gaaattaatt gtacaagacc caacaacaat acaagaaaaa gtatacatat 7140
aggaccaggg agagcatttt atactacagg agaaataata ggagatataa gacaagcaca 7200
ttgtaacatt agtagagcaa aatggaatga cactttaaaa cagatagtta taaaattaag 7260
agaacaattt gagaataaaa caatagtctt taatcactcc tcaggagggg acccagaaat 7320
tgtaatgcac agttttaatt gtggaggaga atttttctac tgtaattcaa cacaactgtt 7380
taatagtact tggaataata atactgaagg gtcaaataac actgaaggaa atactatcac 7440
actcccatgc agaataaaac aaattataaa catgtggcag gaagtaggaa aagcaatgta 7500
tgcccctccc atcagaggac aaattagatg ttcatcaaat attacagggc tgctattaac 7560
aagagatggt ggtattaatg agaatgggac cgagatcttc agacctggag gaggagatat 7620
gagggacaat tggagaagtg aattatataa atataaagta gtaaaaattg aaccattagg 7680
agtagcaccc accaaggcaa agagaagagt ggtgcaaaga gaaaaaagag cagtgggaat 7740
aggagctgtg ttccttgggt tcttgggagc agcaggaagc actatgggcg cagcgtcaat 7800
gacactgacg gtacaggcca gactattatt gtctggtata gtgcaacagc agaacaattt 7860
gctgagggct attgaggcgc aacagcgtat gttgcaactc acagtctggg gcatcaagca 7920
gctccaggca agagtcctgg ctgtggaaag atacctaggg gatcaacagc tcctggggat 7980
ttggggttgc tctggaaaac tcatttgcac cactgctgtg ccttggaatg ctagttggag 8040
taataaatct ctggatagga tttggaataa catgacctgg atggagtggg aaagagaaat 8100
tgacaattac acaagcgaaa tatacaccct aattgaagaa tcgcagaacc aacaagaaaa 8160
gaatgaacaa gaattattgg aattagataa atgggcaagt ttgtggaatt ggtttgacat 8220
aacaaaatgg ctgtggtata taaaaatatt cataatgata gtaggaggct tagtaggttt 8280

-continued

```
aagactagtt tttactgtac tttctatagt gaatagagtt aggcagggat actcaccatt   8340
atcgtttcag accctcctcc cagccccgag gggacccgac aggcccgaag gaatcgaaga   8400
agaaggtgga gagagagaca gagacagatc cggacgatta gtgaacggat tcttagcact   8460
tatctgggtc gacctgcgga gcctgtgcct cttcagctac caccgcttga gagacttact   8520
cttgactgta acgaggattg tggaacttct gggacgcagg gggtgggaag tcctgaaata   8580
ttggtggaat ctcctacagt attggagtca ggaactaaag aatagtgctg ttagcttgct   8640
caatgccaca gccatagcag tagctgaggg gacagatagg attatagaag cattacaaag   8700
aacttataga gctattctcc acatacctac aagaataaga cagggcttgg aaagggcttt   8760
gctataagcg gccgcaatga gcgacccaag agagagaatc ccaccaggca atagcggcga   8820
agaaacaatc ggagaggctt ttgaatggct gaacaggacc gtcgaggaaa tcaaccggga   8880
ggcagtgaat cacctgccta gagaactgat tttccaggtc tggcagcgat cttgggagta   8940
ctggcatgac gaacagggga tgagccagtc ctatgtgaag tacagatatc tgtgcctgat   9000
gcagaaagcc ctgtttatgc actgtaagaa aggctgcagg tgtctgggag agggccatgg   9060
ggccggcggg tggcgccccg gaccccctcc accccctcca cccggcctgg cttgacccgg   9120
gtacctttaa gaccaatgac ttacaaggca gctgtagatc ttagccactt tttaaaagaa   9180
aaggggggac tggaagggct aattcactcc caaagaagac aagatatcct tgatctgtgg   9240
atctaccaca cacaaggcta cttccctgat tggcagaact acacaccagg gccaggggtc   9300
agatatccac tgacctttgg atggtgctac aagctagtac cagttgagcc agataaggta   9360
gaagaggcca ataaaggaga gaacaccagc ttgttacacc ctgtgagcct gcatggaatg   9420
gatgaccctg agagagaagt gttacgccta gcatttcatc acgtggcccg agagctgcat   9480
ccggagtact tcaagaactg ctgacatcga gcttgctaca agggactttc cgctggggac   9540
tttccaggga ggcgtggcct gggcgggact ggggagtggc gagccctcag atgctgcata   9600
taagcagctg ctttttgcct gtactgggtc tctctggtta gaccagatct gagcctggga   9660
gctctctggc taactaggga acccactgct taagcctcaa taaagcttgc cttgagtgct   9720
tcaagtagtg tgtgcccgtc tgttgtgtga ctctggtaac tagagatccc tcagaccctt   9780
ttagtcagtg tggaaaatct ctagcacccc ccaggaggta gaggttgcag tgagccaaga   9840
tcgcgccact gcattccagc ctgggcaaga aaacaagact gtctaaaata ataataataa   9900
gttaagggta ttaaatatat ttatacatgg aggtcataaa aatatatata tttgggctgg   9960
gcgcagtggc tcacacctgc gcccggccct ttgggaggcc gaggcaggtg gatcacctga  10020
gtttgggagt tccagaccag cctgaccaac atggagaaac cccttctctg tgtattttta  10080
gtagatttta ttttatgtgt attttattca caggtatttc tggaaaactg aaactgtttt  10140
tcctctactc tgataccaca agaatcatca gcacagagga agacttctgt gatcaaatgt  10200
ggtgggagag ggaggttttc accagcacat gagcagtcag ttctgccgca gactcggcgg  10260
gtgtccttcg gttcagttcc aacaccgcct gcctggagag aggtcagacc acagggtgag  10320
ggctcagtcc ccaagacata aacacccaag acataaacac ccaacaggtc caccccgcct  10380
gctgcccagg cagagccgat tcaccaagac gggaattagg atagagaaag agtaagtcac  10440
acagagccgg ctgtgcggga gaacggagtt ctattatgac tcaaatcagt ctccccaagc  10500
attcggggat cagagttttt aaggataact tagtgtgtag gggccagtg agttggagat  10560
gaaagcgtag ggagtcgaag gtgtcctttt gcgccgagtc agttcctggg tgggggccac  10620
aagatcggat gagccagttt atcaatccgg gggtgccagc tgatccatgg agtgcagggt  10680
```

```
ctgcaaaata tctcaagcac tgattgatct taggttttac aatagtgatg ttaccccagg  10740
aacaatttgg ggaaggtcag aatcttgtag cctgtagctg catgactcct aaaccataat  10800
ttcttttttg tttttttttt tttatttttg agacagggtc tcactctgtc acctaggctg  10860
gagtgcagtg gtgcaatcac agctcactgc agcctcaacg tcgtaagctc aagcgatcct  10920
cccacctcag cctgcctggt agctgagact acaagcgacg ccccagttaa tttttgtatt  10980
tttggtagag gcagcgtttt gccgtgtggc cctggctggt ctcgaactcc tgggctcaag  11040
tgatccagcc tcagcctccc aaagtgctgg gacaaccggg gccagtcact gcacctggcc  11100
ctaaaccata atttctaatc ttttggctaa tttgttagtc ctacaaaggc agtctagtcc  11160
ccaggcaaaa agggggtttg tttcgggaaa gggctgttac tgtctttgtt tcaaactata  11220
aactaagttc ctcctaaact tagttcggcc tacacccagg aatgaacaag gagagcttgg  11280
aggttagaag cacgatggaa ttggttaggt cagatctctt tcactgtctg agttataatt  11340
ttgcaatggt ggttcaaaga ctgcccgctt ctgacaccag tcgctgcatt aatgaatcgg  11400
ccaacgcgcg gggagaggcg gtttgcgtat tggcgctctt ccgcttcctc gctcactgac  11460
tcgctgcgct cggtcgttcg gctgcggcga gcggtatcag ctcactcaaa ggcggtaata  11520
cggttatcca cagaatcagg ggataacgca ggaaagaaca tgtgagcaaa aggccagcaa  11580
aaggccagga accgtaaaaa ggccgcgttg ctggcgtttt tccataggct ccgcccccct  11640
gacgagcatc acaaaaatcg acgctcaagt cagaggtggc gaaacccgac aggactataa  11700
agataccagg cgtttccccc tggaagctcc ctcgtgcgct ctcctgttcc gaccctgccg  11760
cttaccggat acctgtccgc ctttctccct tcgggaagcg tggcgctttc tcaatgctca  11820
cgctgtaggt atctcagttc ggtgtaggtc gttcgctcca agctgggctg tgtgcacgaa  11880
ccccccgttc agcccgaccg ctgcgcctta tccggtaact atcgtcttga gtccaacccg  11940
gtaagacacg acttatcgcc actggcagca gccactggta acaggattag cagagcgagg  12000
tatgtaggcg gtgctacaga gttcttgaag tggtggccta actacggcta cactagaagg  12060
acagtatttg gtatctgcgc tctgctgaag ccagttacct tcggaaaaag agttggtagc  12120
tcttgatccg gcaaacaaac caccgctggt agcggtggtt tttttgtttg caagcagcag  12180
attacgcgca gaaaaaaagg atctcaagaa gatcctttga tcttttctac ggggtctgac  12240
gctcagtgga acgaaaactc acgttaaggg attttggtca tgagattatc aaaaaggatc  12300
ttcacctaga tccttttaaa ttaaaaatga agttttaaat caatctaaag tatatatgag  12360
taaacttggt ctgacagtta ccaatgctta atcagtgagg cacctatctc agcgatctgt  12420
ctatttcgtt catccatagt tgcctgactc cccgtcgtgt agataactac gatacgggag  12480
ggcttaccat ctggccccag tgctgcaatg ataccgcgag acccacgctc accggctcca  12540
gatttatcag caataaacca gccagccgga agggccgagc gcagaagtgg tcctgcaact  12600
ttatccgcct ccatccagtc tattaattgt tgccgggaag ctagagtaag tagttcgcca  12660
gttaatagtt tgcgcaacgt tgttgccatt gctacaggca tcgtggtgtc acgctcgtcg  12720
tttggtatgg cttcattcag ctccggttcc caacgatcaa ggcgagttac atgatccccc  12780
atgttgtgca aaaaagcggt tagctccttc ggtcctccga tcgttgtcag aagtaagttg  12840
gccgcagtgt tatcactcat ggttatggca gcactgcata attctcttac tgtcatgcca  12900
tccgtaagat gcttttctgt gactggtgag tactcaacca agtcattctg agaatagtgt  12960
atgcggcgac cgagttgctc ttgcccggcg tcaatacggg ataataccgc gccacatagc  13020
```

```
agaactttaa aagtgctcat cattggaaaa cgttcttcgg ggcgaaaact ctcaaggatc  13080

ttaccgctgt tgagatccag ttcgatgtaa cccactcgtg cacccaactg atcttcagca  13140

tcttttactt tcaccagcgt ttctgggtga gcaaaaacag gaaggcaaaa tgccgcaaaa  13200

aagggaataa gggcgacacg gaaatgttga atactcatac tcttcctttt tcaatattat  13260

tgaagcattt atcagggtta ttgtctcatg agcggataca tatttgaatg tatttagaaa  13320

aataaacaaa taggggttcc gcgcacattt ccccgaaaag tgccacctga cgtctaagaa  13380

accattatta tcatgacatt aacctataaa aataggcgta tcacgaggcc ctttcgtctt  13440

caagaactgc ctcgcgcgtt tcggtgatga cggtgaaaac ctctgacaca tgcagctccc  13500

ggagacggtc acagcttgtc tgtaagcgga tgccgggagc agacaagccc gtcagggcgc  13560

gtcagcgggt gttggcgggt gtcggggcgc agccatgacc cagtcacgta gcgatagcgg  13620

agtgtactgg cttaactatg cggcatcaga gcagattgta ctgagagtgc accatatgcg  13680

gtgtgaaata ccgcacagat gcgtaaggag aaaataccgc atcaggcgcc attcgccatt  13740

caggctgcgc aactgttggg aagggcgatc ggtgcgggcc tcttcgctat tacgccaggg  13800

gaggcagaga ttgcagtaag ctgagatcgc agcactgcac tccagcctgg gcgacagagt  13860

aagactctgt ctcaaaaata aaataaataa atcaatcaga tattccaatc ttttccttta  13920

tttatttatt tattttctat tttggaaaca cagtccttcc ttattccaga attacacata  13980

tattctattt ttctttatat gctccagttt tttttagacc ttcacctgaa atgtgtgtat  14040

acaaaatcta ggccagtcca gcagagccta aaggtaaaaa ataaaataat aaaaaataaa  14100

taaaatctag ctcactcctt cacatcaaaa tggagataca gctgttagca ttaaatacca  14160

aataacccat cttgtcctca ataattttaa gcgcctctct ccaccacatc taactcctgt  14220

caaaggcatg tgccccttcc gggcgctctg ctgtgctgcc aaccaactgg catgtggact  14280

ctgcagggtc cctaactgcc aagccccaca gtgtgccctg aggctgcccc ttccttctag  14340

cggctgcccc cactcggctt tgctttccct agtttcagtt acttgcgttc agccaaggtc  14400

tgaaactagg tgcgcacaga gcggtaagac tgcgagagaa agagaccagc tttacagggg  14460

gtttatcaca gtgcaccctg acagtcgtca gcctcacagg gggtttatca cattgcaccc  14520

tgacagtcgt cagcctcaca gggggtttat cacagtgcac ccttacaatc attccatttg  14580

attcacaatt tttttagtct ctactgtgcc taacttgtaa gttaaatttg atcagaggtg  14640

tgttcccaga ggggaaaaca gtatatacag ggttcagtac tatcgcattt caggcctcca  14700

cctgggtctt ggaatgtgtc cccgaggggg tgatgactac ctcagttgga tctccacagg  14760

tcacagtgac acaagataac caagacacct cccaaggcta ccacaatggg ccgccctcca  14820

cgtgcacatg gccggaggaa ctgccatgtc ggaggtgcaa gcacacctgc gcatcagagt  14880

ccttggtgtg gagggaggga ccagcgcagc ttccagccat ccacctgatg aacagaacct  14940

agggaaagcc ccagttctac ttacaccagg aaaggc                            14976
```

```
<210> SEQ ID NO 9
<211> LENGTH: 14997
<212> TYPE: DNA
<213> ORGANISM: Human immunodeficiency virus type 1

<400> SEQUENCE: 9

tggaagggct aatttggtcc caaaaaagac aagagatcct tgatctgtgg atctaccaca     60

cacaaggcta cttccctgat tggcagaact acacaccagg gccagggatc agatatccac    120

tgacctttgg atggtgcttc aagttagtac cagttgaacc agagcaagta gaagaggcca    180
```

```
aataaggaga gaagaacagc ttgttacacc ctatgagcca gcatgggatg gaggacccgg    240
agggagaagt attagtgtgg aagtttgaca gcctcctagc atttcgtcac atggcccgag    300
agctgcatcc ggagtactac aaagactgct gacatcgagc tttctacaag ggactttccg    360
ctggggactt tccagggagg tgtggcctgg gcgggactgg ggagtggcga gccctcagat    420
gctacatata agcagctgct ttttgcctgt actgggtctc tctggttaga ccagatctga    480
gcctgggagc tctctggcta actagggaac ccactgctta agcctcaata aagcttgcct    540
tgagtgctca aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagtaaa gccagaggag atctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcggta ttaagcgggg gagaattaga taaatgggaa    840
aaaattcggt taaggccagg gggaaagaaa caatataaac taaaacatat agtatgggca    900
agcagggagc tagaacgatt cgcagttaat cctggccttt tagagacatc agaaggctgt    960
agacaaatac tgggacagct acaaccatcc cttcagacag gatcagaaga acttagatca   1020
ttatataata caatagcagt cctctattgt gtgcatcaaa ggatagatgt aaaagacacc   1080
aaggaagcct tagataagat agaggaagag caaaacaaaa gtaagaaaaa ggcacagcaa   1140
gcagcagctg acacaggaaa caacagccag gtcagccaaa attaccctat agtgcagaac   1200
ctccaggggc aaatggtaca tcaggccata tcacctagaa ctttaaatgc atgggtaaaa   1260
gtagtagaag agaaggcttt cagcccagaa gtaataccca tgttttcagc attatcagaa   1320
ggagccaccc cacaagattt aaataccatg ctaaacacag tggggggaca tcaagcagcc   1380
atgcaaatgt taaaagagac catcaatgag gaagctgcag aatgggatag attgcatcca   1440
gtgcatgcag ggcctattgc accaggccag atgagagaac caaggggaag tgacatagca   1500
ggaactacta gtacccttca ggaacaaata ggatggatga cacataatcc acctatccca   1560
gtaggagaaa tctataaaag atggataatc ctgggattaa ataaaatagt aagaatgtat   1620
agccctacca gcattctgga cataagacaa ggaccaaagg aaccctttag agactatgta   1680
gaccgattct ataaaactct aagagccgag caagcttcac aagaggtaaa aaattggatg   1740
acagaaacct tgttggtcca aaatgcgaac ccagattgta agactatttt aaaagcattg   1800
ggaccaggag cgacactaga agaaatgatg acagcatgtc agggagtggg gggacccggc   1860
cataaagcaa gagttttggc tgaagcaatg agccaagtaa caaatccagc taccataatg   1920
atacagaaag gcaattttag gaaccaaaga aagactgtta agtgtttcaa ttgtggcaaa   1980
gaagggcaca tagccaaaaa ttgcagggcc cctaggaaaa agggctgttg gaaatgtgga   2040
aaggaaggac accaaatgaa agattgtact gagagacagg ctaatttttt agggaagatc   2100
tggccttccc acaagggaag gccagggaat tttcttcaga gcagaccaga gccaacagcc   2160
ccaccagaag acccagctgt ggatctgcta gagagcttca ggtttgggga agagacaaca   2220
actccctctc agaagcagga gccgatagac aaggaactgt atcctttagc ttccctcaga   2280
tcactctttg gcagcgaccc ctcgtcacaa taaagatagg ggggcaatta aaggaagctc   2340
tattagatac aggagcagat gatacagtat tagaagaaat gaatttgcca ggaagatgga   2400
aaccaaaaat gataggggga attggaggtt ttatcaaagt aagacagtat gatcagatac   2460
tcatagaaat ctgcggacat aaagctatag gtacagtatt agtaggacct acacctgtca   2520
```

-continued

```
acataattgg aagaaatctg ttgactcaga ttggctgcac tttaaatttt cccattagtc   2580
ctattgagac tgtaccagta aaattaaagc caggaatgga tggcccaaaa gttaaacaat   2640
ggccattgac agaagaaaaa ataaaagcat tagtagaaat ttgtacagaa atggaaaagg   2700
aaggaaaaat ttcaaaaatt gggcctgaaa atccatacaa tactccagta tttgccataa   2760
agaaaaaaga cagtactaaa tggagaaaat tagtagattt cagagaactt aataagagaa   2820
ctcaagattt ctgggaagtt caattaggaa taccacatcc tgcagggtta aaacagaaaa   2880
aatcagtaac agtactggat gtgggcgatg catatttttc agttccctta gataaagact   2940
tcaggaagta tactgcattt accataccta gtataaacaa tgagacacca gggattagat   3000
atcagtacaa tgtgcttcca cagggatgga aaggatcacc agcaatattc cagtgtagca   3060
tgacaaaaat cttagagcct tttagaaaac aaaatccaga catagtcatc tatcaataca   3120
tggatgattt gtatgtagga tctgacttag aaatagggca gcatagaaca aaaatagagg   3180
aactgagaca acatctgttg aggtggggat ttaccacacc agacaaaaaa catcagaaag   3240
aacctccatt cctttggatg ggttatgaac tccatcctga taaatggaca gtacagccta   3300
tagtgctgcc agaaaaggac agctggactg tcaatgacat acagaaatta gtgggaaaat   3360
tgaattgggc aagtcagatt tatgcaggga ttaaagtaag gcaattatgt aaacttctta   3420
ggggaaccaa agcactaaca gaagtagtac cactaacaga agaagcagag ctagaactgg   3480
cagaaaacag ggagattcta aaagaaccgg tacatggagt gtattatgac ccatcaaaag   3540
acttaatagc agaaatacag aagcaggggc aaggccaatg gacatatcaa atttatcaag   3600
agccatttaa aaatctgaaa acaggaaaat atgcaagaat gaagggtgcc cacactaatg   3660
atgtgaaaca attaacagag gcagtacaaa aaatagccac agaaagcata gtaatatggg   3720
gaaagactcc taaatttaaa ttacccatac aaaaggaaac atgggaagca tggtggacag   3780
agtattggca agccacctgg attcctgagt gggagtttgt caatacccct cccttagtga   3840
agttatggta ccagttagag aaagaaccca taataggagc agaaactttc tatgtagatg   3900
gggcagccaa tagggaaact aaattaggaa aagcaggata tgtaactgac agaggaagac   3960
aaaaagttgt ccccctaacg gacacaacaa atcagaagac tgagttacaa gcaattcatc   4020
tagctttgca ggattcggga ttagaagtaa acatagtgac agactcacaa tatgcattgg   4080
gaatcattca agcacaacca gataagagtg aatcagagtt agtcagtcaa ataatagagc   4140
agttaataaa aaaggaaaaa gtctacctgg catgggtacc agcacacaaa ggaattggag   4200
gaaatgaaca agtagatggg ttggtcagtg ctggaatcag gaaagtacta tttttagatg   4260
gaatagataa ggcccaagaa gaacatgaga aatatcacag taattggaga gcaatggcta   4320
gtgattttaa cctaccacct gtagtagcaa aagaaatagt agccagctgt gataaatgtc   4380
agctaaaagg ggaagccatg catggacaag tagactgtag cccaggaata tggcagctag   4440
attgtacaca tttagaagga aaagttatct tggtagcagt tcatgtagcc agtggatata   4500
tagaagcaga agtaattcca gcagagacag ggcaagaaac agcatacttc ctcttaaaat   4560
tagcaggaag atggccagta aaaacagtac atacagacaa tggcagcaat ttcaccagta   4620
ctacagttaa ggccgcctgt tggtgggcgg ggatcaagca ggaatttggc attccctaca   4680
atccccaaag tcaaggagta atagaatcta tgaataaaga attaaagaaa attataggac   4740
aggtaagaga tcaggctgaa catcttaaga cagcagtaca aatggcagta ttcatccaca   4800
attttaaaag aaaagggggg attggggggt acagtgcagg ggaaagaata gtagacataa   4860
tagcaacaga catacaaact aaagaattac aaaaacaaat tacaaaaatt caaaattttc   4920
```

```
gggtttatta cagggacagc agagatccag tttggaaagg accagcaaag ctcctctgga   4980
aaggtgaagg ggcagtagta atacaagata atagtgacat aaaagtagtg ccaagaagaa   5040
aagcaaagat catcagggat tatggaaaac agatggcagg tgatgattgt gtggcaagta   5100
gacaggatga ggattaacac atggaaaaga ttagtaaaac accatatgta tatttcaagg   5160
aaagctaagg actggtttta tagacatcac tatgaaagta ctaatccaaa aataagttca   5220
gaagtacaca tcccactagg ggatgctaaa ttagtaataa caacatattg gggtctgcat   5280
acaggagaaa gagactggca tttgggtcag ggagtctcca tagaatggag gaaaaagaga   5340
tatagcacac aagtagaccc tgacctagca gaccaactaa ttcatctgca ctattttgat   5400
tgtttttcag aatctgctat aagaaatacc atattaggac gtatagttag tcctaggtgt   5460
gaatatcaag caggacataa caaggtagga tctctacagt acttggcact agcagcatta   5520
ataaaaccaa aacagataaa gccacctttg cctagtgtta ggaaactgac agaggacaga   5580
tggaacaagc cccagaagac caagggccac agagggagcc atacaatgaa tggacactag   5640
agcttttaga ggaacttaag agtgaagctg ttagacattt tcctaggata tggctccata   5700
acttaggaca acatatctat gaaacttacg gggatacttg ggcaggagtg gaagccataa   5760
taagaattct gcaacaactg ctgtttatcc atttcagaat tgggtgtcga catagcagaa   5820
taggcgttac tcgacagagg agagcaagaa atggagccag tagatcctag actagagccc   5880
tggaagcatc caggaagtca gcctaaaact gcttgtacca attgctattg taaaaagtgt   5940
tgctttcatt gccaagtttg tttcatgaca aaagccttag gcatctccta tggcaggaag   6000
aagcggagac agcgacgaag agctcatcag aacagtcaga ctcatcaagc ttctctatca   6060
aagcagtaag tagtacatgt aatgcaacct ataatagtag caatagtagc attagtagta   6120
gcaataataa tagcaatagt tgtgtggtcc atagtaatca tagaatatag gaaaatatta   6180
agacaaagaa aaatagacag gttaattgat agactaatag aaagagcaga agacagtggc   6240
aatgagagtg aaggagaagt atcagcactt gtggagatgg gggtggaaat ggggcaccat   6300
gctccttggg atattgatga tctgtagtgc tacagaaaaa ttgtgggtca ccgtctatta   6360
tggggtacct gtgtggaaag aagcaaccac cactctattt tgtgcatcag atgctaaagc   6420
atatgataca gaggtacata atgtttgggc cacacatgcc tgtgtaccca cagaccccaa   6480
cccacaagaa gtagtattgg aaaatgtaac agaacatttt aacatgtgga aaaataacat   6540
ggtagaacag atgcaggagg atataatcag tttatgggat caaagcctaa agccatgtgt   6600
aaaattaacc ccactctgtg ttactttaaa ttgcaaggat gtgaatgcta ctaataccac   6660
taatgatagc gagggaacga tggagagagg agaaataaaa aactgctctt tcaatatcac   6720
cacaagcata agagatgagg tgcagaaaga atatgctctt ttttataaac ttgatgtagt   6780
accaatagat aataataata ccagctatag gttgataagt tgtgacacct cagtcattac   6840
acaggcctgt ccaaagatat cctttgagcc aattcccata cattattgtg ccccggctgg   6900
ttttgcgatt ctaaagtgta atgataagac gttcaatgga aaaggaccat gtaaaaatgt   6960
cagcacagta caatgtacac atggaattag gccagtagta tcaactcaac tgctgctaaa   7020
tggcagtcta gcagaagaag aggtagtaat tagatctgac aatttcacga acaatgctaa   7080
aaccataata gtacagctga aagaatctgt agaaattaat tgtacaagac ccaacaacaa   7140
tacaagaaaa agtatacata taggaccagg gagagcattt tatactacag gagaaataat   7200
aggagatata agacaagcac attgtaacat tagtagagca aaatggaatg acactttaaa   7260
```

-continued

```
acagatagtt ataaaattaa gagaacaatt tgagaataaa acaatagtct ttaatcactc   7320
ctcaggaggg gacccagaaa ttgtaatgca cagttttaat tgtggaggag aatttttcta   7380
ctgtaattca acacaactgt ttaatagtac ttggaataat aatactgaag ggtcaaataa   7440
cactgaagga aatactatca cactcccatg cagaataaaa caaattataa acatgtggca   7500
ggaagtagga aaagcaatgt atgcccctcc catcagagga caaattagat gttcatcaaa   7560
tattacaggg ctgctattaa caagagatgg tggtattaat gagaatggga ccgagatctt   7620
cagacctgga ggaggagata tgagggacaa ttggagaagt gaattatata aatataaagt   7680
agtaaaaatt gaaccattag gagtagcacc caccaaggca aagagaagag tggtgcaaag   7740
agaaaaaaga gcagtgggaa taggagctgt gttccttggg ttcttgggag cagcaggaag   7800
cactatgggc gcagcgtcaa tgacactgac ggtacaggcc agactattat tgtctggtat   7860
agtgcaacag cagaacaatt tgctgagggc tattgaggcg caacagcgta tgttgcaact   7920
cacagtctgg ggcatcaagc agctccaggc aagagtcctg gctgtggaaa gatacctagg   7980
ggatcaacag ctcctgggga tttggggttg ctctggaaaa ctcatttgca ccactgctgt   8040
gccttggaat gctagttgga gtaataaatc tctggatagg atttggaata acatgacctg   8100
gatggagtgg gaaagagaaa ttgacaatta cacaagcgaa atatacaccc taattgaaga   8160
atcgcagaac caacaagaaa agaatgaaca agaattattg gaattagata aatgggcaag   8220
tttgtggaat tggtttgaca taacaaaatg gctgtggtat ataaaaatat tcataatgat   8280
agtaggaggc ttagtaggtt taagactagt ttttactgta ctttctatag tgaatagagt   8340
taggcaggga tactcaccat tatcgtttca gaccctcctc ccagccccga ggggacccga   8400
caggcccgaa ggaatcgaag aagaaggtgg agagagagac agagacagat ccggacgatt   8460
agtgaacgga ttcttagcac ttatctgggt cgacctgcgg agcctgtgcc tcttcagcta   8520
ccaccgcttg agagacttac tcttgactgt aacgaggatt gtggaacttc tgggacgcag   8580
ggggtgggaa gtcctgaaat attggtggaa tctcctacag tattggagtc aggaactaaa   8640
gaatagtgct gttagcttgc tcaatgccac agccatagca gtagctgagg ggacagatag   8700
gattatagaa gcattacaaa gaacttatag agctattctc cacataccta caagaataag   8760
acagggcttg gaaagggctt tgctataagc ggccgcaatg agcgacccaa gagagagaat   8820
cccaccaggc aatagcggcg aagaaacaat cggagaggct tttgaatggc tgaacaggac   8880
cgtcgaggaa atcaaccggg aggcagtgaa tcacctgcct agagaactga ttttccaggt   8940
ctggcagcga tcttgggagt actggcatga cgaacagggg atgagccagt cctatgtgaa   9000
gtacagatat ctgtgcctga tgcagaaagc cctgtttatg cactgtaaga aaggctgcag   9060
gtgtctggga gagggccatg ggccggcggg gtggcgcccc ggacccccctc cacccccctcc   9120
acccggcctg gcttgacccg ggtaccttta agaccaatga cttacaaggc agctgtagat   9180
cttagccact ttttaaaaga aaagggggga ctggaagggc taattcactc ccaaagaaga   9240
caagatatcc ttgatctgtg gatctaccac acacaaggct acttccctga ttggcagaac   9300
tacacaccag ggccaggggt cagatatcca ctgacctttg gatggtgcta caagctagta   9360
ccagttgagc cagataaggt agaagaggcc aataaaggag agaacaccag cttgttacac   9420
cctgtgagcc tgcatggaat ggatgaccct gagagagaag tgttacgcct agcatttcat   9480
cacgtggccc gagagctgca tccggagtac ttcaagaact gctgacatcg agcttgctac   9540
aagggacttt ccgctgggga ctttccaggg aggcgtggcc tgggcgggac tggggagtgg   9600
cgagccctca gatgctgcat ataagcagct gctttttgcc tgtactgggt ctctctggtt   9660
```

```
agaccagatc tgagcctggg agctctctgg ctaactaggg aacccactgc ttaagcctca   9720
ataaagcttg ccttgagtgc ttcaagtagt gtgtgcccgt ctgttgtgtg actctggtaa   9780
ctagagatcc ctcagaccct tttagtcagt gtggaaaatc tctagcaccc cccaggaggt   9840
agaggttgca gtgagccaag atcgcgccac tgcattccag cctgggcaag aaaacaagac   9900
tgtctaaaat aataataata agttaagggt attaaatata tttatacatg gaggtcataa   9960
aaatatatat atttgggctg ggcgcagtgg ctcacacctg cgcccggccc tttgggaggc  10020
cgaggcaggt ggatcacctg agtttgggag ttccagacca gcctgaccaa catggagaaa  10080
ccccttctct gtgtattttt agtagatttt attttatgtg tattttattc acaggtattt  10140
ctggaaaact gaaactgttt ttcctctact ctgataccac aagaatcatc agcacagagg  10200
aagacttctg tgatcaaatg tggtgggaga gggaggtttt caccagcaca tgagcagtca  10260
gttctgccgc agactcggcg ggtgtccttc ggttcagttc caacaccgcc tgcctggaga  10320
gaggtcagac cacagggtga gggctcagtc cccaagacat aaacacccaa gacataaaca  10380
cccaacaggt ccaccccgcc tgctgcccag gcagagccga ttcaccaaga cgggaattag  10440
gatagagaaa gagtaagtca cacagagccg gctgtgcggg agaacggagt tctattatga  10500
ctcaaatcag tctccccaag cattcgggga tcagagtttt taaggataac ttagtgtgta  10560
gggggccagt gagttggaga tgaaagcgta gggagtcgaa ggtgtccttt tgcgccgagt  10620
cagttcctgg gtgggggcca caagatcgga tgagccagtt tatcaatccg gggtgccag   10680
ctgatccatg gagtgcaggg tctgcaaaat atctcaagca ctgattgatc ttaggtttta  10740
caatagtgat gttaccccag gaacaatttg gggaaggtca gaatcttgta gcctgtagct  10800
gcatgactcc taaaccataa tttctttttt gttttttttt ttttattttt gagacagggt  10860
ctcactctgt cacctaggct ggagtgcagt ggtgcaatca cagctcactg cagcctcaac  10920
gtcgtaagct caagcgatcc tcccacctca gcctgcctgg tagctgagac tacaagcgac  10980
gccccagtta atttttgtat ttttggtaga ggcagcgttt tgccgtgtgg ccctggctgg  11040
tctcgaactc ctgggctcaa gtgatccagc ctcagcctcc caaagtgctg ggacaaccgg  11100
ggccagtcac tgcacctggc cctaaaccat aatttctaat cttttggcta atttgttagt  11160
cctacaaagg cagtctagtc cccaggcaaa aagggggttt gtttcgggaa agggctgtta  11220
ctgtctttgt ttcaaactat aaactaagtt cctcctaaac ttagttcggc ctacacccag  11280
gaatgaacaa ggagagcttg gaggttagaa gcacgatgga attggttagg tcagatctct  11340
ttcactgtct gagttataat tttgcaatgg tggttcaaag actgcccgct tctgacacca  11400
gtcgctgcat taatgaatcg gccaacgcgc ggggagaggc ggtttgcgta ttggcgctct  11460
tccgcttcct cgctcactga ctcgctgcgc tcggtcgttc ggctgcggcg agcggtatca  11520
gctcactcaa aggcggtaat acggttatcc acagaatcag gggataacgc aggaaagaac  11580
atgtgagcaa aaggccagca aaaggccagg aaccgtaaaa aggccgcgtt gctggcgttt  11640
ttccataggc tccgcccccc tgacgagcat cacaaaaatc gacgctcaag tcagaggtgg  11700
cgaaacccga caggactata aagataccag gcgtttcccc ctggaagctc cctcgtgcgc  11760
tctcctgttc cgaccctgcc gcttaccgga tacctgtccg cctttctccc ttcgggaagc  11820
gtggcgcttt ctcaatgctc acgctgtagg tatctcagtt cggtgtaggt cgttcgctcc  11880
aagctgggct gtgtgcacga accccccgtt cagcccgacc gctgcgcctt atccggtaac  11940
tatcgtcttg agtccaaccc ggtaagacac gacttatcgc cactggcagc agccactggt  12000
```

-continued

```
aacaggatta gcagagcgag gtatgtaggc ggtgctacag agttcttgaa gtggtggcct  12060
aactacggct acactagaag gacagtattt ggtatctgcg ctctgctgaa gccagttacc  12120
ttcggaaaaa gagttggtag ctcttgatcc ggcaaacaaa ccaccgctgg tagcggtggt  12180
tttttgttt gcaagcagca gattacgcgc agaaaaaaag gatctcaaga agatcctttg  12240
atcttttcta cggggtctga cgctcagtgg aacgaaaact cacgttaagg gattttggtc  12300
atgagattat caaaaaggat cttcacctag atccttttaa attaaaaatg aagttttaaa  12360
tcaatctaaa gtatatatga gtaaacttgg tctgacagtt accaatgctt aatcagtgag  12420
gcacctatct cagcgatctg tctatttcgt tcatccatag ttgcctgact ccccgtcgtg  12480
tagataacta cgatacggga gggcttacca tctggcccca gtgctgcaat gataccgcga  12540
gacccacgct caccggctcc agatttatca gcaataaacc agccagccgg aagggccgag  12600
cgcagaagtg gtcctgcaac tttatccgcc tccatccagt ctattaattg ttgccgggaa  12660
gctagagtaa gtagttcgcc agttaatagt ttgcgcaacg ttgttgccat tgctacaggc  12720
atcgtggtgt cacgctcgtc gtttggtatg gcttcattca gctccggttc ccaacgatca  12780
aggcgagtta catgatcccc catgttgtgc aaaaaagcgg ttagctcctt cggtcctccg  12840
atcgttgtca gaagtaagtt ggccgcagtg ttatcactca tggttatggc agcactgcat  12900
aattctctta ctgtcatgcc atccgtaaga tgcttttctg tgactggtga gtactcaacc  12960
aagtcattct gagaatagtg tatgcggcga ccgagttgct cttgcccggc gtcaatacgg  13020
gataataccg cgccacatag cagaacttta aaagtgctca tcattggaaa acgttcttcg  13080
gggcgaaaac tctcaaggat cttaccgctg ttgagatcca gttcgatgta acccactcgt  13140
gcacccaact gatcttcagc atcttttact ttcaccagcg tttctgggtg agcaaaaaca  13200
ggaaggcaaa atgccgcaaa aaagggaata agggcgacac ggaaatgttg aatactcata  13260
ctcttccttt ttcaatatta ttgaagcatt tatcagggtt attgtctcat gagcggatac  13320
atatttgaat gtatttagaa aaataaacaa ataggggttc cgcgcacatt tccccgaaaa  13380
gtgccacctg acgtctaaga aaccattatt atcatgacat taacctataa aaataggcgt  13440
atcacgaggc cctttcgtct tcaagaactg cctcgcgcgt ttcggtgatg acggtgaaaa  13500
cctctgacac atgcagctcc cggagacggt cacagcttgt ctgtaagcgg atgccgggag  13560
cagacaagcc cgtcagggcg cgtcagcggg tgttggcggg tgtcggggcg cagccatgac  13620
ccagtcacgt agcgatagcg gagtgtactg gcttaactat gcggcatcag agcagattgt  13680
actgagagtg caccatatgc ggtgtgaaat accgcacaga tgcgtaagga gaaaataccg  13740
catcaggcgc cattcgccat tcaggctgcg caactgttgg gaagggcgat cggtgcgggc  13800
ctcttcgcta ttacgccagg ggaggcagag attgcagtaa gctgagatcg cagcactgca  13860
ctccagcctg ggcgacagag taagactctg tctcaaaaat aaaataaata aatcaatcag  13920
atattccaat cttttccttt atttatttat ttattttcta ttttggaaac acagtccttc  13980
cttattccag aattacacat atattctatt tttctttata tgctccagtt ttttttagac  14040
cttcacctga aatgtgtgta tacaaaatct aggccagtcc agcagagcct aaaggtaaaa  14100
aataaaataa taaaaaataa ataaaatcta gctcactcct tcacatcaaa atggagatac  14160
agctgttagc attaaatacc aaataaccca tcttgtcctc aataatttta agcgcctctc  14220
tccaccacat ctaactcctg tcaaaggcat gtgccccttc cgggcgctct gctgtgctgc  14280
caaccaactg gcatgtggac tctgcagggt ccctaactgc caagccccac agtgtgccct  14340
gaggctgccc cttccttcta gcggctgccc ccactcggct ttgctttccc tagtttcagt  14400
```

```
tacttgcgtt cagccaaggt ctgaaactag gtgcgcacag agcggtaaga ctgcgagaga  14460
aagagaccag ctttacaggg ggtttatcac agtgcaccct gacagtcgtc agcctcacag  14520
ggggtttatc acattgcacc ctgacagtcg tcagcctcac agggggttta tcacagtgca  14580
cccttacaat cattccattt gattcacaat ttttttagtc tctactgtgc ctaacttgta  14640
agttaaattt gatcagaggt gtgttcccag aggggaaaac agtatataca gggttcagta  14700
ctatcgcatt tcaggcctcc acctgggtct tggaatgtgt cccccgaggg gtgatgacta  14760
cctcagttgg atctccacag gtcacagtga cacaagataa ccaagacacc tcccaaggct  14820
accacaatgg gccgccctcc acgtgcacat ggccggagga actgccatgt cggaggtgca  14880
agcacacctg cgcatcagag tccttggtgt ggagggaggg accagcgcag cttccagcca  14940
tccacctgat gaacagaacc tagggaaagc cccagttcta cttacaccag gaaaggc     14997
```

```
<210> SEQ ID NO 10
<211> LENGTH: 15357
<212> TYPE: DNA
<213> ORGANISM: Human immunodeficiency virus type 1

<400> SEQUENCE: 10
```

```
tggaagggct aatttggtcc caaaaaagac aagagatcct tgatctgtgg atctaccaca     60
cacaaggcta cttccctgat tggcagaact acacaccagg gccagggatc agatatccac    120
tgacctttgg atggtgcttc aagttagtac cagttgaacc agagcaagta gaagaggcca    180
aataaggaga gaagaacagc ttgttacacc ctatgagcca gcatgggatg gaggacccgg    240
agggagaagt attagtgtgg aagtttgaca gcctcctagc atttcgtcac atggcccgag    300
agctgcatcc ggagtactac aaagactgct gacatcgagc tttctacaag ggactttccg    360
ctggggactt tccagggagg tgtggcctgg gcgggactgg ggagtggcga gccctcagat    420
gctacatata agcagctgct ttttgcctgt actgggtctc tctggttaga ccagatctga    480
gcctgggagc tctctggcta actagggaac ccactgctta agcctcaata aagcttgcct    540
tgagtgctca aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagtaaa gccagaggag atctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcggta ttaagcgggg gagaattaga taaatgggaa    840
aaaattcggt taaggccagg gggaaagaaa caatataaac taaaacatat agtatgggca    900
agcagggagc tagaacgatt cgcagttaat cctggccttt tagagacatc agaaggctgt    960
agacaaatac tgggacagct acaaccatcc cttcagacag gatcagaaga acttagatca   1020
ttatataata caatagcagt cctctattgt gtgcatcaaa ggatagatgt aaaagacacc   1080
aaggaagcct tagataagat agaggaagag caaaacaaaa gtaagaaaaa ggcacagcaa   1140
gcagcagctg acacaggaaa caacagccag gtcagccaaa attaccctat agtgcagaac   1200
ctccaggggc aaatggtaca tcaggccata tcacctagaa ctttaaatgc atgggtaaaa   1260
gtagtagaag agaaggcttt cagcccagaa gtaataccca tgttttcagc attatcagaa   1320
ggagccaccc cacaagattt aaataccatg ctaaacacag tggggggaca tcaagcagcc   1380
atgcaaatgt taaaagagac catcaatgag gaagctgcag aatgggatag attgcatcca   1440
gtgcatgcag ggcctattgc accaggccag atgagagaac caaggggaag tgacatagca   1500
```

```
ggaactacta gtacccttca ggaacaaata ggatggatga cacataatcc acctatccca   1560
gtaggagaaa tctataaaag atggataatc ctgggattaa ataaaatagt aagaatgtat   1620
agccctacca gcattctgga cataagacaa ggaccaaagg aaccctttag agactatgta   1680
gaccgattct ataaaactct aagagccgag caagcttcac aagaggtaaa aaattggatg   1740
acagaaacct tgttggtcca aaatgcgaac ccagattgta agactatttt aaaagcattg   1800
ggaccaggag cgacactaga agaaatgatg acagcatgtc agggagtggg gggacccggc   1860
cataaagcaa gagttttggc tgaagcaatg agccaagtaa caaatccagc taccataatg   1920
atacagaaag gcaattttag gaaccaaaga aagactgtta agtgtttcaa ttgtggcaaa   1980
gaagggcaca tagccaaaaa ttgcagggcc cctaggaaaa agggctgttg gaaatgtgga   2040
aaggaaggac accaaatgaa agattgtact gagagacagg ctaatttttt agggaagatc   2100
tggccttccc acaagggaag gccagggaat ttcttcaga gcagaccaga gccaacagcc   2160
ccaccagaag agagcttcag gtttggggaa gagacaacaa ctccctctca gaagcaggag   2220
ccgatagaca aggaactgta tcctttagct tccctcagat cactctttgg cagcgacccc   2280
tcgtcacaat aaagataggg gggcaattaa aggaagctct attagataca ggagcagatg   2340
atacagtatt agaagaaatg aatttgccag gaagatggaa accaaaaatg atagggggaa   2400
ttggaggttt tatcaaagta ggacagtatg atcagatact catagaaatc tgcggacata   2460
aagctatagg tacagtatta gtaggaccta cacctgtcaa cataattgga agaaatctgt   2520
tgactcagat tggctgcact ttaaattttc ccattagtcc tattgagact gtaccagtaa   2580
aattaaagcc aggaatggat ggcccaaaag ttaaacaatg gccattgaca gaagaaaaaa   2640
taaaagcatt agtagaaatt tgtacagaaa tggaaaagga aggaaaaatt tcaaaaattg   2700
ggcctgaaaa tccatacaat actccagtat ttgccataaa gaaaaaagac agtactaaat   2760
ggagaaaatt agtagatttc agagaactta ataagagaac tcaagatttc tgggaagttc   2820
aattaggaat accacatcct gcagggttaa aacagaaaaa atcagtaaca gtactggatg   2880
tgggcgatgc atatttttca gttcccttag ataaagactt caggaagtat actgcattta   2940
ccatacctag tataaacaat gagacaccag ggattagata tcagtacaat gtgcttccac   3000
agggatggaa aggatcacca gcaatattcc agtgtagcat gacaaaaatc ttagagcctt   3060
ttagaaaaca aaatccagac atagtcatct atcaatacat ggatgatttg tatgtaggat   3120
ctgacttaga aatagggcag catagaacaa aaatagagga actgagacaa catctgttga   3180
ggtggggatt taccacacca gacaaaaaac atcagaaaga acctccattc ctttggatgg   3240
gttatgaact ccatcctgat aaatggacag tacagcctat agtgctgcca gaaaaggaca   3300
gctggactgt caatgacata cagaaattag tgggaaaatt gaattgggca agtcagattt   3360
atgcagggat taaagtaagg caattatgta aacttcttag gggaaccaaa gcactaacag   3420
aagtagtacc actaacagaa gaagcagagc tagaactggc agaaaacagg gagattctaa   3480
aagaaccggt acatggagtg tattatgacc catcaaaaga cttaatagca gaaatacaga   3540
agcaggggca aggccaatgg acatatcaaa tttatcaaga gccatttaaa aatctgaaaa   3600
caggaaaata tgcaagaatg aagggtgccc acactaatga tgtgaaacaa ttaacagagg   3660
cagtacaaaa aatagccaca gaaagcatag taatatgggg aaagactcct aaatttaaat   3720
tacccataca aaaggaaaca tgggaagcat ggtggacaga gtattggcaa gccacctgga   3780
ttcctgagtg ggagtttgtc aataccctc ccttagtgaa gttatggtac cagttagaga   3840
aagaacccat aataggagca gaaactttct atgtagatgg ggcagccaat agggaaacta   3900
```

```
aattaggaaa agcaggatat gtaactgaca gaggaagaca aaaagttgtc cccctaacgg   3960

acacaacaaa tcagaagact gagttacaag caattcatct agctttgcag gattcgggat   4020

tagaagtaaa catagtgaca gactcacaat atgcattggg aatcattcaa gcacaaccag   4080

ataagagtga atcagagtta gtcagtcaaa taatagagca gttaataaaa aaggaaaaag   4140

tctacctggc atgggtacca gcacacaaag gaattggagg aaatgaacaa gtagatgggt   4200

tggtcagtgc tggaatcagg aaagtactat ttttagatgg aatagataag gcccaagaag   4260

aacatgagaa atatcacagt aattggagag caatggctag tgattttaac ctaccacctg   4320

tagtagcaaa agaaatagta gccagctgtg ataaatgtca gctaaaaggg gaagccatgc   4380

atggacaagt agactgtagc ccaggaatat ggcagctaga ttgtacacat ttagaaggaa   4440

aagttatctt ggtagcagtt catgtagcca gtggatatat agaagcagaa gtaattccag   4500

cagagacagg gcaagaaaca gcatacttcc tcttaaaatt agcaggaaga tggccagtaa   4560

aaacagtaca tacagacaat ggcagcaatt tcaccagtac tacagttaag gccgcctgtt   4620

ggtgggcggg gatcaagcag gaatttggca ttccctacaa tccccaaagt caaggagtaa   4680

tagaatctat gaataaagaa ttaaagaaaa ttataggaca ggtaagagat caggctgaac   4740

atcttaagac agcagtacaa atggcagtat tcatccacaa ttttaaaaga aaagggggga   4800

ttggggggta cagtgcaggg gaaagaatag tagacataat agcaacagac atacaaacta   4860

aagaattaca aaaacaaatt acaaaaattc aaaattttcg ggtttattac agggacagca   4920

gagatccagt ttggaaagga ccagcaaagc tcctctggaa aggtgaaggg gcagtagtaa   4980

tacaagataa tagtgacata aaagtagtgc caagaagaaa agcaaagatc atcagggatt   5040

atggaaaaca gatggcaggt gatgattgtg tggcaagtag acaggatgag gattaacaca   5100

tggaaaagat tagtaaaaca ccatatgtat atttcaagga aagctaagga ctggttttat   5160

agacatcact atgaaagtac taatccaaaa ataagttcag aagtacacat cccactaggg   5220

gatgctaaat tagtaataac aacatattgg ggtctgcata caggagaaag agactggcat   5280

ttgggtcagg gagtctccat agaatggagg aaaaagagat atagcacaca agtagaccct   5340

gacctagcag accaactaat tcatctgcac tattttgatt gtttttcaga atctgctata   5400

agaaatacca tattaggacg tatagttagt cctaggtgtg aatatcaagc aggacataac   5460

aaggtaggat ctctacagta cttggcacta gcagcattaa taaaaccaaa acagataaag   5520

ccacctttgc ctagtgttag gaaactgaca gaggacagat ggaacaagcc ccagaagacc   5580

aagggccaca gagggagcca tacaatgaat ggacactaga gcttttagag gaacttaaga   5640

gtgaagctgt tagacatttt cctaggatat ggctccataa cttaggacaa catatctatg   5700

aaacttacgg ggatacttgg gcaggagtgg aagccataat aagaattctg caacaactgc   5760

tgtttatcca tttcagaatt gggtgtcgac atagcagaat aggcgttact cgacagagga   5820

gagcaagaaa tggagccagt agatcctaga ctagagccct ggaagcatcc aggaagtcag   5880

cctaaaactg cttgtaccaa ttgctattgt aaaaagtgtt gctttcattg ccaagtttgt   5940

ttcatgacaa aagccttagg catctcctat ggcaggaaga agcggagaca gcgacgaaga   6000

gctcatcaga acagtcagac tcatcaagct tctctatcaa agcagtaagt agtacatgta   6060

atgcaaccta taatagtagc aatagtagca ttagtagtag caataataat agcaatagtt   6120

gtgtggtcca tagtaatcat agaatatagg aaaatattaa gacaaagaaa aatagacagg   6180

ttaattgata gactaataga aagagcagaa gacagtggca atgagagtga aggagaagta   6240
```

-continued

```
tcagcacttg tggagatggg ggtggaaatg gggcaccatg ctccttggga tattgatgat   6300
ctgtagtgct acagaaaaat tgtgggtcac cgtctattat ggggtacctg tgtggaaaga   6360
agcaaccacc actctatttt gtgcatcaga tgctaaagca tatgatacag aggtacataa   6420
tgtttgggcc acacatgcct gtgtacccac agaccccaac ccacaagaag tagtattgga   6480
aaatgtaaca gaacatttta acatgtggaa aaataacatg gtagaacaga tgcaggagga   6540
tataatcagt ttatgggatc aaagcctaaa gccatgtgta aaattaaccc cactctgtgt   6600
tactttaaat tgcaaggatg tgaatgctac taataccact aatgatagcg agggaacgat   6660
ggagagagga gaaataaaaa actgctcttt caatatcacc acaagcataa gagatgaggt   6720
gcagaaagaa tatgctcttt tttataaact tgatgtagta ccaatagata ataataatac   6780
cagctatagg ttgataagtt gtgacacctc agtcattaca caggcctgtc caaagatatc   6840
ctttgagcca attcccatac attattgtgc cccggctggt tttgcgattc taaagtgtaa   6900
tgataagacg ttcaatggaa aaggaccatg taaaaatgtc agcacagtac aatgtacaca   6960
tggaattagg ccagtagtat caactcaact gctgctaaat ggcagtctag cagaagaaga   7020
ggtagtaatt agatctgaca atttcacgaa caatgctaaa accataatag tacagctgaa   7080
agaatctgta gaaattaatt gtacaagacc caacaacaat acaagaaaaa gtatacatat   7140
aggaccaggg agagcatttt atactacagg agaaataata ggagatataa gacaagcaca   7200
ttgtaacatt agtagagcaa aatggaatga cactttaaaa cagatagtta taaaattaag   7260
agaacaattt gagaataaaa caatagtctt taatcactcc tcaggagggg acccagaaat   7320
tgtaatgcac agttttaatt gtggaggaga atttttctac tgtaattcaa cacaactgtt   7380
taatagtact tggaataata atactgaagg gtcaaataac actgaaggaa atactatcac   7440
actcccatgc agaataaaac aaattataaa catgtggcag gaagtaggaa aagcaatgta   7500
tgcccctccc atcagaggac aaattagatg ttcatcaaat attacagggc tgctattaac   7560
aagagatggt ggtattaatg agaatgggac cgagatcttc agacctggag gaggagatat   7620
gagggacaat tggagaagtg aattatataa atataaagta gtaaaaattg aaccattagg   7680
agtagcaccc accaaggcaa agagaagagt ggtgcaaaga gaaaaaagag cagtgggaat   7740
aggagctgtg ttccttgggt tcttgggagc agcaggaagc actatgggcg cagcgtcaat   7800
gacactgacg gtacaggcca gactattatt gtctggtata gtgcaacagc agaacaattt   7860
gctgagggct attgaggcgc aacagcgtat gttgcaactc acagtctggg gcatcaagca   7920
gctccaggca agagtcctgg ctgtggaaag atacctaggg gatcaacagc tcctggggat   7980
ttggggttgc tctggaaaac tcatttgcac cactgctgtg ccttggaatg ctagttggag   8040
taataaatct ctggatagga tttggaataa catgacctgg atggagtggg aaagagaaat   8100
tgacaattac acaagcgaaa tatacaccct aattgaagaa tcgcagaacc aacaagaaaa   8160
gaatgaacaa gaattattgg aattagataa atgggcaagt ttgtggaatt ggtttgacat   8220
aacaaaatgg ctgtggtata taaaaatatt cataatgata gtaggaggct tagtaggttt   8280
aagactagtt tttactgtac tttctatagt gaatagagtt aggcagggat actcaccatt   8340
atcgtttcag accctcctcc cagccccgag gggacccgac aggcccgaag gaatcgaaga   8400
agaaggtgga gagagagaca gagacagatc cggacgatta gtgaacggat tcttagcact   8460
tatctgggtc gacctgcgga gcctgtgcct cttcagctac caccgcttga gagacttact   8520
cttgactgta acgaggattg tggaacttct gggacgcagg gggtgggaag tcctgaaata   8580
ttggtggaat ctcctacagt attggagtca ggaactaaag aatagtgctg ttagcttgct   8640
```

caatgccaca gccatagcag tagctgaggg gacagatagg attatagaag cattacaaag 8700
aacttataga gctattctcc acatacctac aagaataaga cagggcttgg aaagggcttt 8760
gctataagcg gccgccatgg tgagcaaggg cgaggagctg ttcaccgggg tggtgcccat 8820
cctggtcgag ctggacggcg acgtaaacgg ccacaagttc agcgtgtccg gcgagggcga 8880
gggcgatgcc acctacggca agctgaccct gaagttcatc tgcaccaccg gcaagctgcc 8940
cgtgccctgg cccaccctcg tgaccaccct gacctacggc gtgcagtgct tcagccgcta 9000
ccccgaccac atgaagcagc acgacttctt caagtccgcc atgcccgaag gctacgtcca 9060
ggagcgcacc atcttcttca aggacgacgg caactacaag acccgcgccg aggtgaagtt 9120
cgagggcgac accctggtga accgcatcga gctgaagggc atcgacttca aggaggacgg 9180
caacatcctg gggcacaagc tggagtacaa ctacaacagc cacaacgtct atatcatggc 9240
cgacaagcag aagaacggca tcaaggtgaa cttcaagatc cgccacaaca tcgaggacgg 9300
cagcgtgcag ctcgccgacc actaccagca gaacaccccc atcggcgacg gccccgtgct 9360
gctgcccgac aaccactacc tgagcaccca gtccgccctg agcaaagacc ccaacgagaa 9420
gcgcgatcac atggtcctgc tggagttcgt gaccgccgcc gggatcactc tcggcatgga 9480
cgagctgtac aagtaacccg ggtacccttta agaccaatga cttacaaggc agctgtagat 9540
cttagccact ttttaaaaga aaaggggga ctggaagggc taattcactc ccaaagaaga 9600
caagatatcc ttgatctgtg gatctaccac acacaaggct acttccctga ttggcagaac 9660
tacacaccag ggccaggggt cagatatcca ctgacctttg gatggtgcta caagctagta 9720
ccagttgagc cagataaggt agaagaggcc aataaaggag agaacaccag cttgttacac 9780
cctgtgagcc tgcatggaat ggatgaccct gagagagaag tgttacgcct agcatttcat 9840
cacgtggccc gagagctgca tccggagtac ttcaagaact gctgacatcg agcttgctac 9900
aagggacttt ccgctgggga ctttccaggg aggcgtggcc tgggcgggac tggggagtgg 9960
cgagccctca gatgctgcat ataagcagct gctttttgcc tgtactgggt ctctctggtt 10020
agaccagatc tgagcctggg agctctctgg ctaactaggg aacccactgc ttaagcctca 10080
ataaagcttg ccttgagtgc ttcaagtagt gtgtgcccgt ctgttgtgtg actctggtaa 10140
ctagagatcc ctcagaccct tttagtcagt gtggaaaatc tctagcaccc cccaggaggt 10200
agaggttgca gtgagccaag atcgcgccac tgcattccag cctgggcaag aaaacaagac 10260
tgtctaaaat aataataata agttaagggt attaaatata tttatacatg gaggtcataa 10320
aaatatatat atttgggctg ggcgcagtgg ctcacacctg cgcccggccc tttgggaggc 10380
cgaggcaggt ggatcacctg agtttgggag ttccagacca gcctgaccaa catggagaaa 10440
ccccttctct gtgtattttt agtagatttt attttatgtg tattttattc acaggtattt 10500
ctggaaaact gaaactgttt ttcctctact ctgataccac aagaatcatc agcacagagg 10560
aagacttctg tgatcaaatg tggtgggaga gggaggtttt caccagcaca tgagcagtca 10620
gttctgccgc agactcggcg ggtgtccttc ggttcagttc caacaccgcc tgcctggaga 10680
gaggtcagac cacagggtga gggctcagtc cccaagacat aaacacccaa gacataaaca 10740
cccaacaggt ccaccccgcc tgctgcccag gcagagccga ttcaccaaga cgggaattag 10800
gatagagaaa gagtaagtca cacagagccg gctgtgcggg agaacggagt tctattatga 10860
ctcaaatcag tctccccaag cattcgggga tcagagtttt taaggataac ttagtgtgta 10920
gggggccagt gagttggaga tgaaagcgta gggagtcgaa ggtgtccttt tgcgccgagt 10980

```
cagttcctgg gtgggggcca caagatcgga tgagccagtt tatcaatccg gggtgccag  11040
ctgatccatg gagtgcaggg tctgcaaaat atctcaagca ctgattgatc ttaggtttta  11100
caatagtgat gttaccccag gaacaatttg gggaaggtca gaatcttgta gcctgtagct  11160
gcatgactcc taaaccataa tttctttttt gttttttttt ttttattttt gagacagggt  11220
ctcactctgt cacctaggct ggagtgcagt ggtgcaatca cagctcactg cagcctcaac  11280
gtcgtaagct caagcgatcc tcccacctca gcctgcctgg tagctgagac tacaagcgac  11340
gccccagtta atttttgtat ttttggtaga ggcagcgttt tgccgtgtgg ccctggctgg  11400
tctcgaactc ctgggctcaa gtgatccagc ctcagcctcc caaagtgctg ggacaaccgg  11460
ggccagtcac tgcacctggc cctaaaccat aatttctaat cttttggcta atttgttagt  11520
cctacaaagg cagtctagtc cccaggcaaa aagggggttt gtttcgggaa agggctgtta  11580
ctgtctttgt ttcaaactat aaactaagtt cctcctaaac ttagttcggc ctacacccag  11640
gaatgaacaa ggagagcttg gaggttagaa gcacgatgga attggttagg tcagatctct  11700
ttcactgtct gagttataat tttgcaatgg tggttcaaag actgcccgct tctgacacca  11760
gtcgctgcat taatgaatcg gccaacgcgc ggggagaggc ggtttgcgta ttggcgctct  11820
tccgcttcct cgctcactga ctcgctgcgc tcggtcgttc ggctgcggcg agcggtatca  11880
gctcactcaa aggcggtaat acggttatcc acagaatcag gggataacgc aggaaagaac  11940
atgtgagcaa aaggccagca aaaggccagg aaccgtaaaa aggccgcgtt gctggcgttt  12000
ttccataggc tccgcccccc tgacgagcat cacaaaaatc gacgctcaag tcagaggtgg  12060
cgaaacccga caggactata aagataccag gcgtttcccc ctggaagctc cctcgtgcgc  12120
tctcctgttc cgaccctgcc gcttaccgga tacctgtccg cctttctccc ttcgggaagc  12180
gtggcgcttt ctcaatgctc acgctgtagg tatctcagtt cggtgtaggt cgttcgctcc  12240
aagctgggct gtgtgcacga accccccgtt cagcccgacc gctgcgcctt atccggtaac  12300
tatcgtcttg agtccaaccc ggtaagacac gacttatcgc cactggcagc agccactggt  12360
aacaggatta gcagagcgag gtatgtaggc ggtgctacag agttcttgaa gtggtggcct  12420
aactacggct acactagaag gacagtattt ggtatctgcg ctctgctgaa gccagttacc  12480
ttcggaaaaa gagttggtag ctcttgatcc ggcaaacaaa ccaccgctgg tagcggtggt  12540
ttttttgttt gcaagcagca gattacgcgc agaaaaaaag gatctcaaga agatcctttg  12600
atcttttcta cggggtctga cgctcagtgg aacgaaaact cacgttaagg gattttggtc  12660
atgagattat caaaaaggat cttcacctag atccttttaa attaaaaatg aagttttaaa  12720
tcaatctaaa gtatatatga gtaaacttgg tctgacagtt accaatgctt aatcagtgag  12780
gcacctatct cagcgatctg tctatttcgt tcatccatag ttgcctgact ccccgtcgtg  12840
tagataacta cgatacggga gggcttacca tctggcccca gtgctgcaat gataccgcga  12900
gacccacgct caccggctcc agatttatca gcaataaacc agccagccgg aagggccgag  12960
cgcagaagtg gtcctgcaac tttatccgcc tccatccagt ctattaattg ttgccgggaa  13020
gctagagtaa gtagttcgcc agttaatagt ttgcgcaacg ttgttgccat tgctacaggc  13080
atcgtggtgt cacgctcgtc gtttggtatg gcttcattca gctccggttc ccaacgatca  13140
aggcgagtta catgatcccc catgttgtgc aaaaaagcgg ttagctcctt cggtcctccg  13200
atcgttgtca gaagtaagtt ggccgcagtg ttatcactca tggttatggc agcactgcat  13260
aattctctta ctgtcatgcc atccgtaaga tgcttttctg tgactggtga gtactcaacc  13320
aagtcattct gagaatagtg tatgcggcga ccgagttgct cttgcccggc gtcaatacgg  13380
```

```
gataataccg cgccacatag cagaacttta aaagtgctca tcattggaaa acgttcttcg  13440

gggcgaaaac tctcaaggat cttaccgctg ttgagatcca gttcgatgta acccactcgt  13500

gcacccaact gatcttcagc atcttttact ttcaccagcg tttctgggtg agcaaaaaca  13560

ggaaggcaaa atgccgcaaa aaagggaata agggcgacac ggaaatgttg aatactcata  13620

ctcttccttt ttcaatatta ttgaagcatt tatcagggtt attgtctcat gagcggatac  13680

atatttgaat gtatttagaa aaataaacaa ataggggttc cgcgcacatt tccccgaaaa  13740

gtgccacctg acgtctaaga aaccattatt atcatgacat taacctataa aaataggcgt  13800

atcacgaggc cctttcgtct tcaagaactg cctcgcgcgt ttcggtgatg acggtgaaaa  13860

cctctgacac atgcagctcc cggagacggt cacagcttgt ctgtaagcgg atgccgggag  13920

cagacaagcc cgtcagggcg cgtcagcggg tgttggcggg tgtcggggcg cagccatgac  13980

ccagtcacgt agcgatagcg gagtgtactg gcttaactat gcggcatcag agcagattgt  14040

actgagagtg caccatatgc ggtgtgaaat accgcacaga tgcgtaagga gaaaataccg  14100

catcaggcgc cattcgccat tcaggctgcg caactgttgg gaagggcgat cggtgcgggc  14160

ctcttcgcta ttacgccagg ggaggcagag attgcagtaa gctgagatcg cagcactgca  14220

ctccagcctg ggcgacagag taagactctg tctcaaaaat aaaataaata aatcaatcag  14280

atattccaat cttttccttt atttatttat ttattttcta ttttggaaac acagtccttc  14340

cttattccag aattacacat atattctatt tttctttata tgctccagtt ttttttagac  14400

cttcacctga aatgtgtgta tacaaaatct aggccagtcc agcagagcct aaaggtaaaa  14460

aataaaataa taaaaaataa ataaaatcta gctcactcct tcacatcaaa atggagatac  14520

agctgttagc attaaatacc aaataaccca tcttgtcctc aataatttta agcgcctctc  14580

tccaccacat ctaactcctg tcaaaggcat gtgccccttc cgggcgctct gctgtgctgc  14640

caaccaactg gcatgtggac tctgcagggt ccctaactgc caagccccac agtgtgccct  14700

gaggctgccc cttccttcta gcggctgccc ccactcggct ttgctttccc tagtttcagt  14760

tacttgcgtt cagccaaggt ctgaaactag gtgcgcacag agcggtaaga ctgcgagaga  14820

aagagaccag ctttacaggg ggtttatcac agtgcaccct gacagtcgtc agcctcacag  14880

ggggtttatc acattgcacc ctgacagtcg tcagcctcac agggggttta tcacagtgca  14940

cccttacaat cattccattt gattcacaat ttttttagtc tctactgtgc ctaacttgta  15000

agttaaattt gatcagaggt gtgttcccag aggggaaaac agtatataca gggttcagta  15060

ctatcgcatt tcaggcctcc acctgggtct tggaatgtgt cccccgaggg gtgatgacta  15120

cctcagttgg atctccacag gtcacagtga cacaagataa ccaagacacc tcccaaggct  15180

accacaatgg gccgccctcc acgtgcacat ggccggagga actgccatgt cggaggtgca  15240

agcacacctg cgcatcagag tccttggtgt ggagggaggg accagcgcag cttccagcca  15300

tccacctgat gaacagaacc tagggaaagc cccagttcta cttacaccag gaaaggc     15357
```

<210> SEQ ID NO 11
<211> LENGTH: 15414
<212> TYPE: DNA
<213> ORGANISM: Human immunodeficiency virus type 1

<400> SEQUENCE: 11

```
tggaagggct aatttggtcc caaaaaagac aagagatcct tgatctgtgg atctaccaca     60

cacaaggcta cttccctgat tggcagaact acacaccagg gccagggatc agatatccac    120
```

```
tgacctttgg atggtgcttc aagttagtac cagttgaacc agagcaagta gaagaggcca    180
aataaggaga gaagaacagc ttgttacacc ctatgagcca gcatgggatg gaggacccgg    240
agggagaagt attagtgtgg aagtttgaca gcctcctagc atttcgtcac atggcccgag    300
agctgcatcc ggagtactac aaagactgct gacatcgagc tttctacaag ggactttccg    360
ctggggactt tccagggagg tgtggcctgg gcgggactgg ggagtggcga gccctcagat    420
gctacatata agcagctgct ttttgcctgt actgggtctc tctggttaga ccagatctga    480
gcctgggagc tctctggcta actagggaac ccactgctta agcctcaata aagcttgcct    540
tgagtgctca aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagtaaa gccagaggag atctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcggta ttaagcgggg gagaattaga taaatgggaa    840
aaaattcggt taaggccagg gggaaagaaa caatataaac taaaacatat agtatgggca    900
agcagggagc tagaacgatt cgcagttaat cctggccttt tagagacatc agaaggctgt    960
agacaaatac tgggacagct acaaccatcc cttcagacag gatcagaaga acttagatca   1020
ttatataata caatagcagt cctctattgt gtgcatcaaa ggatagatgt aaaagacacc   1080
aaggaagcct tagataagat agaggaagag caaaacaaaa gtaagaaaaa ggcacagcaa   1140
gcagcagctg acacaggaaa caacagccag gtcagccaaa attaccctat agtgcagaac   1200
ctccaggggc aaatggtaca tcaggccata tcacctagaa ctttaaatgc atgggtaaaa   1260
gtagtagaag agaaggcttt cagcccagaa gtaataccca tgttttcagc attatcagaa   1320
ggagccaccc cacaagattt aaataccatg ctaaacacag tgggggggaca tcaagcagcc   1380
atgcaaatgt taaaagagac catcaatgag gaagctgcag aatgggatag attgcatcca   1440
gtgcatgcag ggcctattgc accaggccag atgagagaac caaggggaag tgacatagca   1500
ggaactacta gtacccttca ggaacaaata ggatggatga cacataatcc acctatccca   1560
gtaggagaaa tctataaaag atggataatc ctgggattaa ataaaatagt aagaatgtat   1620
agccctacca gcattctgga cataagacaa ggaccaaagg aaccctttag agactatgta   1680
gaccgattct ataaaactct aagagccgag caagcttcac aagaggtaaa aaattggatg   1740
acagaaacct tgttggtcca aaatgcgaac ccagattgta agactatttt aaaagcattg   1800
ggaccaggag cgacactaga agaaatgatg acagcatgtc agggagtggg gggacccggc   1860
cataaagcaa gagttttggc tgaagcaatg agccaagtaa caaatccagc taccataatg   1920
atacagaaag gcaattttag gaaccaaaga aagactgtta agtgtttcaa ttgtggcaaa   1980
gaagggcaca tagccaaaaa ttgcagggcc cctaggaaaa agggctgttg gaaatgtgga   2040
aaggaaggac accaaatgaa agattgtact gagagacagg ctaatttttt agggaagatc   2100
tggccttccc acaagggaag gccagggaat tttcttcaga gcagaccaga gccaacagcc   2160
ccaccagaag agagcttcag gtttggggaa gagacaacaa ctccctctca gaagcaggag   2220
ccgatagaca aggaactgta tcctttagct tccctcagat cactctttgg cagcgacccc   2280
tcgtcacaat aaagataggg ggcaattaa aggaagctct attagataca ggagcagatg   2340
atacagtatt agaagaaatg aatttgccag gaagatggaa accaaaaatg atagggggaa   2400
ttggaggttt tatcaaagta ggacagtatg atcagatact catagaaatc tgcggacata   2460
aagctatagg tacagtatta gtaggaccta cacctgtcaa cataattgga agaaatctgt   2520
```

```
tgactcagat tggctgcact ttaaattttc ccattagtcc tattgagact gtaccagtaa   2580
aattaaagcc aggaatggat ggcccaaaag ttaaacaatg gccattgaca gaagaaaaaa   2640
taaaagcatt agtagaaatt tgtacagaaa tggaaaagga aggaaaaatt tcaaaaattg   2700
ggcctgaaaa tccatacaat actccagtat ttgccataaa gaaaaaagac agtactaaat   2760
ggagaaaatt agtagatttc agagaactta ataagagaac tcaagatttc tgggaagttc   2820
aattaggaat accacatcct gcagggttaa aacagaaaaa atcagtaaca gtactggatg   2880
tgggcgatgc atatttttca gttcccttag ataaagactt caggaagtat actgcattta   2940
ccatacctag tataaacaat gagacaccag ggattagata tcagtacaat gtgcttccac   3000
agggatggaa aggatcacca gcaatattcc agtgtagcat gacaaaaatc ttagagcctt   3060
ttagaaaaca aaatccagac atagtcatct atcaatacat ggatgatttg tatgtaggat   3120
ctgacttaga aatagggcag catagaacaa aaatagagga actgagacaa catctgttga   3180
ggtggggatt taccacacca gacaaaaaac atcagaaaga acctccattc ctttggatgg   3240
gttatgaact ccatcctgat aaatggacag tacagcctat agtgctgcca gaaaaggaca   3300
gctggactgt caatgacata cagaaattag tgggaaaatt gaattgggca agtcagattt   3360
atgcagggat taaagtaagg caattatgta aacttcttag gggaaccaaa gcactaacag   3420
aagtagtacc actaacagaa gaagcagagc tagaactggc agaaaacagg gagattctaa   3480
aagaaccggt acatggagtg tattatgacc catcaaaaga cttaatagca gaaatacaga   3540
agcaggggca aggccaatgg acatatcaaa tttatcaaga gccatttaaa aatctgaaaa   3600
caggaaaata tgcaagaatg aagggtgccc acactaatga tgtgaaacaa ttaacagagg   3660
cagtacaaaa aatagccaca gaaagcatag taatatgggg aaagactcct aaatttaaat   3720
tacccataca aaaggaaaca tggaagcat ggtggacaga gtattggcaa gccacctgga   3780
ttcctgagtg ggagtttgtc aatacccctc ccttagtgaa gttatggtac cagttagaga   3840
aagaacccat aataggagca gaaactttct atgtagatgg ggcagccaat agggaaacta   3900
aattaggaaa agcaggatat gtaactgaca gaggaagaca aaaagttgtc cccctaacgg   3960
acacaacaaa tcagaagact gagttacaag caattcatct agctttgcag gattcgggat   4020
tagaagtaaa catagtgaca gactcacaat atgcattggg aatcattcaa gcacaaccag   4080
ataagagtga atcagagtta gtcagtcaaa taatagagca gttaataaaa aaggaaaaag   4140
tctacctggc atgggtacca gcacacaaag gaattggagg aaatgaacaa gtagatgggt   4200
tggtcagtgc tggaatcagg aaagtactat ttttagatgg aatagataag gcccaagaag   4260
aacatgagaa atatcacagt aattggagag caatggctag tgattttaac ctaccacctg   4320
tagtagcaaa agaaatagta gccagctgtg ataaatgtca gctaaaaggg gaagccatgc   4380
atggacaagt agactgtagc ccaggaatat ggcagctaga ttgtacacat ttagaaggaa   4440
aagttatctt ggtagcagtt catgtagcca gtggatatat agaagcagaa gtaattccag   4500
cagagacagg gcaagaaaca gcatacttcc tcttaaaatt agcaggaaga tggccagtaa   4560
aaacagtaca tacagacaat ggcagcaatt tcaccagtac tacagttaag gccgcctgtt   4620
ggtgggcggg gatcaagcag gaatttggca ttccctacaa tccccaaagt caaggagtaa   4680
tagaatctat gaataaagaa ttaaagaaaa ttataggaca ggtaagagat caggctgaac   4740
atcttaagac agcagtacaa atggcagtat tcatccacaa ttttaaaaga aaagggggga   4800
ttggggggta cagtgcaggg gaaagaatag tagacataat agcaacagac atacaaacta   4860
```

```
aagaattaca aaaacaaatt acaaaaattc aaaattttcg ggtttattac agggacagca   4920
gagatccagt ttggaaagga ccagcaaagc tcctctggaa aggtgaaggg gcagtagtaa   4980
tacaagataa tagtgacata aaagtagtgc caagaagaaa agcaaagatc atcagggatt   5040
atggaaaaca gatggcaggt gatgattgtg tggcaagtag acaggatgag gattaacaca   5100
tggaaaagat tagtaaaaca ccatatgtat atttcaagga aagctaagga ctggttttat   5160
agacatcact atgaaagtac taatccaaaa ataagttcag aagtacacat cccactaggg   5220
gatgctaaat tagtaataac aacatattgg ggtctgcata caggagaaag agactggcat   5280
ttgggtcagg gagtctccat agaatggagg aaaaagagat atagcacaca agtagaccct   5340
gacctagcag accaactaat tcatctgcac tattttgatt gtttttcaga atctgctata   5400
agaaatacca tattaggacg tatagttagt cctaggtgtg aatatcaagc aggacataac   5460
aaggtaggat ctctacagta cttggcacta gcagcattaa taaaaccaaa acagataaag   5520
ccacctttgc ctagtgttag gaaactgaca gaggacagat ggaacaagcc ccagaagacc   5580
aagggccaca gagggagcca tacaatgaat ggacactaga gcttttagag gaacttaaga   5640
gtgaagctgt tagacatttt cctaggatat ggctccataa cttaggacaa catatctatg   5700
aaacttacgg ggatacttgg gcaggagtgg aagccataat aagaattctg caacaactgc   5760
tgtttatcca tttcagaatt gggtgtcgac atagcagaat aggcgttact cgacagagga   5820
gagcaagaaa tggagccagt agatcctaga ctagagccct ggaagcatcc aggaagtcag   5880
cctaaaactg cttgtaccaa ttgctattgt aaaaagtgtt gctttcattg ccaagtttgt   5940
ttcatgacaa aagccttagg catctcctat ggcaggaaga agcggagaca gcgacgaaga   6000
gctcatcaga acagtcagac tcatcaagct tctctatcaa agcagtaagt agtacatgta   6060
atgcaaccta taatagtagc aatagtagca ttagtagtag caataataat agcaatagtt   6120
gtgtggtcca tagtaatcat agaatatagg aaaatattaa gacaaagaaa aatagacagg   6180
ttaattgata gactaataga aagagcagaa gacagtggca atgagagtga aggagaagta   6240
tcagcacttg tggagatggg ggtggaaatg gggcaccatg ctccttggga tattgatgat   6300
ctgtagtgct acagaaaaat tgtgggtcac cgtctattat ggggtacctg tgtggaaaga   6360
agcaaccacc actctatttt gtgcatcaga tgctaaagca tatgatacag aggtacataa   6420
tgtttgggcc acacatgcct gtgtacccac agaccccaac ccacaagaag tagtattgga   6480
aaatgtaaca gaacatttta acatgtggaa aaataacatg gtagaacaga tgcaggagga   6540
tataatcagt ttatgggatc aaagcctaaa gccatgtgta aaattaaccc cactctgtgt   6600
tactttaaat tgcaaggatg tgaatgctac taataccact aatgatagcg agggaacgat   6660
ggagagagga gaaataaaaa actgctcttt caatatcacc acaagcataa gagatgaggt   6720
gcagaaagaa tatgctcttt tttataaact tgatgtagta ccaatagata ataataatac   6780
cagctatagg ttgataagtt gtgacacctc agtcattaca caggcctgtc caaagatatc   6840
ctttgagcca attcccatac attattgtgc cccggctggt tttgcgattc taaagtgtaa   6900
tgataagacg ttcaatggaa aaggaccatg taaaaatgtc agcacagtac aatgtacaca   6960
tggaattagg ccagtagtat caactcaact gctgctaaat ggcagtctag cagaagaaga   7020
ggtagtaatt agatctgaca atttcacgaa caatgctaaa accataatag tacagctgaa   7080
agaatctgta gaaattaatt gtacaagacc caacaacaat acaagaaaaa gtatacatat   7140
aggaccaggg agagcatttt atactacagg agaaataata ggagatataa gacaagcaca   7200
ttgtaacatt agtagagcaa aatggaatga cactttaaaa cagatagtta taaaattaag   7260
```

```
agaacaattt gagaataaaa caatagtctt taatcactcc tcaggagggg acccagaaat   7320
tgtaatgcac agttttaatt gtggaggaga atttttctac tgtaattcaa cacaactgtt   7380
taatagtact tggaataata atactgaagg gtcaaataac actgaaggaa atactatcac   7440
actcccatgc agaataaaac aaattataaa catgtggcag gaagtaggaa aagcaatgta   7500
tgcccctccc atcagaggac aaattagatg ttcatcaaat attacagggc tgctattaac   7560
aagagatggt ggtattaatg agaatgggac cgagatcttc agacctggag gaggagatat   7620
gagggacaat tggagaagtg aattatataa atataaagta gtaaaaattg aaccattagg   7680
agtagcaccc accaaggcaa agagaagagt ggtgcaaaga gaaaaaagag cagtgggaat   7740
aggagctgtg ttccttgggt tcttgggagc agcaggaagc actatgggcg cagcgtcaat   7800
gacactgacg gtacaggcca gactattatt gtctggtata gtgcaacagc agaacaattt   7860
gctgagggct attgaggcgc aacagcgtat gttgcaactc acagtctggg gcatcaagca   7920
gctccaggca agagtcctgg ctgtggaaag atacctaggg gatcaacagc tcctggggat   7980
ttggggttgc tctggaaaac tcatttgcac cactgctgtg ccttggaatg ctagttggag   8040
taataaatct ctggatagga tttggaataa catgacctgg atggagtggg aaagagaaat   8100
tgacaattac acaagcgaaa tatacaccct aattgaagaa tcgcagaacc aacaagaaaa   8160
gaatgaacaa gaattattgg aattagataa atgggcaagt ttgtggaatt ggtttgacat   8220
aacaaaatgg ctgtggtata taaaaatatt cataatgata gtaggaggct tagtaggttt   8280
aagactagtt tttactgtac tttctatagt gaatagagtt aggcagggat actcaccatt   8340
atcgtttcag accctcctcc cagccccgag gggacccgac aggcccgaag gaatcgaaga   8400
agaaggtgga gagagagaca gagacagatc cggacgatta gtgaacggat tcttagcact   8460
tatctgggtc gacctgcgga gcctgtgcct cttcagctac caccgcttga gagacttact   8520
cttgactgta acgaggattg tggaacttct gggacgcagg gggtgggaag tcctgaaata   8580
ttggtggaat ctcctacagt attggagtca ggaactaaag aatagtgctg ttagcttgct   8640
caatgccaca gccatagcag tagctgaggg gacagatagg attatagaag cattacaaag   8700
aacttataga gctattctcc acatacctac aagaataaga cagggcttgg aaagggcttt   8760
gctataagcg gccgccatgg gcaagcagaa tgtcagtagc ctggatgaga aaaatagcgt   8820
gagcgtggac ctgcctggag aaatgaaagt gctggtgtca aaggagaaga acaaagacgg   8880
gaagtacgat ctgatcgcca ccgtggacaa actggaactg aagggcacat ctgataaaaa   8940
caatggcagt ggggtgctgg agggggtcaa ggctgacaag tcaaaagtca agctgaccat   9000
tagcgacgat ctgggacaga ccacactgga agtgttcaaa gaggacggca agaccctggt   9060
gagcaagaaa gtcacatcca aagataagag ctccactgag gaaaagttca acgagaaggg   9120
cgaagtgagc gagaagatca ttacacgggc cgacggcact agactggaat acaccgggat   9180
caagtccgat ggatctggca aagctaagga ggtgctgaag ggctatgtcc tggaaggaac   9240
actgactgca gagaaaacta ccctggtggt caaggaaggg accgtgacac tgtccaaaaa   9300
catttcaaag agcggagaag tgtctgtcga gctgaatgac accgattcta gtgccgctac   9360
taagaaaacc gcagcctgga acagtggaac ttcaaccctg acaatcactg tgaatagtaa   9420
gaaaacaaag gacctggtct tcactaagga gaacaccatt acagtgcagc agtatgatag   9480
caatggcaca aagctggaag gctccgccgt ggaaatcacc aaactggatg aaatcaaaaa   9540
tgctctgaag taacccgggt acctttaaga ccaatgactt acaaggcagc tgtagatctt   9600
```

```
agccactttt taaaagaaaa gggggactg gaagggctaa ttcactccca aagaagacaa   9660

gatatccttg atctgtggat ctaccacaca caaggctact tccctgattg gcagaactac   9720

acaccagggc caggggtcag atatccactg acctttggat ggtgctacaa gctagtacca   9780

gttgagccag ataaggtaga agaggccaat aaaggagaga acaccagctt gttacaccct   9840

gtgagcctgc atggaatgga tgaccctgag agagaagtgt tacgcctagc atttcatcac   9900

gtggcccgag agctgcatcc ggagtacttc aagaactgct gacatcgagc ttgctacaag   9960

ggactttccg ctggggactt tccagggagg cgtggcctgg gcgggactgg ggagtggcga  10020

gccctcagat gctgcatata agcagctgct ttttgcctgt actgggtctc tctggttaga  10080

ccagatctga gcctgggagc tctctggcta actagggaac ccactgctta agcctcaata  10140

aagcttgcct tgagtgcttc aagtagtgtg tgcccgtctg ttgtgtgact ctggtaacta  10200

gagatccctc agaccctttt agtcagtgtg gaaaatctct agcacccccc aggaggtaga  10260

ggttgcagtg agccaagatc gcgccactgc attccagcct gggcaagaaa acaagactgt  10320

ctaaaataat aataataagt taagggtatt aaatatattt atacatggag gtcataaaaa  10380

tatatatatt tgggctgggc gcagtggctc acacctgcgc ccggcccttt gggaggccga  10440

ggcaggtgga tcacctgagt ttgggagttc cagaccagcc tgaccaacat ggagaaaccc  10500

cttctctgtg tatttttagt agattttatt ttatgtgtat tttattcaca ggtatttctg  10560

gaaaactgaa actgtttttc ctctactctg ataccacaag aatcatcagc acagaggaag  10620

acttctgtga tcaaatgtgg tgggagaggg aggttttcac cagcacatga gcagtcagtt  10680

ctgccgcaga ctcggcgggt gtccttcggt tcagttccaa caccgcctgc ctggagagag  10740

gtcagaccac agggtgaggg ctcagtcccc aagacataaa cacccaagac ataaacaccc  10800

aacaggtcca ccccgcctgc tgcccaggca gagccgattc accaagacgg gaattaggat  10860

agagaaagag taagtcacac agagccggct gtgcgggaga acggagttct attatgactc  10920

aaatcagtct ccccaagcat tcggggatca gagtttttaa ggataactta gtgtgtaggg  10980

ggccagtgag ttggagatga aagcgtaggg agtcgaaggt gtccttttgc gccgagtcag  11040

ttcctgggtg ggggccacaa gatcggatga gccagtttat caatccgggg gtgccagctg  11100

atccatggag tgcagggtct gcaaaatatc tcaagcactg attgatctta ggttttacaa  11160

tagtgatgtt accccaggaa caatttgggg aaggtcagaa tcttgtagcc tgtagctgca  11220

tgactcctaa accataattt ctttttgtt tttttttttt tatttttgag acagggtctc  11280

actctgtcac ctaggctgga gtgcagtggt gcaatcacag ctcactgcag cctcaacgtc  11340

gtaagctcaa gcgatcctcc cacctcagcc tgcctggtag ctgagactac aagcgacgcc  11400

ccagttaatt tttgtatttt tggtagaggc agcgttttgc cgtgtggccc tggctggtct  11460

cgaactcctg ggctcaagtg atccagcctc agcctcccaa agtgctggga caaccggggc  11520

cagtcactgc acctggccct aaaccataat ttctaatctt ttggctaatt tgttagtcct  11580

acaaaggcag tctagtcccc aggcaaaaag gggtttgtt tcgggaaagg gctgttactg  11640

tctttgtttc aaactataaa ctaagttcct cctaaactta gttcggccta cacccaggaa  11700

tgaacaagga gagcttggag gttagaagca cgatggaatt ggttaggtca gatctctttc  11760

actgtctgag ttataatttt gcaatggtgg ttcaaagact gcccgcttct gacaccagtc  11820

gctgcattaa tgaatcggcc aacgcgcggg gagaggcggt ttgcgtattg gcgctcttcc  11880

gcttcctcgc tcactgactc gctgcgctcg gtcgttcggc tgcggcgagc ggtatcagct  11940

cactcaaagg cggtaatacg gttatccaca gaatcagggg ataacgcagg aaagaacatg  12000
```

```
tgagcaaaag gccagcaaaa ggccaggaac cgtaaaaagg ccgcgttgct ggcgtttttc  12060
cataggctcc gcccccctga cgagcatcac aaaaatcgac gctcaagtca gaggtggcga  12120
aacccgacag gactataaag ataccaggcg tttccccctg gaagctccct cgtgcgctct  12180
cctgttccga ccctgccgct taccggatac ctgtccgcct ttctcccttc gggaagcgtg  12240
gcgctttctc aatgctcacg ctgtaggtat ctcagttcgg tgtaggtcgt tcgctccaag  12300
ctgggctgtg tgcacgaacc ccccgttcag cccgaccgct gcgccttatc cggtaactat  12360
cgtcttgagt ccaacccggt aagacacgac ttatcgccac tggcagcagc cactggtaac  12420
aggattagca gagcgaggta tgtaggcggt gctacagagt tcttgaagtg gtggcctaac  12480
tacggctaca ctagaaggac agtatttggt atctgcgctc tgctgaagcc agttaccttc  12540
ggaaaaagag ttggtagctc ttgatccggc aaacaaacca ccgctggtag cggtggtttt  12600
tttgtttgca agcagcagat tacgcgcaga aaaaaaggat ctcaagaaga tcctttgatc  12660
ttttctacgg ggtctgacgc tcagtggaac gaaaactcac gttaagggat tttggtcatg  12720
agattatcaa aaaggatctt cacctagatc cttttaaatt aaaaatgaag ttttaaatca  12780
atctaaagta tatatgagta aacttggtct gacagttacc aatgcttaat cagtgaggca  12840
cctatctcag cgatctgtct atttcgttca tccatagttg cctgactccc cgtcgtgtag  12900
ataactacga tacgggaggg cttaccatct ggccccagtg ctgcaatgat accgcgagac  12960
ccacgctcac cggctccaga tttatcagca ataaaccagc cagccggaag ggccgagcgc  13020
agaagtggtc ctgcaacttt atccgcctcc atccagtcta ttaattgttg ccgggaagct  13080
agagtaagta gttcgccagt taatagtttg cgcaacgttg ttgccattgc tacaggcatc  13140
gtggtgtcac gctcgtcgtt tggtatggct tcattcagct ccggttccca acgatcaagg  13200
cgagttacat gatcccccat gttgtgcaaa aaagcggtta gctccttcgg tcctccgatc  13260
gttgtcagaa gtaagttggc cgcagtgtta tcactcatgg ttatggcagc actgcataat  13320
tctcttactg tcatgccatc cgtaagatgc ttttctgtga ctggtgagta ctcaaccaag  13380
tcattctgag aatagtgtat gcggcgaccg agttgctctt gcccggcgtc aatacgggat  13440
aataccgcgc cacatagcag aactttaaaa gtgctcatca ttggaaaacg ttcttcgggg  13500
cgaaaactct caaggatctt accgctgttg agatccagtt cgatgtaacc cactcgtgca  13560
cccaactgat cttcagcatc ttttactttc accagcgttt ctgggtgagc aaaaacagga  13620
aggcaaaatg ccgcaaaaaa gggaataagg gcgacacgga aatgttgaat actcatactc  13680
ttcctttttc aatattattg aagcatttat cagggttatt gtctcatgag cggatacata  13740
tttgaatgta tttagaaaaa taaacaaata ggggttccgc gcacatttcc ccgaaaagtg  13800
ccacctgacg tctaagaaac cattattatc atgacattaa cctataaaaa taggcgtatc  13860
acgaggccct ttcgtcttca agaactgcct cgcgcgtttc ggtgatgacg gtgaaaacct  13920
ctgacacatg cagctcccgg agacggtcac agcttgtctg taagcggatg ccgggagcag  13980
acaagcccgt cagggcgcgt cagcgggtgt tggcgggtgt cggggcgcag ccatgaccca  14040
gtcacgtagc gatagcggag tgtactggct taactatgcg gcatcagagc agattgtact  14100
gagagtgcac catatgcggt gtgaaatacc gcacagatgc gtaaggagaa aataccgcat  14160
caggcgccat tcgccattca ggctgcgcaa ctgttgggaa gggcgatcgg tgcgggcctc  14220
ttcgctatta cgccagggga ggcagagatt gcagtaagct gagatcgcag cactgcactc  14280
cagcctgggc gacagagtaa gactctgtct caaaaataaa ataaataaat caatcagata  14340
```

```
ttccaatctt ttcctttatt tatttattta ttttctattt tggaaacaca gtccttcctt  14400

attccagaat tacacatata ttctattttt ctttatatgc tccagttttt tttagacctt  14460

cacctgaaat gtgtgtatac aaaatctagg ccagtccagc agagcctaaa ggtaaaaaat  14520

aaaataataa aaaataaata aaatctagct cactccttca catcaaaatg gagatacagc  14580

tgttagcatt aaataccaaa taacccatct tgtcctcaat aattttaagc gcctctctcc  14640

accacatcta actcctgtca aaggcatgtg ccccttccgg gcgctctgct gtgctgccaa  14700

ccaactggca tgtggactct gcagggtccc taactgccaa gccccacagt gtgccctgag  14760

gctgcccctt ccttctagcg gctgccccca ctcggctttg ctttccctag tttcagttac  14820

ttgcgttcag ccaaggtctg aaactaggtg cgcacagagc ggtaagactg cgagagaaag  14880

agaccagctt tacagggggt ttatcacagt gcaccctgac agtcgtcagc ctcacagggg  14940

gtttatcaca ttgcaccctg acagtcgtca gcctcacagg gggtttatca cagtgcaccc  15000

ttacaatcat tccatttgat tcacaatttt tttagtctct actgtgccta acttgtaagt  15060

taaatttgat cagaggtgtg ttcccagagg ggaaaacagt atatacaggg ttcagtacta  15120

tcgcatttca ggcctccacc tgggtcttgg aatgtgtccc ccgaggggtg atgactacct  15180

cagttggatc tccacaggtc acagtgacac aagataacca agacacctcc caaggctacc  15240

acaatgggcc gccctccacg tgcacatggc cggaggaact gccatgtcgg aggtgcaagc  15300

acacctgcgc atcagagtcc ttggtgtgga gggagggacc agcgcagctt ccagccatcc  15360

acctgatgaa cagaacctag ggaaagcccc agttctactt acaccaggaa aggc        15414
```

<210> SEQ ID NO 12
<211> LENGTH: 2468
<212> TYPE: DNA
<213> ORGANISM: Human immunodeficiency virus type 1

<400> SEQUENCE: 12

```
atgagagtga aggagaagta tcagcacttg tggagatggg ggtggaaatg gggcaccatg     60

ctccttggga tattgatgat ctgtagtgct acagaaaaat tgtgggtcac agtctattat    120

ggggtacctg tgtggaagga agcaaccacc actctatttt gtgcatcaga tgctaaagca    180

tatgatacag aggtacataa tgtttgggcc acacatgcct gtgtacccac agaccccaac    240

ccacaagaag tagtattggt aaatgtgaca gaaaatttta acatgtggaa aaatgacatg    300

gtagaacaga tgcatgagga tataatcagt ttatgggatc aaagcctaaa gccatgtgta    360

aaattaaccc cactctgtgt tagtttaaag tgcactgatt tgaagaatga tactaatacc    420

aatagtagta gcgggagaat gataatggag aaaggagaga taaaaaactg ctctttcaat    480

atcagcacaa gcataagaga taaggtgcag aaagaatatg cattctttta taaacttgat    540

atagtaccaa tagataatac cagctatagg ttgataagtt gtaacacctc agtcattaca    600

caggcctgtc caaaggtatc ctttgagcca attcccatac attattgtgc cccggctggt    660

tttgcgattc taaaatgtaa taataagacg ttcaatggaa caggaccatg tacaaatgtc    720

agcacagtac aatgtacaca tggaatcagg ccagtagtat caactcaact gctgttaaat    780

ggcagtctag cagaagaaga tgtagtaatt agatctgcca atttcacaga caatgctaaa    840

accataatag tacagctgaa cacatctgta gaaattaatt gtacaagacc caacaacaat    900

acaagaaaaa gtatccgtat ccagagggga ccagggagag catttgttac aataggaaaa    960

ataggaaata tgagacaagc acattgtaac attagtagag caaaatggaa tgccacttta   1020

aaacagatag ctagcaaatt aagagaacaa tttggaaata ataaaacaat aatctttaag   1080
```

```
caatcctcag gaggggaccc agaaattgta acgcacagtt ttaattgtgg aggggaattt   1140
ttctactgta attcaacaca actgtttaat agtacttggt ttaatagtac ttggagtact   1200
gaagggtcaa ataacactga aggaagtgac acaatcacac tcccatgcag aataaaacaa   1260
tttataaaca tgtggcagga agtaggaaaa gcaatgtatg cccctcccat cagtggacaa   1320
attagatgtt catcaaatat tactgggctg ctattaacaa gagatggtgg taataacaac   1380
aatgggtccg agatcttcag acctggagga ggcgatatga gggacaattg gagaagtgaa   1440
ttatataaat ataaagtagt aaaaattgaa ccattaggag tagcacccac caaggcaaag   1500
agaagagtgg tgcagagaga aaaaagagca gtgggaatag gagctttgtt ccttgggttc   1560
ttgggagcag caggaagcac tatgggcgca gcgtcaatga cgctgacggt acaggccaga   1620
caattattgt ctgatatagt gcagcagcag aacaatttgc tgagggctat tgaggcgcaa   1680
cagcatctgt tgcaactcac agtctggggc atcaaacagc tccaggcaag aatcctggct   1740
gtggaaagat acctaaagga tcaacagctc ctggggattt ggggttgctc tggaaaactc   1800
atttgcacca ctgctgtgcc ttggaatgct agttggagta ataaatctct ggaacagatt   1860
tggaataaca tgacctggat ggagtgggac agagaaatta acaattacac aagcttaata   1920
cactccttaa ttgaagaatc gcaaaaccag caagaaaaga atgaacaaga attattggaa   1980
ttagataaat gggcaagttt gtggaattgg tttaacataa caaattggct gtggtatata   2040
aaattattca taatgatagt aggaggcttg gtaggtttaa gaatagtttt tgctgtactt   2100
tctatagtga atagagttag gcagggatat tcaccattat cgtttcagac ccacctccca   2160
atcccgaggg gacccgacag gcccgaagga atagaagaag aaggtggaga gagagacaga   2220
gacagatcca ttcgattagt gaacggatcc ttagcactta tctgggacga tctgcggagc   2280
ctgtgcctct tcagctacca ccgcttgaga gacttactct tgattgtaac gaggattgtg   2340
gaacttctgg gacgcagggg gtgggaagcc ctcaaatatt ggtggaatct cctacagtat   2400
tggagtcagg aactaaagaa tagtgctgtt aacttgctca atgccacagc catagcagta   2460
gctgaggg                                                            2468
```

```
<210> SEQ ID NO 13
<211> LENGTH: 2565
<212> TYPE: DNA
<213> ORGANISM: Human immunodeficiency virus type 1

<400> SEQUENCE: 13

atgagagtga aggagaagta tcagcacttg tggagatggg ggtggaaatg gggcaccatg     60
ctccttggga tattgatgat ctgtagtgct acagaaaaat tgtgggtcac cgtctattat    120
ggggtacctg tgtggaagga agcaaccacc actctatttt gtgcatcaga tgctaaagca    180
tatgatacag aggtacataa tgtttgggcc acacatgcct gtgtacccac agaccccaac    240
ccacaagaag tagtattggt aaatgtgaca gaaaatttta acatgtggaa aaatgacatg    300
gtagaacaga tgcatgagga tataatcagt ttatgggatc aaagcctaaa gccatgtgta    360
aaattaaccc cactctgtgt tagtttaaag tgcactgatt tgaagaatga tactaatacc    420
aatagtagta gcgggagaat gataatggag aaaggagaga taaaaaactg ctctttcaat    480
atcagcacaa gcataagaga taaggtgcag aaagaatatg cattctttta taaacttgat    540
atagtaccaa tagataatac cagctatagg ttgataagtt gtaacacctc agtcattaca    600
caggcctgtc caaaggtatc ctttgagcca attcccatac attattgtgc cccggctggt    660
```

-continued

```
tttgcgattc taaaatgtaa taataagacg ttcaatggaa caggaccatg tacaaatgtc     720

agcacagtac aatgtacaca tggaatcagg ccagtagtat caactcaact gctgttaaat     780

ggcagtctag cagaagaaga tgtagtaatt agatctgcca atttcacaga caatgctaaa     840

accataatag tacagctgaa cacatctgta gaaattaatt gtacaagacc caacaacaat     900

acaagaaaaa gtatccgtat ccagagggga ccagggagag catttgttac aataggaaaa     960

ataggaaata tgagacaagc acattgtaac attagtagag caaaatggaa tgccacttta    1020

aaacagatag ctagcaaatt aagagaacaa tttggaaata ataaaacaat aatctttaag    1080

caatcctcag gaggggaccc agaaattgta acgcacagtt ttaattgtgg aggggaattt    1140

ttctactgta attcaacaca actgtttaat agtacttggt ttaatagtac ttggagtact    1200

gaagggtcaa ataacactga aggaagtgac acaatcacac tcccatgcag aataaaacaa    1260

tttataaaca tgtggcagga agtaggaaaa gcaatgtatg cccctcccat cagtggacaa    1320

attagatgtt catcaaatat tactgggctg ctattaacaa gagatggtgg taataacaac    1380

aatgggtccg agatcttcag acctggagga ggcgatatga gggacaattg gagaagtgaa    1440

ttatataaat ataaagtagt aaaaattgaa ccattaggag tagcacccac caaggcaaag    1500

agaagagtgg tgcagagaga aaaaagagca gtgggaatag gagctttgtt ccttgggttc    1560

ttgggagcag caggaagcac tatgggcgca gcgtcaatga cgctgacggt acaggccaga    1620

caattattgt ctgatatagt gcagcagcag aacaatttgc tgagggctat tgaggcgcaa    1680

cagcatctgt tgcaactcac agtctggggc atcaaacagc tccaggcaag aatcctggct    1740

gtggaaagat acctaaagga tcaacagctc ctggggattt ggggttgctc tggaaaactc    1800

atttgcacca ctgctgtgcc ttggaatgct agttggagta ataaatctct ggaacagatt    1860

tggaataaca tgacctggat ggagtgggac agagaaatta acaattacac aagcttaata    1920

cactccttaa ttgaagaatc gcaaaaccag caagaaaaga atgaacaaga attattggaa    1980

ttagataaat gggcaagttt gtggaattgg tttaacataa caaattggct gtggtatata    2040

aaattattca taatgatagt aggaggcttg gtaggtttaa gaatagtttt tgctgtactt    2100

tctatagtga atagagttag gcagggatat tcaccattat cgtttcagac ccacctccca    2160

atcccgaggg gacccgacag gcccgaagga atagaagaag aaggtggaga gagagacaga    2220

gacagatcca ttcgattagt gaacggatcc ttagcactta tctgggacga tctgcggagc    2280

ctgtgcctct tcagctacca ccgcttgaga gacttactct tgattgtaac gaggattgtg    2340

gaacttctgg gacgcagggg gtgggaagcc ctcaaatatt ggtggaatct cctacagtat    2400

tggagtcagg aactaaagaa tagtgctgtt aacttgctca atgccacagc catagcagta    2460

gctgagggga cagatagggt tatagaagta ttacaagcag cttatagagc tattcgccac    2520

atacctagaa gaataagaca gggcttggaa aggattttgc tataa                    2565
```

<210> SEQ ID NO 14
<211> LENGTH: 2550
<212> TYPE: DNA
<213> ORGANISM: Human immunodeficiency virus type 1

<400> SEQUENCE: 14

```
atgagagtga aggagaagta tcagcacttg tggagatggg ggtggaaatg gggcaccatg      60

ctccttggga tattgatgat ctgtagtgct acagaaaaat tgtgggtcac cgtctattat     120

ggggtacctg tgtggaaaga aacaaccacc actctatttt gtgcatcaga tgctaaagca     180

tatgatacag aggtacataa tgtttgggcc acacatgcct gtgtacccac agaccccaac     240
```

```
ccacaagaag tagtattgga aaatgtaaca gaagatttta acatgtggaa aaataacatg    300
gtagaacaga tgcaggagga tgtaatcaat ttatgggatc aaagcttaaa gccatgtgta    360
aaattaaccc cactctgtgt tactttaaat tgcaaagatg tgaatgctac taataccact    420
agtagtagtg agggaatgat ggagagagga gaaataaaaa actgctcttt caatatcacc    480
aaaagcataa gagataaggt gcagaaagaa tatgctcttt tttataaact ggatgtagta    540
ccaatagata ataagaataa taccaaatat aggttaataa gttgtaacac ctcagtcatt    600
acacaagcct gtccaaaggt atcctttgaa ccaattccca tacattattg tgccccggct    660
ggttttgcga ttctaaagtg taataataag acattcaatg gaaaaggaca atgtaaaaat    720
gtcagcacag tacaatgtac acatggaatt aggccagtag tatcaactca actgctgcta    780
aatggcagtc tagcagaaga aaaggttgta attagatctg acaattttac ggacaatgct    840
aaaaccataa tagtacagct gaatgaatct gtaaaaatta attgtacaag gcccagcaac    900
aatacaagaa aaagtataca tataggacca gggagagcat tttatacaac aggagaaata    960
ataggagata taagacaagc acattgtaac attagtagag cacaatggaa taacacttta   1020
aaacagatag ttgaaaaatt aagagaacaa tttaataata aaacaatagt ctttactcac   1080
tcctcaggag gggatccaga aattgtaatg cacagtttta attgtggagg ggaatttttc   1140
tactgtaatt caacacaact gtttaatagt acttggaatg atactgaaaa gtcaagtggc   1200
actgaaggaa atgacaccat catactccca tgcagaataa aacaaattat aaacatgtgg   1260
caggaagtgg gaaaagcaat gtatgctcct cccattaaag gacaaattag atgttcatca   1320
aatattacag ggctgctatt aacaagagat ggtggtaaaa atgagagtga gatcgagatc   1380
ttcagacctg gaggaggaga catgagggac aattggagaa gtgaattata taaatataaa   1440
gtagtaaaaa ttgaaccatt aggagtagca cccaccaagg caaagagaag agtggtgcaa   1500
agagaaaaaa gagcagtggg aataggagct ttgttccttg ggttcttggg agcagcagga   1560
agcactatgg gcgcagcgtc aatgacactg acggtacagg ccagacaatt attgtctggt   1620
atagtgcaac agcaaaacaa tttgctgagg gctattgagg cgcaacagca tatgttgcaa   1680
ctcacagtct ggggcatcaa gcagctccag gcaagagtcc tggctgtgga aagataccta   1740
aaggatcaac agctcatggg gatttggggt tgctctggaa aactcatttg caccactgct   1800
gtgccttgga atactagttg gagtaataaa tctctggata gtatttggaa taacatgacc   1860
tggatggagt gggaaaaaga aattgagaat tacacaaaca caatatacac cctaattgaa   1920
gaatcgcaga tccaacaaga aaagaatgaa caagaattat tggaattaga taaatgggca   1980
agtttgtgga attggtttgg cataacaaaa tggctgtggt atataaaaat attcataatg   2040
atagtaggag gcttgatagg tttaagaata gtttttctg tactttctat agtgaataga   2100
gttaggcagg gatactcacc cttatcgttt cagaccctcc tcccagcaac gaggggaccc   2160
gacaggcccg aaggaatcga agaagaaggt ggagagagag acagagacag atccggacaa   2220
ttagtgaacg gattcttagc acttatctgg gtcgacctgc ggagcctgtt cctcttcagc   2280
taccaccgct tgagagactt actcttgact gtaacgagga ttgtggaact tctgggacgc   2340
agggggtggg aaatcctgaa atactggtgg aatctcctac agtattggag tcaggaacta   2400
aagaatagtg ctgttagctt gcttaatgcc acagctatag cagtagctga ggggacagat   2460
aggattatag aagtagtaca aagagtttat agggctattc tccacatacc tacaagaata   2520
agacagggct tggaaagggc tttgctataa                                    2550
```

<210> SEQ ID NO 15
<211> LENGTH: 2550
<212> TYPE: DNA
<213> ORGANISM: Human immunodeficiency virus type 1

<400> SEQUENCE: 15

```
atgagagtga aggagaagta tcagcacttg tggagatggg ggtggaaatg gggcaccatg     60

ctccttggga tattgatgat ctgtagtgct acagaaaaat tgtgggtcac cgtctattat    120

ggggtacctg tgtggaaaga aacaaccacc actctatttt gtgcatcaga tgctaaagca    180

tatgatacag aggtacataa tgtttgggcc acacatgcct gtgtacccac agaccccaac    240

ccacaagaag tagtattgga aaatgtaaca gaagatttta acatgtggaa aaataacatg    300

gtagaacaga tgcaggagga tgtaatcaat ttatgggatc aaagcttaaa gccatgtgta    360

aaattaaccc cactctgtgt tactttaaat tgcaaagatg tgaatgctac taataccact    420

agtagtagtg agggaatgat ggagagagga gaaataaaaa actgctcttt caatatcacc    480

aaaagcataa gagataaggt gcagaaagaa tatgctcttt tttataaact ggatgtagta    540

ccaatagata ataagaataa taccaaatat aggttaataa gttgtaacac ctcagtcatt    600

acacaagcct gtccaaaggt atcctttgaa ccaattccca tacattattg tgccccggct    660

ggttttgcga ttctaaagtg taataataag acattcaatg gaaaaggaca atgtaaaaat    720

gtcagcacag tacaatgtac acatggaatt aggccagtag tatcaactca actgctgcta    780

aatggcagtc tagcagaaga aaaggttgta attagatctg acaattttac ggacaatgct    840

aaaaccataa tagtacagct gaatgaatct gtaaaaatta attgtacaag gcccagcaac    900

aatacaagaa aaagtataca tataggacca gggagagcat tttatacaac aggagaaata    960

ataggagata taagacaagc acattgtaac attagtagag cacaatggaa taacacttta   1020

aaacagatag ttgaaaaatt aagagaacaa tttaataata aaacaatagt ctttactcac   1080

tcctcaggag gggatccaga aattgtaatg cacagtttta attgtggagg ggaatttttc   1140

tactgtaatt caacacaact gtttaatagt acttggaatg atactgaaaa gtcaagtggc   1200

actgaaggaa atgacaccat catactccca tgcagaataa aacaaattat aaacatgtgg   1260

caggaagtgg gaaaagcaat gtatgctcct cccattaaag gacaaattag atgttcatca   1320

aatattacag ggctgctatt aacaagagat ggtggtaaaa atgagagtga gatcgagatc   1380

ttcagacctg gaggaggaga catgagggac aattggagaa gtgaattata taaatataaa   1440

gtagtaaaaa ttgaaccatt aggagtagca cccaccaagg caaagagaag agtggtgcaa   1500

agagaaaaaa gagcagtggg aataggagct ttgttccttg ggttcttggg agcagcagga   1560

agcactatgg gcgcagcgtc aatgacactg acggtacagg ccagacaatt attgtctggt   1620

atagtgcaac agcaaaacaa tttgctgagg gctattgagg cgcaacagca tatgttgcaa   1680

ctcacagtct ggggcatcaa gcagctccag gcaagagtcc tggctgtgga aagataccta   1740

aaggatcaac agctcatggg gatttggggt tgctctggaa aactcatttg caccactgct   1800

gtgccttgga atactagttg gagtaataaa tctctggata gtatttggaa taacatgacc   1860

tggatggagt gggaaaaaga aattgagaat tacacaaaca caatatacac cctaattgaa   1920

gaatcgcaga tccaacaaga aaagaatgaa caagaattat tggaattaga taaatgggca   1980

agtttgtgga attggtttgg cataacaaaa tggctgtggt atataaaaat attcataatg   2040

atagtaggag gcttgatagg tttaagaata gtttttttctg tactttctat agtgaataga   2100

gttaggcagg gatactcacc cttatcgttt cagaccctcc tcccagcaac gaggggaccc   2160
```

```
gacaggcccg aaggaatcga agaagaaggt ggagagagag acagagacag atccggacaa   2220

ttagtgaacg gattcttagc acttatctgg gtcgacctgc ggagcctgtt cctcttcagc   2280

taccaccgct tgagagactt actcttgact gtaacgagga ttgtggaact tctgggacgc   2340

agggggtggg aaatcctgaa atactggtgg aatctcctac agtattggag tcaggaacta   2400

aagaatagtg ctgttagctt gcttaatgcc acagctatag cagtagctga ggggacagat   2460

aggattatag aagtagtaca aagagtttat agggctattc tccacatacc tacaagaata   2520

agacagggct tggaaagggc tttgctataa                                    2550
```

<210> SEQ ID NO 16
<211> LENGTH: 2571
<212> TYPE: DNA
<213> ORGANISM: Human immunodeficiency virus type 1

<400> SEQUENCE: 16

```
atgagagtga aggagaaata tcagcacttg tggagatggg ggtggagatg gggcaccatg     60

ctccttggga tgttgatgat ctgtagtgct acagaaaaat tgtgggtcac agtctattat    120

ggggtacctg tgtggaagga agcaaccacc actctatttt gtgcatcaga tgctaaagca    180

tatgatacag aggtacataa tgtttgggcc acacatgcct gtgtacccac agaccccaac    240

ccacaagaag tagtattggt aaatgtgaca gaaaatttta acatgtggaa aaatgacatg    300

gtagaacaga tgcatgagga tataatcagt ttatgggatc aaagcctaaa gccatgtgta    360

aaattaaccc cactctgtgt tagtttaaag tgcactgatt tgaagaatga tactaatacc    420

aatagtagta gcgggagaat gataatggag aaaggagaga taaaaaactg ctctttcaat    480

atcagcacaa gcataagagg taaggtgcag aaagaatatg catttttta taaacttgat    540

ataataccaa tagataatga tactaccagc tataagttga caagttgtaa cacctcagtc    600

attacacagg cctgtccaaa ggtatccttt gagccaattc ccatacatta ttgtgccccg    660

gctggttttg cgattctaaa atgtaataat aagacgttca atggaacagg accatgtaca    720

aatgtcagca cagtacaatg tacacatgga attaggccag tagtatcaac tcaactgctg    780

ttaaatggca gtctagcaga agaagaggta gtaattagat ctgtcaattt cacggacaat    840

gctaaaacca taatagtaca gctgaacaca tctgtagaaa ttaattgtac aagacccaac    900

aacaatacaa gaaaaagaat ccgtatccag agaggaccag ggagagcatt tgttacaata    960

ggaaaaatag gaaatatgag acaagcacat tgtaacatta gtagagcaaa atggaataac   1020

actttaaaac agatagctag caaattaaga gaacaatttg gaaataataa aacaataatc   1080

tttaagcaat cctcaggagg ggacccagaa attgtaacgc acagttttaa ttgtggaggg   1140

gaatttttct actgtaattc aacacaactg tttaatagta cttggtttaa tagtacttgg   1200

agtactgaag ggtcaaataa cactgaagga agtgacacaa tcaccctccc atgcagaata   1260

aaacaaatta taaacatgtg gcagaaagta ggaaaagcaa tgtatgcccc tcccatcagt   1320

ggacaaatta gatgttcatc aaatattaca gggctgctat taacaagaga tggtggtaat   1380

agcaacaatg agtccgagat cttcagacct ggaggaggag atatgaggga caattggaga   1440

agtgaattat ataaatataa agtagtaaaa attgaaccat taggagtagc acccaccaag   1500

gcaaagagaa gagtggtgca gagagaaaaa agagcagtgg gaataggagc tttgttcctt   1560

gggttcttgg gagcagcagg aagcactatg ggcgcagcct caatgacgct gacggtacag   1620

gccagacaat tattgtctgg tatagtgcag cagcagaaca atttgctgag ggctattgag   1680
```

```
gcgcaacagc atctgttgca actcacagtc tggggcatca agcagctcca ggcaagaatc   1740

ctggctgtgg aaagatacct aaaggatcaa cagctcctgg ggatttgggg ttgctctgga   1800

aaactcattt gcaccactgc tgtgccttgg aatgctagtt ggagtaataa atctctggaa   1860

cagatttgga atcacacgac ctggatggag tgggacagag aaattaacaa ttacacaagc   1920

ttaatacact ccttaattga agaatcgcaa aaccagcaag aaaagaatga acaagaatta   1980

ttggaattag ataaatgggc aagtttgtgg aattggttta acataacaaa ttggctgtgg   2040

tatataaaat tattcataat gatagtagga ggcttggtag gtttaagaat agtttttgct   2100

gtactttcta tagtgaatag agttaggcag ggatattcac cattatcgtt tcagacccac   2160

ctcccaaccc cgaggggacc cgacaggccc gaaggaatag aagaagaagg tggagagaga   2220

gacagagaca gatccattcg attagtgaac ggatccttgg cacttatctg ggacgatctg   2280

cggagcctgt gcctcttcag ctaccaccgc ttgagagact tactcttgat tgtaacgagg   2340

attgtggaac ttctgggacg cagggggtgg gaagccctca aatattggtg gaatctccta   2400

cagtattgga gtcaggaact aaagaatagt gctgttagct tgctcaatgc cacagccata   2460

gcagtagctg aggggacaga tagggttata gaagtagtac aaggagcttg tagagctatt   2520

cgccacatac ctagaagaat aagacagggc ttggaaagga ttttgctata a            2571
```

```
<210> SEQ ID NO 17
<211> LENGTH: 863
<212> TYPE: PRT
<213> ORGANISM: Human immunodeficiency virus type 1

<400> SEQUENCE: 17

Met Arg Val Lys Gly Ile Arg Lys Asn Tyr Gln His Leu Trp Lys Trp
1               5                   10                  15

Gly Met Leu Thr Met Leu Leu Gly Ile Leu Met Ile Cys Asn Val Thr
            20                  25                  30

Gly Asn Leu Trp Val Thr Val Tyr Tyr Gly Val Pro Val Trp Lys Glu
        35                  40                  45

Ala Thr Thr Thr Leu Phe Cys Ala Ser Asp Ala Lys Ser Tyr Asp Thr
    50                  55                  60

Glu Val His Asn Val Trp Ala Thr His Ala Cys Val Pro Thr Asp Pro
65                  70                  75                  80

Ser Pro Gln Glu Ile Arg Met Glu Asn Val Thr Glu Asn Phe Asn Val
                85                  90                  95

Trp Lys Asn Asn Met Val Asp Gln Met His Glu Asp Ile Ile Ser Leu
            100                 105                 110

Trp Asp Glu Ser Leu Lys Pro Cys Val Lys Leu Thr Pro Leu Cys Val
        115                 120                 125

Asn Leu Asn Cys Thr Asp Lys Val Thr Val Asn Asn Ser Thr Ile Lys
    130                 135                 140

Asn Thr Thr Asn Asp Asp Gly Val Gly Met Met Asp Lys Glu Met Lys
145                 150                 155                 160

Asn Cys Ser Phe Asn Val Thr Thr Asn Glu Gly Asn Lys Val Arg Lys
                165                 170                 175

Glu Tyr Ala Leu Leu Tyr Lys Leu Asp Val Val Ser Ile Asp Gly Asn
            180                 185                 190

Lys Asn Asn Asn Asn Tyr Ser Asn Tyr Arg Leu Ile Ser Cys Asn Thr
        195                 200                 205

Ser Val Ile Thr Gln Ala Cys Pro Lys Val Ser Phe Glu Pro Ile Pro
    210                 215                 220
```

```
Ile His Tyr Cys Ala Pro Ala Gly Phe Ala Ile Leu Lys Cys Asn Asp
225                 230                 235                 240

Lys Lys Phe Asn Gly Lys Gly Glu Cys Lys Asn Val Ser Thr Val Gln
                245                 250                 255

Cys Thr His Gly Ile Arg Pro Val Val Ser Thr His Leu Leu Leu Asn
            260                 265                 270

Gly Ser Leu Ala Glu Glu Glu Val Val Ile Arg Ser Asp Asn Phe Ser
        275                 280                 285

Asn Asn Ala Lys Thr Ile Ile Val Gln Leu Asn Lys Thr Val Lys Ile
    290                 295                 300

Asn Cys Thr Arg Pro Asn Asn Asn Thr Arg Arg Ser Ile Ser Phe Gly
305                 310                 315                 320

Pro Gly Arg Ala Trp His Ala Thr Thr Asp Ile Val Gly Asp Ile Arg
                325                 330                 335

Gln Ala His Cys Thr Ile Asn Gly Thr Glu Trp Asn Asn Ile Leu Lys
            340                 345                 350

Leu Val Val Ser Lys Leu Gln Glu Gln Tyr Gly Thr Asn Lys Thr Ile
        355                 360                 365

Arg Phe Glu Gln Pro Val Gln Gly Gly Asp Leu Glu Ile Val Met His
    370                 375                 380

Ser Phe Asn Cys Gly Gly Glu Phe Phe Tyr Cys Asn Thr Ser Gln Leu
385                 390                 395                 400

Phe Asn Ser Thr Trp Asp Asn Thr Ser Thr Gly Asn Asn Thr Glu Glu
                405                 410                 415

Asp Gly Thr Leu Thr Leu Pro Cys Lys Ile Arg Gln Ile Ile Asn Met
            420                 425                 430

Trp Gln Lys Val Gly Lys Ala Met Tyr Ala Pro Pro Ile Ser Gly Arg
        435                 440                 445

Ile Asn Cys Leu Ser Asn Ile Thr Gly Leu Leu Leu Met Arg Asp Gly
    450                 455                 460

Gly Ser Asn Asp Thr Asn Glu Pro Glu Ile Phe Arg Pro Gly Gly Gly
465                 470                 475                 480

Asp Met Arg Asp Asn Trp Arg Ser Glu Leu Tyr Lys Tyr Lys Val Ile
                485                 490                 495

Lys Ile Glu Pro Leu Gly Ile Ala Pro Thr Lys Ala Lys Arg Arg Val
            500                 505                 510

Val Gln Lys Glu Lys Arg Ala Val Gly Leu Gly Ala Met Phe Leu Gly
        515                 520                 525

Phe Leu Gly Ala Ala Gly Ser Thr Met Gly Ala Ala Ser Leu Thr Leu
    530                 535                 540

Thr Val Gln Ala Arg Gln Leu Leu Ser Gly Ile Val Gln Gln Gln Ser
545                 550                 555                 560

Lys Leu Leu Arg Ala Ile Glu Ala Gln Gln His Leu Leu Gln Leu Thr
                565                 570                 575

Val Trp Gly Ile Lys Gln Leu Gln Ala Arg Val Leu Ala Val Glu Ala
            580                 585                 590

Tyr Leu Lys Asp Gln Gln Leu Leu Gly Ile Trp Gly Cys Ser Gly Lys
        595                 600                 605

Arg Ile Cys Thr Thr Val Val Pro Trp Asn Asn Ser Trp Ser Asn Lys
    610                 615                 620

Ser Tyr Asn Asp Ile Trp Asp Asn Met Thr Trp Met Gln Trp Asp Lys
625                 630                 635                 640
```

```
Glu Ile Glu Asn Tyr Thr Gly Gln Ile Tyr Thr Leu Ile Glu Glu Ala
                645                 650                 655

Gln Ile Gln Gln Glu Lys Asn Glu Gln Glu Leu Leu Glu Leu Asp Lys
            660                 665                 670

Trp Ala Ser Leu Trp Asn Trp Phe Asp Ile Thr Lys Trp Leu Trp Tyr
        675                 680                 685

Ile Lys Ile Phe Ile Met Ile Val Gly Gly Leu Ile Gly Leu Arg Ile
    690                 695                 700

Ile Phe Thr Val Leu Ser Ile Val Asn Arg Val Arg Gln Gly Tyr Ser
705                 710                 715                 720

Pro Leu Ser Phe Gln Thr His Leu Pro Thr Pro Arg Gly Pro Asp Arg
                725                 730                 735

Pro Glu Gly Ile Glu Glu Glu Gly Gly Glu Arg Asp Arg Gly Gly Ser
            740                 745                 750

Gly Arg Leu Val Asn Gly Phe Leu Ala Ile Phe Trp Val Asp Leu Arg
        755                 760                 765

Ser Leu Cys Leu Phe Ser Tyr His Arg Leu Arg Asp Leu Leu Leu Ile
    770                 775                 780

Val Ala Arg Thr Val Glu Leu Leu Gly Arg Arg Gly Trp Glu Ala Leu
785                 790                 795                 800

Lys Tyr Leu Trp Asn Leu Leu Gln Tyr Trp Ile Gln Glu Leu Arg Asn
                805                 810                 815

Ser Ala Val Ser Leu Leu Asn Ala Thr Ala Ile Ala Val Gly Glu Gly
            820                 825                 830

Thr Asp Arg Val Ile Glu Val Val Gln Arg Ile Phe Arg Ala Val Ile
        835                 840                 845

Asn Ile Pro Arg Arg Ile Arg Gln Gly Leu Glu Arg Ile Leu Leu
    850                 855                 860
```

<210> SEQ ID NO 18
<211> LENGTH: 858
<212> TYPE: PRT
<213> ORGANISM: Human immunodeficiency virus type 1

<400> SEQUENCE: 18

```
Met Arg Val Lys Gly Ile Lys Lys Asn Cys Gln Gly Leu Trp Arg Trp
1               5                   10                  15

Gly Met Met Leu Leu Gly Ile Leu Met Ile Cys Ser Ala Thr Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Glu Thr Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Lys Met Met Asn Val Thr Asn Thr Asn Ser Ser Ala Thr
    130                 135                 140

Thr Asn Thr Ser Ser Ser Glu Asn Pro Met Glu Glu Met Lys Asn Cys
145                 150                 155                 160
```

```
Ser Phe Asn Ile Thr Thr His Leu Arg Asp Gln Val Lys Lys Glu Tyr
                165                 170                 175

Ala Thr Phe Tyr Asn Leu Asp Leu Val Pro Ile Ser Asp Lys Asn Asp
            180                 185                 190

Ser Lys Tyr Met Leu Ala Ser Cys Asn Thr Ser Val Ile Thr Gln Ala
        195                 200                 205

Cys Pro Lys Val Ser Phe Glu Pro Ile Pro Ile His Tyr Cys Ala Pro
    210                 215                 220

Ala Gly Phe Ala Ile Leu Lys Cys Asn Asn Lys Thr Phe Asn Gly Lys
225                 230                 235                 240

Gly Pro Cys Thr Asn Val Ser Thr Val Gln Cys Thr His Gly Ile Lys
                245                 250                 255

Pro Val Val Ser Thr Gln Leu Leu Leu Asn Gly Ser Leu Ala Glu Lys
            260                 265                 270

Glu Ile Val Ile Arg Ser Glu Asn Leu Thr Asn Asn Ala Lys Thr Ile
        275                 280                 285

Ile Val Gln Leu Asn Glu Ser Val Ile Ile Asn Cys Thr Arg Pro Asn
    290                 295                 300

Asn Asn Thr Arg Lys Ser Ile His Ile Gln Pro Gly Arg Ala Phe Tyr
305                 310                 315                 320

Ala Thr Gly Glu Ile Ile Gly Asn Ile Arg Gln Ala Tyr Cys Thr Leu
                325                 330                 335

Asn Gly Thr Glu Trp Asn Asn Thr Leu Lys Gln Ile Val Asp Lys Leu
            340                 345                 350

Arg Glu Glu Phe Lys Asn Lys Thr Ile Thr Phe Asn Gln Ser Ser Gly
        355                 360                 365

Gly Asp Pro Glu Ile Val Met His Thr Phe Asn Cys Gly Gly Glu Phe
    370                 375                 380

Phe Tyr Cys Asn Thr Thr Lys Leu Phe Asn Ser Thr Trp Asn Ile Asn
385                 390                 395                 400

Gly Thr Trp Lys Gly Thr Glu Glu Ser Asn Ile Thr Leu Gln Cys Lys
                405                 410                 415

Ile Lys Gln Ile Ile Asn Met Trp Gln Glu Val Gly Lys Ala Met Tyr
            420                 425                 430

Ala Pro Pro Ile Lys Gly Gln Ile Asn Cys Ser Ser Tyr Ile Thr Gly
        435                 440                 445

Leu Leu Leu Thr Arg Asp Gly Gly Tyr Glu Ser Arg Asn Gly Thr Glu
    450                 455                 460

Ile Phe Arg Pro Gly Gly Gly Asn Met Arg Asp Asn Trp Arg Ser Glu
465                 470                 475                 480

Leu Tyr Lys Tyr Lys Val Val Lys Ile Glu Pro Ile Gly Val Ala Pro
                485                 490                 495

Thr Lys Ala Lys Arg Arg Val Val Gln Arg Glu Lys Arg Ala Val Gly
            500                 505                 510

Ile Gly Ala Val Phe Leu Gly Phe Leu Gly Ala Ala Gly Ser Thr Met
        515                 520                 525

Gly Ala Ala Ser Ile Thr Leu Thr Val Gln Ala Arg Gln Leu Leu Ser
    530                 535                 540

Gly Ile Val Gln Gln Gln Asn Asn Leu Leu Arg Ala Ile Glu Ala Gln
545                 550                 555                 560

Gln His Leu Leu Gln Leu Thr Val Trp Gly Ile Lys Gln Leu Gln Ala
                565                 570                 575
```

```
Arg Leu Leu Ala Val Glu Arg His Leu Lys Asp Gln Gln Leu Leu Gly
            580                 585                 590

Ile Trp Gly Cys Ser Gly Lys Leu Ile Cys Thr Thr Ala Val Pro Trp
        595                 600                 605

Asn Thr Ser Trp Ser Asn Lys Ser Leu Asn Gln Ile Trp Asn Asn Met
    610                 615                 620

Thr Trp Met Glu Trp Glu Arg Glu Ile Asp Asn Tyr Thr Gly Leu Ile
625                 630                 635                 640

Tyr Ser Leu Ile Glu Glu Ser Gln Asn Gln Gln Asp Lys Asn Glu Gln
                645                 650                 655

Glu Leu Leu Ala Leu Asp His Trp Ala Ser Leu Trp Asn Trp Phe Ser
            660                 665                 670

Ile Thr Asn Trp Leu Trp Tyr Ile Lys Ile Phe Ile Ile Ile Val Gly
        675                 680                 685

Gly Leu Ile Gly Leu Arg Ile Val Phe Ala Val Leu Ser Ile Val Asn
    690                 695                 700

Arg Val Arg Gln Gly Tyr Ser Pro Leu Ser Phe Gln Thr Leu Leu Leu
705                 710                 715                 720

Thr Gln Arg Gly Pro Asp Arg Pro Gly Gly Ile Glu Glu Glu Gly Gly
                725                 730                 735

Glu Arg Asp Arg Asp Arg Ser Gly Gln Leu Val Asn Gly Phe Leu Ala
            740                 745                 750

Ile Val Trp Val Asp Leu Arg Ser Leu Cys Leu Phe Leu Tyr Arg His
        755                 760                 765

Leu Arg Asp Leu Leu Leu Ile Val Thr Arg Thr Val Glu Leu Leu Gly
    770                 775                 780

Leu Arg Gly Trp Glu Ala Leu Lys Tyr Leu Trp Asn Leu Leu Gln Tyr
785                 790                 795                 800

Trp Ser Gln Glu Leu Lys Asn Ser Ala Val Ser Leu Leu Asn Ala Ile
                805                 810                 815

Ala Ile Ala Val Ala Glu Gly Thr Asp Arg Val Ile Glu Ala Leu Gln
            820                 825                 830

Arg Ala Cys Arg Ala Ile Leu His Ile Pro Arg Arg Ile Arg Gln Gly
        835                 840                 845

Ile Glu Arg Ala Val Leu Glu Asp Gly Trp
    850                 855
```

<210> SEQ ID NO 19
<211> LENGTH: 856
<212> TYPE: PRT
<213> ORGANISM: Human immunodeficiency virus type 1

<400> SEQUENCE: 19

```
Met Arg Val Met Glu Ile Lys Arg Asn Tyr Gln His Leu Trp Arg Gly
1               5                   10                  15

Gly Thr Leu Leu Leu Gly Ile Leu Met Ile Cys Ser Ala Ala Glu Asp
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Ala
    50                  55                  60

His Asn Val Trp Ala Thr His Ala Cys Val Pro Thr Asp Pro Asn Pro
65                  70                  75                  80

Gln Glu Val Lys Leu Val Asn Val Thr Glu Asn Phe Asn Met Trp Lys
                85                  90                  95
```

```
Asn Asn Met Val Glu Gln Met His Glu Asp Ile Ile Ser Leu Trp Asp
            100                 105                 110

Glu Ser Leu Lys Pro Cys Val Lys Leu Thr Pro Leu Cys Val Thr Leu
        115                 120                 125

Asn Cys Thr Asp Trp Lys Gly Asn Thr Thr Thr Thr Pro Thr Thr Thr
    130                 135                 140

Leu Ser Ser Lys Gly Lys Met Met Glu Gly Gly Glu Met Lys Asn Cys
145                 150                 155                 160

Ser Phe Asn Val Thr Ser Gly Ile Arg Asp Lys Val Gln Lys Asp Tyr
                165                 170                 175

Ala Phe Phe Tyr Lys Leu Asp Leu Val Gln Ile Asp Asp Ser Asp Asn
            180                 185                 190

Thr Ser Tyr Arg Leu Ile Ser Cys Ser Thr Ser Val Ile Thr Gln Ala
        195                 200                 205

Cys Pro Lys Thr Ser Phe Glu Pro Ile Pro Ile His Tyr Cys Ala Pro
    210                 215                 220

Ala Gly Phe Ala Ile Leu Lys Cys Lys Asp Lys Lys Phe Asn Gly Thr
225                 230                 235                 240

Gly Pro Cys Lys Asn Val Ser Thr Val Gln Cys Thr His Gly Ile Arg
                245                 250                 255

Pro Val Val Ser Thr Gln Leu Leu Leu Asn Gly Ser Leu Ala Glu Glu
            260                 265                 270

Glu Ile Val Ile Arg Ser Glu Asn Ile Ser Asp Asn Val Lys Thr Ile
        275                 280                 285

Ile Val Gln Leu Asn Glu Thr Val Glu Ile Asn Cys Thr Arg Pro Asn
    290                 295                 300

Asn Asn Thr Arg Arg Ser Ile His Ile Gly Pro Gly Arg Ala Phe Tyr
305                 310                 315                 320

Gly Thr Asp Val Ile Gly Asp Ile Arg Gln Ala His Cys Asn Ile Ser
                325                 330                 335

Arg Thr Gln Trp Asn Asn Thr Leu Gln Arg Val Val Lys Lys Leu Arg
            340                 345                 350

Glu Ile Lys Gln Phe Lys Asn Lys Thr Ile Val Phe Lys Gln Ser Ser
        355                 360                 365

Gly Gly Asp Pro Glu Ile Val Met His Thr Phe Asn Cys Gly Gly Glu
    370                 375                 380

Phe Phe Tyr Cys Asn Ser Ser Gly Leu Phe Asn Ser Thr Trp Pro Ser
385                 390                 395                 400

Asn Ser Thr Gln Asn Ser Thr Glu Gly Ser Asn Asn Thr Ile Thr Leu
                405                 410                 415

Pro Cys Arg Ile Arg Gln Ile Ile Asn Met Trp Gln Glu Val Gly Lys
            420                 425                 430

Ala Met Tyr Ala Pro Pro Ile Gln Gly Gln Ile Arg Cys Ser Ser Asn
        435                 440                 445

Ile Thr Gly Ile Leu Leu Thr Arg Asp Gly Gly Asn Val Asn Val Thr
    450                 455                 460
```

```
Asp Glu Ile Phe Arg Pro Gly Gly Gly Asn Met Lys Asp Asn Trp Arg
465                 470                 475                 480

Ser Glu Leu Tyr Lys Tyr Lys Val Val Gln Ile Glu Pro Leu Gly Leu
                485                 490                 495

Ala Pro Thr Arg Ala Arg Arg Arg Val Val Gln Arg Glu Lys Arg Ala
            500                 505                 510

Val Gly Met Gly Ala Leu Phe Leu Gly Phe Leu Gly Ala Ala Gly Ser
        515                 520                 525

Thr Met Gly Ala Ala Ser Met Thr Leu Thr Val Gln Ala Arg Thr Leu
    530                 535                 540

Leu Ser Gly Ile Val Gln Gln Gln Ser Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Val Leu Ala Val Glu Arg Tyr Leu Arg Asp Gln Gln Leu
            580                 585                 590

Leu Gly Ile Trp Gly Cys Ser Gly Lys Leu Ile Cys Thr Thr Asn Val
        595                 600                 605

Pro Trp Asn Ala Ser Trp Ser Asn Lys Ser Met Asp Glu Ile Trp Glu
    610                 615                 620

Asn Met Thr Trp Met Gln Trp Glu Arg Glu Ile Asp Asn Tyr Thr Asp
625                 630                 635                 640

Leu Ile Tyr Asn Leu Ile Glu Lys Ser Gln Asn Gln Gln Glu Lys Asn
                645                 650                 655

Glu Gln Glu Leu Leu Ala Leu Asp Lys Trp Ala Ser Leu Trp Asn Trp
            660                 665                 670

Phe Asn Ile Ser His Trp Leu Trp Tyr Ile Lys Ile Phe Ile Met Ile
        675                 680                 685

Val Gly Gly Leu Ile Gly Leu Arg Ile Val Phe Thr Val Phe Ser Ile
    690                 695                 700

Val Asn Arg Val Arg Gln Gly Tyr Ser Pro Leu Ser Phe Gln Thr Arg
705                 710                 715                 720

Phe Pro Ala Gln Arg Gly Pro Asp Arg Pro Glu Gly Ile Glu Glu Glu
                725                 730                 735

Gly Gly Asp Arg Asp Arg Asp Arg Ser Gly His Leu Val Asp Gly Phe
            740                 745                 750

Leu Ala Ile Phe Trp Val Asp Leu Arg Ser Leu Phe Leu Phe Ser Tyr
        755                 760                 765

His Arg Leu Arg Asp Leu Leu Leu Ile Ala Ala Arg Ile Val Glu Leu
    770                 775                 780

Leu Gly Arg Arg Gly Trp Glu Leu Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Thr Thr Ala Ile Ala Val Ala Glu Gly Thr Asp Arg Val Ile Glu Ile
            820                 825                 830

Leu Gln Gly Ala Phe Arg Ala Ile Ile His Ile Pro Thr Arg Ile Arg
        835                 840                 845

Gln Gly Leu Glu Arg Ala Leu Leu
    850                 855
```